US010993391B2

(12) United States Patent
Houben et al.

(10) Patent No.: US 10,993,391 B2
(45) Date of Patent: May 4, 2021

(54) GENERATION OF HAPLOID PLANTS

(71) Applicant: KWS SAAT SE & CO. KGAA, Einbeck (DE)

(72) Inventors: Andreas Houben, Quedlinburg (DE); Raheleh Karimi-Ashiyani, Gatersleben (DE); Takayoshi Ishii, Gatersleben (DE); Nils Stein, Quedlinburg (DE); Jochen Kumlehm, Potsdam (DE); Christof Bolduan, Einbeck (DE); Frank Breuer, Einbeck (DE); Monika Kloiber-Maitz, Einbeck (DE); Markus Niessen, Hannover (DE); Milena Ouzunova, Göttingen (DE); Britta Schulz, Einbeck (DE); Silke Wieckhorst, Einbeck (DE)

(73) Assignee: KWS SAAT SE & CO. KGAA, Einbeck (DE)

( * ) Notice: Subject to any disclaimer, the term of this patent is extended or adjusted under 35 U.S.C. 154(b) by 61 days.

(21) Appl. No.: 15/507,538

(22) PCT Filed: Aug. 28, 2015

(86) PCT No.: PCT/EP2015/001752
§ 371 (c)(1),
(2) Date: Feb. 28, 2017

(87) PCT Pub. No.: WO2016/030019
PCT Pub. Date: Mar. 3, 2016

(65) Prior Publication Data
US 2017/0280646 A1    Oct. 5, 2017

(30) Foreign Application Priority Data

Aug. 28, 2014   (EP) ..................................... 14182719
Dec. 23, 2014   (EP) ..................................... 14004389

(51) Int. Cl.
*A01H 1/08*     (2006.01)
*A01H 5/00*     (2018.01)
*A01H 5/06*     (2018.01)
*A01H 5/10*     (2018.01)
*C07K 14/415*   (2006.01)
*C12N 15/82*    (2006.01)
*C12N 15/00*    (2006.01)

(52) U.S. Cl.
CPC ................ *A01H 1/08* (2013.01); *A01H 5/00* (2013.01); *A01H 5/06* (2013.01); *A01H 5/10* (2013.01); *C07K 14/415* (2013.01); *C12N 15/8287* (2013.01); *C12N 15/8289* (2013.01); *C12N 15/00* (2013.01)

(58) Field of Classification Search
CPC ............... A01H 5/10; C12N 15/8289
See application file for complete search history.

(56) References Cited

U.S. PATENT DOCUMENTS

2011/0083202 A1    4/2011    Chan et al.
2014/0090099 A1    3/2014    Chan et al.

FOREIGN PATENT DOCUMENTS

WO    2011044132 A1    4/2011
WO    2014110274 A2    7/2014

OTHER PUBLICATIONS

Karimi-Ashtiyani, R et al., PNAS; Sep. 8, 2015, vo. 112, No. 36; pp. 11211-11216.*
Kasha and Kao, Nature vol. 225; Feb. 28, 1970 pp. 874-876.*
Sanei, M. et al. PNAS, Aug. 16, 2011, pp. 1-15.*
Kasha and Kao, Nature vol. 225; Feb. 28, 1970 pp. 874-876 (Year: 1970).*
Sanei, M. et al. PNAS, Aug. 16, 2011, 1-15 pp. (Year: 2011).*
Ravi, M. And Chan, S., Nature vol. 464; Mar. 25, 2010, pp. 615-619. (Year: 2010).*
GenBank Accession AFK37617.1 Submitted (May 25, 2012) Plant Genomics, J. Craig Venter Institute. (Year: 2012).*
ICRISAT Asia Regional Planning Meeting, Patancheru, India, Feb. 10-12, 2014; pp. 1-18 (Year: 2014).*
GenBank Accession AFK37617.1; (May 25, 2012) (Year: 2012).*
Chemczynski, P. et al., "Single-Step Method of RNA Isolation by Acid Guanidinium Thiocyanate-Phenol-Chloroform Extraction", Analytical Biochemistry (1987), vol. 162, pp. 156-159.
Clough, S.J. et al., "Floral dip: a simplified method for Agrobacterium-mediated transformation of *Arabidopsis thaliana*", The Plant Journal (1988), vol. 16(8), pp. 735-743.
Comai, L., "Genome Elimination: Translating Basic Research into a Future Tool for Plant Breeding", PLOS Biology (2014), vol. 12, Issue 6, e1001876, pp. 1-4.
Edwards, K. et al., "A simple and rapid method for the preparation of plant genomic DNA for PCR analysis", Nucleic Acids Research (1991), vol. 19, No. 6, p. 1349.
Galbraith, D.W. et al., "Rapid Flow Cytometric Analysis of the Cell Cycle in Intact Plant Tissues", Science (1983), vol. 220(4601), pp. 1049-1051. [doi: 10.1126/science.220.4601.1049].
Gottwald, Sven et al., "Tilling in the two-rowed barley cultivar 'Barke' reiveals preferred sites of functional diversity in the gene HvHoxl", BMC Research Notes (2009), vol. 2(258) pp. 1-14.

(Continued)

*Primary Examiner* — Russell Kallis
(74) *Attorney, Agent, or Firm* — Troutman Pepper Hamilton Sanders LLP

(57) ABSTRACT

The present invention relates to non-tränsgenic and transgenic plants, preferably crop plants, comprising a mutation causing an alteration of the amino acid sequence in the CATD domain of the centromere histone H3 (CENH3), preferably within the loop1 or the α2-helix of the CATD domain, which have the biological activity of a haploid inducer. Further, the present invention provides methods of generating the plants of the present invention and haploid and double haploid plants obtainable by crossing the plants of the present invention with wildtype plants as well as methods of facilitating cytoplasm exchange.

16 Claims, 2 Drawing Sheets

Specification includes a Sequence Listing.

(56) References Cited

OTHER PUBLICATIONS

International Preliminary Report and Written Opinion of the International Searching Authority dated Feb. 28, 2017 issued in PCT/EP2015/001752.

International Search Report dated Dec. 18, 2015 issued in the International Application No. PCT/EP2015/001752.

Karimi-Ashtiyani, R. et al., "Point mutation impairs centromeric CENH3 loading and induces haploid plants", Proceedings of the National Academy of Sciences (2015), vol. 112(36), pp. 11211-11216. XP055233787, ISSN: 0027-8424, DOI: 10.1073/pnas.1504333112.

Lermontova, I. et al., "CENH3 for Establishing and Maintaining Centromeres", Plant Centromere Biology (2013), XP0551632252, ISBN: 978-1-119-94921-3 pp. 67-82, DOI: 10.1002/9871118525715.ch6.

Lermontova, I. et al. "Knockdown of CENH3 in *Arabidopsis* reduces mitotic divisions and causes sterility by distributed meiotic chromosome segregation", The Plant Journal (2011), vol. 68, pp. 40-50. [doi: 10.1111/j.1365-313X.2011.04664/x].

Lindsey, K. et al., "Transformation of Sugarbeet (*Beta vullgaris*) by Agrobacterium tumefaciens", Journal of Experimental Botany (1990), vol. 41, No. 226, pp. 529-536.

Marin-Rodriguez, B., "Can Point Mutations in Kinetochore Proteins Create Haploid Plants in *Arabidopsis thaliana*?", UC Davis Explorations (2014), pp. 7-7, XP055191293, Retrieved from the Internet: URL:http://explorations.usdavis.edu/docs/2014/2014explorations.pdf [retrieved on May 22, 2015].

Neuffer, M.G. et al., "Mutants of Maize", Cold Spring Harbor Laboratory Press, New York (1997), 468 pages. ISBN 0-87969-444-0. (see attached review).

Ravi, M. et al., "Haploid plants produced by centromere-mediated genome elimination", Nature (2010), vol. 464, pp. 615-619. [doi: 10.1038/nature08842].

Ravi, M. et al, "The Rapidly Evolving Centromere-Specific Histone Has Stringent Functional Requirements in *Arabidopsis thaliana*", Genetics Society of America (2010), vol. 186, pp. 461-471. [doi: 10.1534/genetics.110.120337].

Rost, B. et al., "Combining Evolutionary Information and Neural Networks to Predict Protein Secondary Structure", Proteins: Structure, Function, and Genetics (1994), vol. 19, pp. 55-72.

Rost, B. et al., "Conservation and Prediction of Solvent Accessibility in Protein Families", Proteins: Structure, function, and Genetics (1994), vol. 20, pp. 216-226.

Rost, B. et al., "Transmembrane helices proedicted at 95% accuracy", Protein Science (1995), vol. 4, pp. 521-533.

Sanei, M. et al., "Loss of centromeric histone H3 (CENH3) from centromeres precedes uniparental chromosome elimination in interspecific barley hybrids", PNAS (2011), vol. 108(33), pp. E498-E505. [www.pnas.org/cgi/doi/10.1073/pnas.1103190108].

Written Opinion and International Search Report of the International Searching Authority dated Mar. 3, 2016 issued in International Application No. PCT/EP2015/001752.

Bhatnagar-Mathur, Pooja et al., "Engineering Centromers for Haploidy Induction in Grain Legumes", ICRISAT Asia Regional Planning Meeting (2014), XP055193834.

European Partial Search Report Issued in European Patent Application No. 14004389.4, dated Jun. 12, 2015, 11 pages.

European Extended Search Report Issued in European Patent Application No. 14004389.4, dated Sep. 30, 2015, 16 pages.

International Search Report and Written Opinion Issued in PCT/EP2015/081158, dated Feb. 14, 2017, 24 pages.

Ishii, Takayoshi et al., "Functional characterization of barley CENH3 variants", Plant Molecular Cytogenetics in Genomic and Postgenomic Era (2014), XP55191331, p. 51.

Lermontova, Inna et al., "CENH3 for Establishing and Maintaining Centromeres" In: "Plant Centromere Biology", John Wiley & Sons, Oxford (2013), pp. 67-82.

Moraes, Izabel C.R. et al., "Structural requirements for CENH3 targeting to centromeric chromatin", Ph.D. thesis (2011), XP55191122, pp. 53-56.

Ravi, Maruthachalam et al., "A haploid genetics toolbox for *Arabidopsis thaliana*", Nature Communications (2014), vol. 5, p. 5334.

Ravi, Maruthachalam et al., "Centromere-Mediated Generation of Haploid Plants", Plant Centromere Biology (2013), XP55191054, p. 169-181.

Li et al., "Variation for Thermal Properties of Starch in Tropical Maize Germ Plasm", Cereal Chem. vol. 71, No. 1, 1994, pp. 87-90.

Chan et al., "Chromosome engineering Power tools for plant genetics", Trends in Biotechnology, Elesvier Publications, vol. 28, No. 12, Oct. 8, 2010, pp. 605-610.

Britt et al., Cenh3: An Emerging Player in Haploid Induction Technology, Frontiers in Plant Science, Apr. 12, 2016, vol. 7, Article 357, pp. 1-10.

UniprotKB—QBRVQ9, 20070123.

Lermontova et al., "Loading of *Arabidopsis* Centromeric Histone CENH3 Occurs Mainly during G2 and Requires the Presence of the Histone Fold Domain", The Plant Cell, vol. 18, Oct. 2006, pp. 615-618.

* cited by examiner

GENERATION OF HAPLOID PLANTS

CROSS-REFERENCE TO RELATED APPLICATIONS

This application is a U.S. National Phase of International Patent Application No. PCT/EP2015/001752, filed Aug. 28, 2015, which claims priority to European Patent Application No. EP14182719.6, filed Aug. 28, 2014 and European Patent Application No. EP14004389.4, filed Dec. 23, 2014, all of which are herein incorporated by reference in their entirety.

SEQUENCE LISTING

The instant application contains a Sequence Listing which has been submitted in ASCII format via EFS-Web and is hereby incorporated by reference in its entirety. The ASCII text file was created on Apr. 10, 2017, is named 0219_PCT_Sequence_Listing_corr_ST25.txt, and is 172,511 bytes in size.

DESCRIPTION

The present invention relates to non-transgenic and transgenic plants, preferably crop plants, comprising at least one mutation causing an alteration of an amino acid within the CATD domain of the centromere histone H3 (CENH3), preferably within the loop1 and/or the α2-helix of the CATD domain, which have the biological activity of a haploid inducer. Further, the present invention provides methods of generating the plants of the present invention and haploid and double haploid plants obtainable by crossing the plants of the present invention with wildtype plants as well as methods of facilitating cytoplasm exchange.

The generation and use of haploids is one of the most powerful biotechnological means to improve cultivated plants. The advantage of haploids for breeders is that homozygosity can be achieved already in the first generation after dihaploidization, creating doubled haploid plants, without the need of several backcrossing generations required to obtain a high degree of homozygosity. Further, the value of haploids in plant research and breeding lies in the fact that the founder cells of doubled haploids are products of meiosis, so that resultant populations constitute pools of diverse recombinant and at the same time genetically fixed individuals. The generation of doubled haploids thus provides not only perfectly useful genetic variability to select from with regard to crop improvement, but is also a valuable means to produce mapping populations, recombinant inbreds as well as instantly homozygous mutants and transgenic lines.

Haploids can be obtained by in vitro or in vivo approaches. However, many species and genotypes are recalcitrant to these processes. Alternatively, substantial changes of the centromere-specific histone H3 variant (CENH3, also called CENP-A), by swapping its N-terminal regions and fusing it to GFP ("GFP-tailswap" CENH3), creates haploid inducer lines in the model plant *Arabidopsis thaliana* (Ravi and Chan, Nature, 464 (2010), 615-618; Comai, L, "Genome elimination: translating basic research into a future tool for plant breeding.", PLoS biology, 12.6 (2014)). CENH3 proteins are variants of H3 histone proteins that are members of the kinetochore complex of active centromeres. With these "GFP-tailswap" haploid inducer lines, haploidization occurred in the progeny when a haploid inducer plant was crossed with a wildtype plant. Interestingly, the haploid inducer line was stable upon selfing, suggesting that a competition between modified and wild type centromere in the developing hybrid embryo results in centromere inactivation of the inducer parent and consequently in uniparental chromosome elimination. As a result, the chromosomes containing the altered CENH3 protein are lost during early embryo development producing haploid progeny containing only the chromosomes of the wildtype parent.

Thus, haploid plants can be obtained by crossing "GFP-tailswap" transgenic plants as haploid inducer to wildtype plants. However, as described above, this technique requires substantial changes of the CENH3 protein and the plants comprise a heterologous transgene, which is economically problematic because of increasing public reluctance toward genetically engineered crops.

It is therefore an object of the present invention to overcome the aforementioned problems and in particular to provide alternative haploid inducer plants which do not comprise substantial modifications of their CENH3 protein and/or which are not genetically engineered.

This problem is solved by the subject matter of the independent claims, in particular by a plant having biological activity of a haploid inducer and comprising a nucleotide sequence encoding a centromer histone H3 (CENH3) protein comprising a CATD domain, wherein the nucleotide sequence comprises a mutation causing in the CATD domain an alteration of the amino acid sequence of the CENH3 protein and said alteration confers the biological activity of a haploid inducer. The CATD domain of the CENH3 protein corresponds to amino acid sequence from positions 113 to position 155 as set forth in SEQ ID No. 38 derived from *Arabidopsis thaliana* and/or the CATD domain of the CENH3 protein is encoded by a nucleotide sequence corresponding to nucleotides from position 337 to position 465 as set forth in SEQ ID No. 37 derived from *Arabidopsis thaliana*. The *A. thaliana* sequences serve only as references and do not limit the invention to the particular *A. thaliana* sequences. Due to the high level of conservation ones skilled in the art is able to find the nucleotide sequence and amino acid sequence corresponding to the *A. thaliana* sequences in any other plant material or plant species. In the context of the present invention the term 'alteration' means any modification of the amino acid sequence of the protein CENH3 (including multiple modifications) which are caused by at least one mutation in the nucleotide sequence encoding a centromer histone H3 (CENH3) protein. The nucleotide sequence can be a genomic DNA or the cDNA of the CENH3 gene. An alteration can be a substitution of one or more amino acids, an insertion of one or more amino acids or a deletion of one or more amino acids. Mutations at DNA level which are able to alter the amino acid sequence of the protein CENH3 can be a point mutations leading to an amino acid substitution or a stop codon, insertions or deletion which shift the reading frame of the CENH3 gene, or mutations in the splicing sites.

In one preferred embodiment, the mutation causing an amino acid substitution is located within the loop1 of the CATD domain. The loop1 corresponds to amino acid sequence from positions 114 to position 126 as set forth in SEQ ID No. 38 derived from *Arabidopsis thaliana* and/or the loop1 is encoded by a nucleotide sequence corresponding to nucleotides from position 340 to position 378 as set forth in SEQ ID No. 37 derived from *Arabidopsis thaliana*. The *A. thaliana* sequences serve only as references and do not limit the invention to the particular *A. thaliana* sequences. Due to the high level of conservation ones skilled in the art is able to find the nucleotide sequence and amino acid sequence corresponding to the *A. thaliana* sequences in any other plant material or plant species.

In another preferred embodiment, the at least one mutation causing an amino acid substitution is located within the α2-helix of the CATD domain. The α2-helix corresponds to amino acid sequence from positions 127 to position 155 as set forth in SEQ ID No. 38 derived from *Arabidopsis thaliana* and/or the α2-helix is encoded by a nucleotide sequence corresponding to nucleotides from position 379 to position 465 as set forth in SEQ ID No. 37 derived from *Arabidopsis thaliana*. The *A. thaliana* sequences serve only as references and do not limit the invention to the particular *A. thaliana* sequences. Due to the high level of conservation ones skilled in the art is able to find the nucleotide sequence and amino acid sequence corresponding to the *A. thaliana* sequences in any other plant material or plant species.

CENH3 proteins are variants of H3 histone proteins that are members of the kinetochore complex of active centromeres, i.e. the protein structure on chromosomes where spindle fibres attach during cell division. Basically, CENH3 proteins are characterized by a variable tail domain, which does not form a rigid secondary structure, and a conserved histone fold domain consisting of three α-helical regions, termed α1 to α3, which are connected by two loop sections. Within the histone fold domain the highly conserved CATD domain (CENP-A targeting domain) is located, which is formed by parts of the α1-helix, the complete α2-helix and the connecting loop1. The conserved CATD domain is required for CENH3 loading by chaperones and thus vital for its kinetochore localization and centromere function.

The present inventors surprisingly found that a plant possessing the capability to produce haploid progeny, i.e. a haploid inducer, can be obtained by substituting a single amino acid within the conserved CATD domain, in particular in the loop1 or the α2-helix, of the CENH3 protein. Advantageously, this can be achieved by transgenic as well as non-transgenic methods. Non-transgenic methods are preferred because of enormous costs for deregulation of genetically modified organisms (GMO) as well as increasing public rejection of genetically modified organisms (GMO) or plants generated by means of GMO, in particular crops for human consumption, and extensive market authorisation processes including rigorous safety assessments of such GMOs.

The present invention provides a plant comprising and expressing a CENH3 protein having a CATD domain, wherein in the CATD domain, in particular in the loop1 or the α2-helix, most preferred in the loop1 or the α2-helix having the consensus sequence of SEQ ID No. 49 or 1 respectively, an amino acid, which occurs in the endogenously encoded CENH3 protein of said plant is deleted or substituted by another amino acid. This alteration can confer the biological activity of a haploid inducer to the plant.

In a preferred embodiment the present invention relates to a plant comprising a nucleotide sequence encoding a centromer histone H3 (CENH3) protein comprising a CATD domain, wherein the part of the nucleotide sequence encoding the CATD domain comprises a mutation and wherein the mutation causes an alteration of the amino acid sequence in the CATD domain of the CENH3 protein in the loop1 which a) is encoded by a nucleotide sequence corresponding to nucleotides from position 340 to position 378 as set forth in SEQ ID No. 37 derived from *Arabidopsis thaliana*, which corresponds to amino acid sequence from positions 114 to position 126 as set forth in SEQ ID No. 38 derived from *Arabidopsis thaliana*, or is encoded by a nucleotide sequence corresponds to nucleotides from position 271 to position 306 as set forth in SEQ ID No. 60 derived from *Beta vulgaris*, corresponds to amino acid sequence from positions 91 to position 102 as set forth in SEQ ID No. 61 derived from *Beta vulgaris*, or is encoded by a nucleotide sequence corresponds to nucleotides from position 346 to position 384 as set forth in SEQ ID No. 51 derived from *Brassica napus*, corresponds to amino acid sequence from positions 116 to position 128 as set forth in SEQ ID No. 52 derived from *Brassica napus*, or is encoded by a nucleotide sequence corresponds to nucleotides from position 280 to position 318 as set forth in SEQ ID No. 57 derived from *Zea mays*, corresponds to amino acid sequence from positions 94 to position 106 as set forth in SEQ ID No. 58 derived from *Zea mays*, or is encoded by a nucleotide sequence corresponds to nucleotides from position 280 to position 318 as set forth in SEQ ID No. 54 derived from *Sorghum bicolor*, corresponds to amino acid sequence from positions 94 to position 106 as set forth in SEQ ID No. 55 derived from *Sorghum bicolor*, or is encoded by a nucleotide sequence corresponds to nucleotides from position 208 to position 264 as set forth in SEQ ID No. 33 derived from *Hordeum vulgare* (βCENH3), corresponds to amino acid sequence from positions 70 to position 88 as set forth in SEQ ID No. 34 derived from *Hordeum vulgare* (βCENH3), or having the consensus sequence of SEQ ID No. 49, and b) being positioned within the CATD domain of the CENH3 protein as defined above, or the mutation causes an alteration of the amino acid sequence in the CATD domain of the CENH3 protein in the α2-helix which a) is encoded by a nucleotide sequence corresponding to nucleotides from position 379 to position 465 as set forth in SEQ ID No. 37 derived from *Arabidopsis thaliana*, which corresponds to amino acid sequence from positions 127 to position 155 as set forth in SEQ ID No. 38 derived from *Arabidopsis thaliana*, or is encoded by a nucleotide sequence corresponds to nucleotides from position 307 to position 393 as set forth in SEQ ID No. 60 derived from *Beta vulgaris*, corresponds to amino acid sequence from positions 103 to position 131 as set forth in SEQ ID No. 61 derived from *Beta vulgaris*, or is encoded by a nucleotide sequence corresponds to nucleotides from position 385 to position 471 as set forth in SEQ ID No. 51 derived from *Brassica napus*, corresponds to amino acid sequence from positions 129 to position 157 as set forth in SEQ ID No. 52 derived from *Brassica napus*, or is encoded by a nucleotide sequence corresponds to nucleotides from position 319 to position 405 as set forth in SEQ ID No. 57 derived from *Zea mays*, corresponds to amino acid sequence from positions 107 to position 135 as set forth in SEQ ID No. 58 derived from *Zea mays*, or is encoded by a nucleotide sequence corresponds to nucleotides from position 319 to position 405 as set forth in SEQ ID No. 54 derived from *Sorghum bicolor*, corresponds to amino acid sequence from positions 107 to position 135 as set forth in SEQ ID No. 55 derived from *Sorghum bicolor*, or is encoded by a nucleotide sequence corresponds to nucleotides from position 265 to position 351 as set forth in SEQ ID No. 33 derived from *Hordeum vulgare* (βCENH3), corresponds to amino acid sequence from positions 89 to position 117 as set forth in SEQ ID No. 34 derived from *Hordeum vulgare* (βCENH3), or having the consensus sequence of SEQ ID No. 1, and b) being positioned within the CATD domain of the CENH3 protein as defined above. Thus, preferably, the alteration is located in the loop1 or the α2-helix of the CATD domain. The non-mutated loop1 of the CATD domain is highly conserved among plant species and is 13 amino acids long starting with position 1 and ending with position 13. In the present invention, any amino acid position given with respect to the loop1 or the below described consensus sequence of SEQ ID No. 49 is referring to this numbering system. Preferably, the non-mutated loop1 exhibits the amino acid sequence as given in Table 1.

TABLE 1

Specified amino acids in the loop1 of the CENH3 protein

| Position within the loop1 | Amino acid(s) |
|---|---|
| 1 | T, S or A |
| 2 | H, Q, N, A, Y, F, G, D or E |
| 3 | M, Q, I, F, Y, A, E, N, R, L, H or G |
| 4 | L, F, V, I or Y |
| 5 | A, T, S, C or M |
| 6 | P, N, D, R, A, T, F, R, H, S or K |
| 7 | X |
| 8 | Q, Y, D, K, R, E, G, S, P, H, N or A |
| 9 | I, V or P |
| 10 | N, G, T, E, or S |
| 11 | R or P |
| 12 | W or Y |
| 13 | T, Q or S |

More preferably, the loop1 has the consensus sequence of SEQ ID No. 49, which is

TNFLA PXEVT RWT.
5    10    13

As indicated above, the loop1 comprises unspecified [marked as X] and specified amino acids [marked as one letter code].

The non-mutated α2-helix of the CATD domain is highly conserved among plant species and is 29 amino acids long starting with position 1 and ending with position 29. In the present invention, any amino acid position given with respect to the α2-helix or the below described consensus sequence of SEQ ID No. 1 is referring to this numbering system. Preferably, the non-mutated α2-helix exhibits the amino acid sequence as given in Table 2.

TABLE 2

Specified amino acids in the α2-helix of the CATD domain

| Position within the α2-helix | Amino acid(s) |
|---|---|
| 1 | A, P, V or L |
| 2 | E, D, Q, H or L |
| 3 | A |
| 4 | L or V |
| 5 | V, L, M, I, R, Y or T |
| 6 | S or A |
| 7 | I or L |
| 8 | Q |
| 9 | E |
| 10 | A or S |
| 11 | A or T |
| 12 | E |
| 13 | D, N, F, I or Y |
| 14 | Y, F or H |
| 15 | L, I or V |
| 16 | V or I |
| 17 | G, R, E, H, N, T, E, D or Q |
| 18 | L, M or I |
| 19 | F, M or L |
| 20 | S, E, D or G |
| 21 | D, M, V, N, E, A, R or K |
| 22 | S, G, A or T |
| 23 | M, W, N or H |
| 24 | L or H |
| 25 | C or L |
| 26 | A or T |
| 27 | L or I |
| 28 | H |
| 29 | A or S |

More preferably, the α2-helix has the consensus sequence of SEQ ID No. 1, which is AEALL ALQEA AEDFL VHLFE DAMLC AIHA.
  5       10       15       20       25    29

As indicated above, the α2-helix comprises specified amino acids [marked as one letter code].

According to one preferred embodiment of the present invention, a mutation causing an alteration of the amino acid sequence in the CATD domain of the CENH3 protein of any of the unspecified or the specified amino acid as defined in Table 2 or in SEQ ID No. 1, or in Table 1 or SEQ ID No. 49, preferably a substitution or deletion of the amino acid(s), can produce the desired plant possessing the capability to produce haploid progeny.

An unspecified amino acid as given in Table 1 or in SEQ ID No. 49 is an amino acid which although being specified in a group of particular plant species, in a particular plant genus or in a particular plant species is not conserved in a greater range of plant species. Thus, an unspecified amino acid of SEQ ID No. 49 or as given in Table 1 is in a group of particular plant species, in a particular plant genus or in a particular plant species a well-defined, specific amino acid, which, however, is possibly not found at the same place in another plant species. Thus, an amino acid substitution of an unspecified amino acid of SEQ ID No. 49 or as indicated in Table 1 means that in a plant, namely in a specific plant species, the specific but not conserved amino acid is substituted by another amino acid than naturally occurring at that place in this group of particular plant species, in this particular plant genus or in this particular plant species in the endogenously coded native CENH3 protein of said plant species. Furthermore, an unspecified amino acid as well as a specified amino acid can be essential with respect to processes of protein folding or protein stability. The alteration of such amino acid can lead to a mutant CENH3 having impaired stability or an incorrect folding.

Specified amino acids given in Table 1 and in Table 2 and in particular specified amino acids of SEQ ID Nos. 49 and 1 are those which occur in a broad range of plant species, preferably such as listed below, and which are thus well conserved.

In a preferred embodiment, the consensus sequence of SEQ ID No. 49 or 1 has been compiled from the sequences of loop1 and α2-helix derived from species selected from the group consisting of Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Secale cereale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria subsp. sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Astragalus sinicus, Lotus

*japonicas, Torenia fournieri, Allium cepa, Allium fistulosum, Allium sativum,* and *Allium tuberosum*.

In a particularly preferred embodiment, the mutation causes a substitution or deletion of a specified amino acid as defined in Table 1 or Table 2. Thus, the plant according to the present invention comprises at least one substitution or deletion of the specified amino acids as defined in Table 1 or Table 2, i.e. those amino acids which are conserved and named in Table 1 or Table 2.

The substitution or deletion of a specified amino acid as defined in Table 1 shall mean the substitution or deletion of an amino acid selected from the group consisting of:
a) threonine, serine or alanine at position 1,
b) histidine, glutamine, asparagine, alanine, tyrosine, phenylalanine, glycine, aspartic acid or glutamic acid at position 2,
c) methionine, glutamine, isoleucine, phenylalanine, tyrosine, alanine, glutamic acid, asparagine, arginine, leucine, histidine or glycine at position 3,
d) leucine, phenylalanine, valine, isoleucine or tyrosine at position 4,
e) alanine, threonine, serine, cysteine or methionine at position 5,
f) proline, asparagine, aspartic acid, arginine, alanine, threonine, phenylalanine, arginine, histidine, serine or lysine at position 6,
g) glutamine, tyrosine, aspartic acid, lysine, arginine, glutamic acid, glycine, serine, proline, histidine, asparagine or alanine at position 8,
h) isoleucine, valine or proline at position 9,
i) asparagine, glycine, threonine, glutamic acid or serine at position 10,
j) arginine or proline at position 11,
k) tryptophan or tyrosine at position 12, and
l) threonine, glutamine or serine at position 13.

The substitution or deletion of a specified amino acid as defined in Table 2 shall mean the substitution or deletion of an amino acid selected from the group consisting of:
a) alanine, proline, valine or leucine at position 1,
b) glutamic acid, aspartic acid, glutamine, histidine or leucine at position 2,
c) alanine at position 3,
d) leucine or valine at position 4,
e) valine, leucine, methionine, isoleucine, arginine, tyrosine or threonine at position 5,
f) serine or alanine at position 6,
g) isoleucine or leucine at position 7,
h) glutamine at position 8,
i) glutamic acid at position 9,
j) alanine or serine at position 10,
k) alanine or threonine at position 11,
l) glutamic acid at position 12,
m) aspartic acid, asparagine, phenylalanine, isoleucine or tyrosine at position 13,
n) tyrosine, phenylalanine or histidine at position 14,
o) leucine, isoleucine or valine at position 15,
p) valine or isoleucine at position 16,
q) glycine, arginine, glutamic acid, histidine, asparagine, threonine, glutamic acid, aspartic acid or glutamine at position 17,
r) leucine, methionine or isoleucine at position 18,
s) phenylalanine, methionine or leucine at position 19,
t) serine, glutamic acid, aspartic acid or glycine at position 20,
u) aspartic acid, methionine, valine, asparagine, glutamic acid, alanine, arginine, lysine at position 21,
v) serine, glycine, alanine or threonine at position 22,
w) methionine, tryptophan, asparagine or histidine at position 23,
x) leucine or histidine at position 24,
y) cysteine or leucine at position 25,
z) alanine or threonine at position 26,
aa) leucine or isoleucine at position 27,
bb) histidine at position 28, and
cc) alanine or serine at position 29.

In a particularly preferred embodiment, the at least one mutation causes a substitution or deletion of a specified amino acid of SEQ ID No. 49. Thus, the plant according to the present invention comprises at least one substitution or deletion of the specified amino acids of SEQ ID No. 49, i.e. those amino acids which are highly conserved and named in the consensus sequence of SEQ ID No. 49. The substitution or deletion of a specified amino acid of SEQ ID No. 49 shall mean the substitution or deletion of an amino acid selected from group consisting of:
a) threonine at position 1,
b) asparagine at position 2,
c) phenylalanine at position 3,
d) leucine at position 4,
e) alanine at position 5,
f) proline at position 6,
g) glutamic acid at position 8,
h) valine at position 9,
i) threonine at position 10,
j) arginine at position 11,
k) tryptophan at position 12, and
l) threonine at position 13.

In a particularly preferred embodiment, the mutation causes a substitution or deletion of a specified amino acid of SEQ ID No. 1. Thus, the plant according to the present invention comprises at least one substitution or deletion of the specified amino acids of SEQ ID No. 1, i.e. those amino acids which are highly conserved and named in the consensus sequence of SEQ ID No. 1. The substitution or deletion of a specified amino acid of SEQ ID No. 1 shall mean the substitution or deletion of an amino acid selected from group consisting of:
a) alanine at position 1,
b) glutamic acid at position 2,
c) alanine at position 3,
d) leucine at position 4,
e) leucine at position 5,
f) alanine at position 6,
g) leucine at position 7,
h) glutamine at position 8,
i) glutamic acid at position 9,
j) alanine at position 10,
k) alanine at position 11,
l) glutamic acid at position 12,
m) aspartic acid at position 13,
n) phenylalanine at position 14,
o) leucine at position 15,
p) valine at position 16,
q) histidine at position 17,
r) leucine at position 18,
s) phenylalanine at position 19,
t) glutamic acid at position 20,
u) aspartic acid at position 21,
v) alanine at position 22,
w) methionine at position 23,
x) leucine at position 24,
y) cysteine at position 25,
z) alanine at position 26,
aa) isoleucine at position 27, bb) histidine at position 28, and
cc) alanine at position 29.

In a further particularly preferred embodiment, the mutation causes a substitution or deletion of a specified amino acid in the loop1, wherein the amino acid asparagine at position 2 of SEQ ID No. 49 is substituted, preferably for valine, or the amino acid alanine at position 95 of SEQ ID No. 55 is substituted, preferably for valine, or the amino acid proline at position 6 of SEQ ID No. 49 is substituted, preferably for serine, or the amino acid proline at position 121 of SEQ ID No. 52 is substituted, preferably for serine, or the amino acid tryptophan at position 12 of SEQ ID No. 49 is substituted, preferably for a stop signal, or the amino acid tryptophan at position 127 of SEQ ID No. 52 is substituted, preferably for a stop signal.

In a further particularly preferred embodiment, the mutation causes a substitution or deletion of a specified amino acid in the α2-helix, wherein the amino acid alanine at position 1 of SEQ ID No. 1 is substituted, preferably for threonine, or the amino acid alanine at position 107 of SEQ ID No. 58 is substituted, preferably for threonine, or the amino acid leucine at position 4 of SEQ ID No. 1 is substituted, preferably for phenylalanine, isoleucine or glutamine, or the amino acid leucine at position 132 of SEQ ID No. 52 or position 92 of SEQ ID No. 34 or position 130 of SEQ ID No. 38 or position 106 of SEQ ID No. 61 is substituted, preferably for phenylalanine, isoleucine or glutamine, or the amino leucine at position 7 of SEQ ID No. 1 is substituted, preferably for proline, or the amino acid leucine at position 109 of SEQ ID No. 61 is substituted, preferably for proline, or the amino acid glutamine at position 8 of SEQ ID No. 1 is substituted, preferably for a stop signal or leucine, or the amino acid glutamine at position 114 of SEQ ID No. 58 or position 110 of SEQ ID No. 61 is substituted, preferably for a stop signal or leucine, or the amino acid alanine at position 10 of SEQ ID No. 1 is substituted, preferably for threonine, or the amino acid alanine at position 138 of SEQ ID No. 52 is substituted, preferably for threonine, or the amino acid cysteine at position 25 of SEQ ID No. 1 is substituted, preferably for tyrosine, or the amino acid cysteine at position 153 of SEQ ID No. 52 is substituted, preferably for tyrosine, or the amino acid alanine at position 26 of SEQ ID No. 1 is substituted, preferably for valine, or the amino acid alanine at position 154 of SEQ ID No. 52 is substituted, preferably for valine.

In the context of the present invention the term 'a mutation' refers to at least one mutation, preferably one mutation, in particular solely one mutation. In a further preferred embodiment, the term 'at least one mutation' refers to two mutations, in particular solely two mutations. In a further preferred embodiment, the term 'at least one mutation' refers to three mutations, in particular solely three mutations. In a further preferred embodiment, the term 'at least one mutation' refers to four mutations, in particular solely four mutations. In a further preferred embodiment, the term 'at least one mutation' refers to five mutations, in particular solely five mutations. In case of more than one mutation, mutations can occur also in different polynucleotides and causes alteration of the amino acid sequences in the CATD domain of different CENH3 proteins if existing for the specific plant species. For example, *Hordeum vulgare* have two different CENH3 proteins.

In a preferred embodiment of the present invention, the mutation is at least one mutation, is at least two mutations, is at least three mutations, is at least four mutations or is at least five mutations.

In a preferred embodiment of the present invention, the maximum number of mutations is two, three, four, five, six, seven, eight, nine and, most preferably, ten.

In a furthermore preferred embodiment, in the CATD domain, preferably in the loop1 or the α2-helix of the CATD domain, one amino acid substitution, in particular solely one amino acid substitution, is present.

In a furthermore preferred embodiment, in the CATD domain, preferably in the loop1 or the α2-helix of the CATD domain, two amino acid substitutions, in particular solely two amino acid substitutions, are present.

In a furthermore preferred embodiment, in the CATD domain, preferably in the loop1 or the α2-helix of the CATD domain, three amino acid substitutions, in particular solely three amino acid substitutions, are present.

In a furthermore preferred embodiment, in the CATD domain, preferably in the loop1 or the α2-helix of the CATD domain, four amino acid substitutions, in particular solely four amino acid substitutions, are present.

In a furthermore preferred embodiment, in the CATD domain, preferably in the loop1 or the α2-helix of the CATD domain, five amino acid substitutions, in particular solely five amino acid substitutions, are present.

In a preferred embodiment of the present invention, in the CATD domain, in particular in the loop1 or the α2-helix of the CATD domain, 1, 1 or 2, 1 to 3, 1 to 4, 1 to 5, preferably 1 to 6, and more preferably 1 to 7 amino acid substitutions are present.

In particular, the present invention is concerned with mutations that cause or lead to an amino acid substitution within the CENH3 protein, in particular the CATD domain thereof. Thus, in the context of the present invention, a mutation preferably is a non-synonymous point mutation or substitution in the DNA sequence encoding the CENH3 protein resulting in a change in amino acid. This is also called a missense mutation. Further, the change in amino acid or the amino acid substitution may be conservative, i.e. a change to an amino acid with similar physiochemical properties, semi-conservative, e.g. negative to positively charged amino acid, or radical, i.e. a change to a vastly different amino acid.

In a preferred embodiment of the present invention, the present plant having biological activity of a haploid inducer is homozygous with respect to the mutation or at least one mutation. In a further embodiment of the present invention, the present plant having biological activity of a haploid inducer is heterozygous with respect to the mutation or at least one mutation.

The plant according to the present invention has the biological activity of a haploid inducer. This means that crossing between the plant according to the present invention and a wildtype plant or a plant expressing wildtype CENH3 protein yields at least 0.1%, 0.2%, 0.3%, 0.4%, 0.5%, 0.6%, 0.7%, 0.8%, 0.9%, preferably at least 1%, preferably at least 2%, preferably at least 3%, preferably at least 4%, preferably at least 5%, preferably at least 6%, preferably at least 7%, preferably at least 8%, preferably at least 9%, most preferred at least 10%, at least 15%, at least 20% or more haploid progeny. Thereby, a wildtype plant is preferably a plant of the same species which does not comprise the mutation of the plant according to the present invention within the corresponding endogenous CENH3 gene, i.e. the plant is able to express the native CENH3 protein, and a plant expressing wildtype CENH3 is preferably a plant of the same species which comprises i) a nucleotide sequence encoding the CENH3 protein without the mutation of the plant according to the present invention and is able to express said native CENH3 protein or ii) a nucleotide sequence encoding a CENH3 protein from another plant species that shows a comparable functionality to the native CENH3, for instance, such CENH3 protein derived from another plant species can be introduced as a transgene.

Thus, the present invention most advantageously provides means and methods to generate haploid inducer lines in a wide range of eudicot, dicot and monocot species. The present invention also allows the exchange of maternal cytoplasm and to create for instance cytoplasmic male sterility plants with a desired genotype in a single process step. The present invention is advantageous insofar as a single amino acid mutation can be generated by mutagenesis or any other non-GMO-based approaches.

Thus, the entire process of haploidization via application of a haploid inducer line characterized by a point mutated endogenous CENH3 gene encoding a CENH3 protein with alteration at at least one of the positions provided by the present invention is non-transgenic in a preferred embodiment.

In the context of the present invention, an "endogenous" gene, allele or protein refers to a non-recombinant sequence of a plant as the sequence occurs in the respective plant, in particular wildtype plant. The term "mutated" refers to a human-altered sequence. Examples of human-induced non-transgenic mutation include exposure of a plant to a high dose of chemical, radiological, or other mutagen for the purposes of selecting mutants. Alternatively, human-induced transgenic mutations, i.e. recombinant alterations or genomic engineering for example by means of TALE nucleases, zinc-finger nucleases or a CRISPR/Cas system, include fusions, insertions, deletions, and/or changes to the DNA or amino acid sequence.

A polynucleotide or polypeptide sequence is "heterologous or exogenous to" an organism if it originates from a foreign species, or, if from the same species, is modified from its original form. "Recombinant" refers to a human-altered, i.e. transgenic polynucleotide or polypeptide sequence. A "transgene" is used as the term is understood in the art and refers to a, preferably heterologous, nucleic acid introduced into a cell by human molecular manipulation of the cell's genome, e.g. by molecular transformation. Thus, a "transgenic plant" is a plant comprising a transgene, i.e. is a genetically-modified plant. The transgenic plant can be the initial plant into which the transgene was introduced as well as progeny thereof whose genome contains the transgene as well.

The term 'nucleotide sequence encoding' refers to a nucleic acid which directs the expression of a specific protein, in particular the CENH3 protein or parts thereof. The nucleotide sequences include both the DNA strand sequence that is transcribed into RNA and the RNA sequence that is translated into the protein. The nucleotide sequences include both the full length nucleic acid sequences as well as non-full length sequences derived from the full length sequences.

The term 'gene' refers to a coding nucleotide sequence and associated regulatory nucleotide sequences, intron(s), 5' UTR and/or 3' UTR.

The term 'regulatory element' refers to a sequence, preferably a nucleotide sequence, located upstream (5'), within and/or downstream (3') to a nucleotide sequence, preferably a coding sequence, whose transcription and expression is controlled by the regulatory element, potentially in conjunction with the protein biosynthetic apparatus of the cell. 'Regulation' or 'regulate' refer to the modulation of the gene expression induced by DNA sequence elements located primarily, but not exclusively upstream (5') from the transcription start of the gene of interest. Regulation may result in an all or none response to a stimulation, or it may result in variations in the level of gene expression.

A regulatory element, in particular DNA sequence, such as a promoter is said to be "operably linked to" or "associated with" a DNA sequence that codes for a RNA or a protein, if the two sequences are situated and orientated such that the regulatory DNA sequence effects expression of the coding DNA sequence.

A 'promoter' is a DNA sequence initiating transcription of an associated DNA sequence, in particular being located upstream (5') from the start of transcription and being involved in recognition and being of the RNA-polymerase. Depending on the specific promoter region it may also include elements that act as regulators of gene expression such as activators, enhancers, and/or repressors.

A '3' regulatory element' (or '3' end') refers to that portion of a gene comprising a DNA segment, excluding the 5' sequence which drives the initiation of transcription and the structural portion of the gene, that determines the correct termination site and contains a polyadenylation signal and any other regulatory signals capable of effecting messenger RNA (mRNA) processing or gene expression. The polyadenylation signal is usually characterised by effecting the addition of polyadenylic acid tracts to the 3' end of the mRNA precursor. Polyadenylation signals are often recognised by the presence of homology to the canonical form 5'-AATAAA-3'.

The term 'coding sequence' refers to that portion of a gene encoding a protein, polypeptide, or a portion thereof, and excluding the regulatory sequences which drive the initiation or termination of transcription.

The gene, coding sequence or the regulatory element may be one normally found in the cell, in which case it is called 'autologous' or 'endogenous', or it may be one not normally found in a cellular location, in which case it is termed 'heterologous', 'transgenic' or 'transgene'.

A 'heterologous' gene, coding sequence or regulatory element may also be autologous to the cell but is, however, arranged in an order and/or orientation or in a genomic position or environment not normally found or occurring in the cell in which it is transferred.

The term 'vector' refers to a recombinant DNA construct which may be a plasmid, virus, autonomously replicating sequence, an artificial chromosome, such as the bacterial artificial chromosome BAC, phage or other nucleotide sequence, in which at least two nucleotide sequences, at least one of which is a nucleic acid molecule of the present invention, have been joined or recombined. A vector may be linear or circular. A vector may be composed of a single or double stranded DNA or RNA.

The term 'expression' refers to the transcription and/or translation of an endogenous gene or a transgene in plants.

'Transformation', 'transforming' and 'transferring' refers to methods to transfer nucleic acid molecules, in particular DNA, into cells including, but not limited to, biolistic approaches such as particle bombardment, microinjection, permeabilising the cell membrane with various physical, for instance electroporation, or chemical treatments, for instance polyethylene glycol or PEG, treatments; the fusion of protoplasts or *Agrobacterium tumefaciens* or *rhizogenes* mediated trans-formation. For the injection and electroporation of DNA in plant cells there are no specific requirements for the plasmids used. Plasmids such as pUC derivatives can be used. If whole plants are to be regenerated from such transformed cells, the use of a selectable marker is preferred. Depending upon the method for the introduction of desired genes into the plant cell, further DNA sequences may be necessary; if, for example, the Ti or Ri plasmid is used for the transformation of the plant cell, at least the right border, often, however, the right and left border of the Ti and Ri plasmid T-DNA have to be linked as flanking region to the genes to be introduced. Preferably, the transferred nucleic acid molecules are stably integrated in the genome or plastome of the recipient plant.

In the context of the present invention the term 'biological activity of a haploid inducer' or 'haploid inducer' or 'haploid inducer line' refers to a plant or plant line having the capability to produce haploid progeny or offspring in at least 0.1%, at least 0.2%, 0.3%, 0.4%, 0.5%, 0.6%, 0.7%, 0.8%, 0.9%, preferably at least 1%, preferably at least 2%, preferably at least 3%, preferably at least 4%, preferably at least 5%, preferably at least 6%, preferably at least 7%, preferably at least 8%, preferably at least 9%, most preferred at least 10%, most preferred at least 15%, most preferred at least 20% of cases when crossed to a wildtype plant or a plant at least expressing wildtype CENH3 protein. Since the chromosomes of the haploid inducer are eliminated during meiosis the resulting haploid progeny only comprises the chromosomes of the wildtype parent. However, in case the haploid inducer was the ovule parent of the cross, the haploid progeny possesses the cytoplasm of the inducer and the chromosomes of the wildtype parent.

The term 'plant' according to the present invention includes whole plants or parts of such a whole plant.

Whole plants preferably are seed plants, or a crop. Parts of a plant are e.g. shoot vegetative organs/structures, e.g., leaves, stems and tubers; roots, flowers and floral organs/structures, e.g. bracts, sepals, petals, stamens, carpels, anthers and ovules; seed, including embryo, endosperm, and seed coat; fruit and the mature ovary; plant tissue, e.g. vascular tissue, ground tissue, and the like; and cells, e.g. guard cells, egg cells, trichomes and the like; and progeny of the same.

In any case, the plant of the present invention comprises at least one cell comprising a nucleotide sequence encoding a centromere histone H3 protein comprising a CATD domain, wherein the nucleotide sequence comprises a mutation causing in the CATD domain an alteration of the amino acid sequence of the CENH3 protein and said alteration can confer the biological activity of a haploid inducer to the plant, preferably as specified herein in more detail. Most preferably, most or in particular all cells of the plant of the present invention comprises the mutation as described herein.

The species of plants that can be used in the method of the invention are preferably eudicot, dicot and monocot plants.

The term 'plant' in a preferred embodiment relates solely to a whole plant, i.e. a plant exhibiting the full phenotype of a developed plant and capable of reproduction, a developmental earlier stage thereof, e.g. a plant embryo, or to both.

In an embodiment of the present invention the term 'plant' refers to a part of a whole plant, in particular plant material, plant cells or plant cell cultures.

The term 'plant cell' describes the structural and physiological unit of the plant, and comprises a protoplast and a cell wall. The plant cell may be in form of an isolated single cell, such as a stomatal guard cells or a cultured cell, or as a part of a higher organized unit such as, for example, a plant tissue, or a plant organ.

The term 'plant material' includes plant parts, in particular plant cells, plant tissue, in particular plant propagation material, preferably leaves, stems, roots, emerged radicles, flowers or flower parts, petals, fruits, pollen, pollen tubes, anther filaments, ovules, embryo sacs, egg cells, ovaries, zygotes, embryos, zygotic embryos per se, somatic embryos, hypocotyl sections, apical meristems, vascular bundles, pericycles, seeds, roots, cuttings, cell or tissue cultures, or any other part or product of a plant.

Thus, the present invention also provides plant propagation material of the plants of the present invention. Said "plant propagation material" is understood to be any plant material that may be propagated sexually or asexually in vivo or in vitro. Particularly preferred within the scope of the present invention are protoplasts, cells, calli, tissues, organs, seeds, embryos, pollen, egg cells, zygotes, together with any other propagating material obtained from transgenic plants. Parts of plants, such as for example flowers, stems, fruits, leaves, roots originating in mutated plants or their progeny previously mutated, preferably transformed, by means of the methods of the present invention and therefore consisting at least in part of mutated cells, are also an object of the present invention.

Preferably, the plant according to the present invention is selected from the group consisting of barley (*Hordeum vulgare*), sorghum (*Sorghum bicolor*), rye (*Secale cereale*), Triticale, sugar cane (*Saccharum officinarium*), maize (*Zea mays*), foxtail millet (*Setaria italic*), rice (*Oryza sativa*), *Oryza minuta*, *Oryza australiensis*, *Oryza alta*, wheat (*Triticum aestivum*), *Triticum durum*, *Hordeum bulbosum*, purple false brome (*Brachypodium distachyon*), sea barley (*Hordeum marinum*), goat grass (*Aegilops tauschii*), apple (*Malus domestica*), *Beta vulgaris*, sunflower (*Helianthus annuus*), Australian carrot (*Daucus glochidiatus*), American wild carrot (*Daucus pusillus*), *Daucus muricatus*, carrot (*Daucus carota*), eucalyptus (*Eucalyptus grandis*), *Erythranthe guttata*, *Genlisea aurea*, woodland tobacco (*Nicotiana sylvestris*), tobacco (*Nicotiana tabacum*), *Nicotiana tomentosiformis*, tomato (*Solanum lycopersicum*), potato (*Solanum tuberosum*), coffee (*Coffea canephora*), grape vine (*Vitis vinifera*), cucumber (*Cucumis sativus*), mulberry (*Morus notabilis*), thale cress (*Arabidopsis thaliana*), *Arabidopsis lyrata*, sand rockcress (*Arabidopsis arenosa*), *Crucihinlalaya himalaica*, *Crucihimalaya wallichii*, wavy bittercress (*Cardamine flexuosa*), peppergrass (*Lepidium virginicum*), sheperd's-purse (*Capsella bursa-pastoris*), *Olmarabidopsis pumila*, hairy rockcress (*Arabis hirsuta*), rape (*Brassica napus*), broccoli (*Brassica oleracea*), *Brassica rapa*, *Brassica juncacea*, black mustard (*Brassica nigra*), radish (*Raphanus sativus*), *Eruca vesicaria sativa*, orange (*Citrus sinensis*), *Jatropha curcas*, *Glycine max*, and black cottonwood (*Populus trichocarpa*).

Particularly preferred the plant is selected from the group consisting of barley (*Hordeum vulgare*), sorghum (*Sorghum bicolor*), rye (*Secale cereale*), Triticale, sugar cane (*Saccharum officinarium*), maize (*Zea mays*), rice (*Oryza sativa*), wheat (*Triticum aestivum*), *Triticum durum*, *Avena sativa*, *Hordeum bulbosum*, *Beta vulgaris*, sunflower (*Helianthus annuus*), carrot (*Daucus carota*), tobacco (*Nicotiana tabacum*), tomato (*Solanum lycopersicum*), potato (*Solanum tuberosum*), coffee (*Coffea canephora*), grape vine (*Vitis vinifera*), cucumber (*Cucumis sativus*), thale cress (*Arabidopsis thaliana*), rape (*Brassica napus*), broccoli (*Brassica oleracea*), *Brassica rapa*, *Brassica juncacea*, black mustard (*Brassica nigra*), radish (*Raphanus sativus*), and *Glycine max*.

The plant according to the present invention contains in a preferred embodiment the nucleotide sequence encoding the CENH3 either as an endogenous gene or a transgene.

The invention relates in a preferred embodiment to a plant according to the present teaching, wherein the alteration is introduced into the nucleotide sequence encoding CENH3 non-transgenically or transgenically.

Thus, preferably in an embodiment, wherein the mutation is effected in the endogenous CENH3 gene, the obtained plant is non-transgenic. Preferably, the mutation is effected via non-transgenic mutagenesis, in particular chemical mutagenesis, preferably via EMS (ethylmethane sulfonate)-induced TILLING or targeted genome editing.

Thus, the present invention relates to a plant, wherein the non-transgenic introduction of the mutation causing in the CATD domain an alteration of the amino acid sequence of the CENH3 protein, preferably an amino acid substitution or deletion, and said alteration confers the biological activity of a haploid inducer is effected via chemical mutagenesis, in particular via TILLING.

In another preferred embodiment, the mutation is introduced into the plant in form of a transgene. Preferably, this is done by transforming a vector comprising a nucleotide sequence encoding at least the CATD domain of CENH3 comprising an alteration, preferably such as described herein. Methods for transformation of a plant and introducing a transgene into the genome of a plant are well-known in the prior art.

Thus, in a preferred embodiment a plant is provided, wherein the transgenic introduction of the alteration, preferably the amino acid substitution or amino substitutions or deletion or deletions, within the CENH3 protein is effected via transformation of a vector comprising a nucleotide sequence encoding at least the loop1 being positioned in the CATD domain and corresponding to nucleotides from position 340 to position 378 of the CENH3 protein as set forth in SEQ ID No. 38 derived from *Arabidopsis thaliana* but comprising at least one amino acid substitution or deletion of one of the specified amino acids of consensus sequence SEQ ID No. 49 or as defined in Table 1, or encoding at least the α2-helix being positioned in the CATD domain and corresponding to nucleotides from position 379 to position 465 of the CENH3 protein as set forth in SEQ ID No. 38 derived from *Arabidopsis thaliana* but comprising at least one amino acid substitution of one of the specified amino acids of consensus sequence SEQ ID No. 1 or as defined in Table 2. In another embodiment a plant is provided, wherein the introduction of the amino acid substitution(s) or deletion(s) within the CENH3 protein is effected via transformation of a vector comprising a nucleotide sequence encoding at least the CATD domain or a CENH3 protein comprising the CATD domain comprising at least one amino acid substitution or deletion of one of the specified amino acids of consensus sequence SEQ ID No. 49 or 1 or as defined in Table 1 or 2.

Preferably, the *Agrobacterium* mediated transformation, floral dip method or particle bombardment are used for transformation.

In the preferred embodiment, wherein the nucleotide sequence encoding the mutated CENH3 protein according to the present invention is transformed into the plant in form of a transgene and one or two alleles of the endogenous CENH3 gene are preferably inactivated or knocked out. Another preferred embodiment, wherein the nucleotide sequence encoding the mutated CENH3 protein according to the present invention is transformed into the plant in form of a transgene and the transgene is overexpressed in order to be more competitive as the endogenous CENH3 protein and preferred during generation of a kinetochore complex.

The present invention also provides a plant obtainable, in particular obtained, by a method according to the present invention and which is characterized by having the biological activity of a haploid inducer.

In a preferred embodiment of the present invention, the method of producing the plant having biological activity of a haploid inducer according to the present invention is not an essentially biological method.

Further, the present invention also provides a method of generating the plant having biological activity of a haploid inducer according to the present invention, comprising the steps of:
   i) subjecting seeds of a plant to a sufficient amount of the mutagen ethylmethane sulfonate (EMS) to obtain M1 plants,
   ii) allowing sufficient production of fertile M2 plants,
   iii) isolating genomic DNA of M2 plants and
   iv) selecting individuals possessing a mutation causing an alteration of the amino acid sequence in the CATD domain of CENH3.

The present invention further relates in a preferred embodiment to a method of generating a plant having biological activity of a haploid inducer according to the present invention, comprising the steps of:
   xx) providing a vector comprising a nucleotide sequence encoding at least the CATD domain of a CENH3 protein comprising a mutation causing in the CATD domain an alteration of the amino acid sequence of the CENH3 protein,
   yy) transforming a plant cell with the vector, wherein preferably the plant cell comprising one or two endogenous alleles of a CENH3 gene inactivated or knocked out, and
   zz) regenerating a plant having the biological activity of a haploid inducer from the plant cell.

The present invention further relates in a preferred embodiment to a method of generating a plant having biological activity of a haploid inducer according to the present invention, comprising the steps of:
   yy) transforming a plant cell with a nucleotide sequence encoding at least the CATD domain of a CENH3 protein comprising a mutation causing in the CATD domain an alteration of the amino acid sequence of the CENH3 protein or a vector comprising a nucleotide sequence encoding at least the CATD domain of a CENH3 protein comprising a mutation causing in the CATD domain an amino an alteration of the amino acid sequence of the CENH3 protein, and
   zz) regenerating a plant having the biological activity of a haploid inducer from the plant cell.

In particular, the present invention relates to a haploid plant, obtainable, in particular obtained, by:
   a) a cross of a plant having the biological activity of a haploid inducer according to the present invention with a plant expressing wildtype CENH3 protein and optionally
   b) identifying haploid progeny generated from the crossing step.

Preferably, the identified haploid plant can be converted into a double haploid plant, preferably via colchicine treatment, which is also part of the present invention. Thus, the present invention also relates to a double-haploid plant, obtainable, in particular obtained, by converting the haploid plant according to the present invention into a double haploid plant, preferably via colchicine treatment or via spontaneous chromosome doubling.

Thus, the present invention provides also a method of generating a haploid plant, comprising the steps of:
a) crossing a plant having the biological activity of a haploid inducer according to the present invention to a plant expressing wildtype CENH3 protein and
b) identifying haploid progeny generated from the crossing step.

In a further step c) the selected haploid plant is preferably converted into a double haploid plant, preferably via colchicine treatment. Thus, the invention relates also to a method of generating a double haploid plant.

In a preferred embodiment of the present invention, the method provided is not an essentially biological method.

In particular, the present methods do not rely solely on, in particular do not consist of, natural phenomena such as crossing or selection, but in fact are essentially based on the technical teaching so as to provide a specifically mutated nucleotide sequence prepared by mankind's contribution. Thus, the present invention introduces a specific structural feature, namely a mutation, into a nucleotide sequence and a plant of the present invention, which mutation is not caused by or associated with any natural phenomena such as crossing or selection.

In a particular embodiment of the present invention, which provides a method including a crossing step, said crossing step does not provide—such as a crossing usually does—heterozygous progeny but in fact homozygous progeny. Furthermore, the haploidy of progeny is not the result of the mixing of genes of the plants used for sexual crossing. Furthermore, the presently claimed process of generating a double haploid plant cannot be found in nature.

Further, the present invention also provides a method of facilitating a cytoplasm exchange, comprising the steps of:
x) crossing a plant according to the present invention as ovule parent to a plant expressing wildtype CENH3 protein as pollen parent, and
y) obtaining a haploid progeny plant comprising the chromosomes of the pollen parent and the cytoplasm of ovule parent.

In a preferred embodiment of the present invention, the method provided is not an essentially biological method. Said method is not a biological method essentially for the same reasons as indicated above, in particular since it is not entirely made up of natural phenomena such as crossing and selection, but involves as an essential feature a significant technical teaching so as to provide a particular mutation in a nucleotide sequence and a plant of the present invention. Furthermore, the haploidy of the progeny is not the result of the mixing of genes of the plants used for sexual crossing.

The method can advantageously be used to create cytoplasmic male sterility (CMS). CMS is caused by the extranuclear genome (mitochondria or chloroplasts) and shows maternal inheritance. Thus, the plant according to the present invention has to exhibit CMS and be the ovule parent of the cross. In this way CMS can be introduced into the crossing partner, preferably being an elite line of a crop.

In a preferred embodiment, the plant according to the present invention can also be used in a method to restore male fertility by providing a normal cytoplasm to a crossing partner that is CMS. Through such a cross the chromosomes of the CMS plant are introduced into the normal cytoplasm of the haploid inducer of the present invention which is not CMS. However, pollen production of the CMS plant has to be induced via temperature, light, length of day etc.

Without being bound by theory a possible model of how the present methods, in particular a method of uniparental chromosome elimination, works in inducer CENH3×wild type CENH3 interspecific hybrid embryos is given in the figure. (A) Likely haploid inducer-derived egg cells contain either less CENH3 or compared to wild type a reduced unknown 'CENH3-transgeneration required signature'. A reduced amount of maternal CENH3 is less likely as according to studies performed with a CENH3-GFP reporter in *A. thaliana* plants sperm nuclei but not eggs cells are marked by CENH3. However, it is still possible that residual maternal CENH3s, generating a 'centromeric imprinting' are transmitted to the progeny. (B) Within a few hours after fertilization also paternal wild type CENH3 is actively removed from the zygote nucleus, and (C) centromeric reloading of CENH3-GFP in the zygote occurs at the 16-nuclei stage of endosperm development in *A. thaliana*. (D) In embryos undergoing haploidization centromeric reloading of the maternal chromosomes is impaired or delayed causing lagging chromosomes because of centromere inactivity during anaphase. Subsequently micronucleated haploid inducer chromosomes will degrade and (E) a haploid embryo will develop. Haploid embryos contain paternal-derived chromosomes in the background of maternal-derived cytoplasm.

The present invention also relates to a nucleotide sequence encoding at least the CATD domain of a CENH3 protein or a CENH3 protein including a CATD domain comprising a mutation causing in the CATD domain anan alteration of the amino acid sequence of the CENH3 protein.

The present invention also relates to a vector, in particular viral vector, construct or plasmid comprising said nucleotide sequence and, if present, associates sequences, preferably as indicated herein.

In a particularly preferred embodiment of the present invention, the nucleotide sequence encoding at least the CATD domain of a CENH3 protein preferably comprises at least the complete coding region of CENH3, in particular the gene of CENH3.

In a furthermore preferred embodiment of the present invention, the coding sequence of the CENH3 may be associated with regulatory elements, such as 5'- and/or 3'-regulatory elements, most preferably with a promoter, preferably a constitutive or inducible promoter.

Further, a plant cell comprising said nucleotide sequence or a vector comprising it as a transgene is provided by the present invention.

In the context of the present invention, the term 'comprising' as used herein is understood as to have the meaning of 'including' or 'containing', which means that in addition to the explicitly mentioned element further elements are possibly present.

In a preferred embodiment of the present invention, the term 'comprising' as used herein is also understood to mean 'consisting of' thereby excluding the presence of other elements besides the explicitly mentioned element.

In a furthermore preferred embodiment, the term 'comprising' as used herein is also understood to mean 'consisting essentially of' thereby excluding the presence of other elements providing a significant contribution to the disclosed teaching besides the explicitly mentioned element.

Further preferred embodiments of the present invention are the subject-matter of the subclaims.

The invention will now be described in some more detail by way of the non-limiting examples and two figures.

The sequence protocol shows:
SEQ ID No.1: the amino acid consensus sequence of the CENH3 α2-helix,
SEQ ID Nos. 2 to 32: nucleotide sequences of primers used in the present teaching, SEQ ID No. 33: the cDNA nucleotide sequence of the wildtype β-CENH3 protein of *Hordeum vulgare*, SEQ ID No. 34: the amino acid sequence of β-CENH3 of *Hordeum vulgare*, SEQ ID No. 35: the cDNA sequence of the β-CENH3 of *Hordeum vulgare* (TILLING line 4528 mutant), SEQ ID No. 36: the amino acid sequence of β-CENH3 of *Hordeum vulgare* (TILLING line 4528 mutant), SEQ ID No. 37: the nucleotide sequence of the wildtype coding sequence (cDNA) of *A. thaliana* CENH3, SEQ ID No. 38: the amino acid sequence of the wildtype *A. thaliana* CENH3, SEQ ID No. 39: the nucleotide sequence of the coding sequence (cDNA) of the mutated *A. thaliana* CENH3 (mutant L to I), SEQ ID No. 40: the amino acid sequence of the mutated *A. thaliana* CENH3 (mutant L to I), SEQ ID No. 41: the nucleotide sequence of the coding sequence (cDNA) of the mutated *A. thaliana* CENH3 (mutant L to F), SEQ ID No. 42: the amino acid sequence of the mutated *A. thaliana* CENH3 (mutant L to F), SEQ ID No. 43: the nucleotide sequence of the wildtype coding sequence (cDNA) of *Beta vulgaris* CENH3, SEQ ID No. 44: the amino acid sequence of the wildtype *Beta vulgaris* CENH3, SEQ ID No. 45: the nucleotide sequence of the coding sequence (cDNA) of *Beta vulgaris* CENH3 (mutant L to F), SEQ ID No. 46: the amino acid sequence of the mutated *Beta vulgaris* CENH3 (mutant L to F), SEQ ID No. 47: the nucleotide sequence of the coding sequence (cDNA) of *Beta vulgaris* CENH3 (mutant L to I), SEQ ID No. 48: the amino acid sequence of the mutated *Beta vulgaris* CENH3 (mutant L to I), SEQ ID No. 49: the amino acid consensus sequence of the CENH3 loop1, SEQ ID No. 50: the nucleotide sequence of the wildtype genomic sequence (genomic DNA) of *B. napus* CENH3, SEQ ID No. 51: the nucleotide sequence of the wildtype coding sequence (cDNA) of *B. napus* CENH3, SEQ ID No. 52: the amino acid sequence of the wildtype *B. napus* CENH3, SEQ ID No. 53: the nucleotide sequence of the wildtype genomic sequence (genomic DNA) of *S. bicolor* CENH3, SEQ ID No. 54: the nucleotide sequence of the wildtype coding sequence (cDNA) of *S. bicolor* CENH3, SEQ ID No. 55: the amino acid sequence of the wildtype *S. bicolor* CENH3, SEQ ID No. 56: the nucleotide sequence of the wildtype genomic sequence (genomic DNA) of *Z. mays* CENH3, SEQ ID No. 57: the nucleotide sequence of the wildtype coding sequence (cDNA) of *Z. mays* CENH3, SEQ ID No. 58: the amino acid sequence of the wildtype *Z. mays* CENH3, SEQ ID No. 59: the nucleotide sequence of the wildtype genomic sequence (genomic DNA) of *B. vulgaris* CENH3, SEQ ID No. 60: the nucleotide sequence of the wildtype coding sequence (cDNA) of *B. vulgaris* CENH3, SEQ ID No. 61: the amino acid sequence of the wildtype *B. vulgaris* CENH3, SEQ ID No. 62: the nucleotide sequence of the genomic sequence (genomic DNA) of mutated *B. napus* CENH3 (mutant P121S), SEQ ID No. 63: the nucleotide sequence of the coding sequence (cDNA) of the mutated *B. napus* CENH3 (mutant P121S), SEQ ID No. 64: the amino acid sequence of the mutated *B. napus* CENH3 (mutant P121S), SEQ ID No. 65: the nucleotide sequence of the genomic sequence (genomic DNA) of mutated. *B. napus* CENH3 (mutant W127stop), SEQ ID No. 66: the nucleotide sequence of the coding sequence (cDNA) of the mutated *B. napus* CENH3 (mutant W127stop), SEQ ID No. 67: the amino acid sequence of the mutated *B. napus* CENH3 (mutant W127stop), SEQ ID No. 68: the nucleotide sequence of the genomic sequence (genomic DNA) of mutated *B. napus* CENH3 (mutant L132F), SEQ ID No. 69: the nucleotide sequence of the coding sequence (cDNA) of the mutated *B. napus* CENH3 (mutant L132F), SEQ ID No. 70: the amino acid sequence of the mutated *B. napus* CENH3 (mutant L132F), SEQ ID No. 71: the nucleotide sequence of the genomic sequence (genomic DNA) of mutated *B. napus* CENH3 (mutant A138T), SEQ ID No. 72: the nucleotide sequence of the coding sequence (cDNA) of the mutated. *B. napus* CENH3 (mutant A138T), SEQ ID No. 73: the amino acid sequence of the mutated *B. napus* CENH3 (mutant A138T), SEQ ID No. 74: the nucleotide sequence of the genomic sequence (genomic DNA) of mutated *B. napus* CENH3 (mutant C153Y), SEQ ID No. 75: the nucleotide sequence of the coding sequence (cDNA) of the mutated *B. napus* CENH3 (mutant C153Y), SEQ ID No. 76: the amino acid sequence of the mutated *B. napus* CENH3 (mutant C153Y), SEQ ID No. 77: the nucleotide sequence of the genomic sequence (genomic DNA) of mutated *B. napus* CENH3 (mutant A154V), SEQ ID No. 78: the nucleotide sequence of the coding sequence (cDNA) of the mutated *B. napus* CENH3 (mutant A154V), SEQ ID No. 79: the amino acid sequence of the mutated *B. napus* CENH3 (mutant A154V), SEQ ID No. 80: the nucleotide sequence of the genomic sequence (genomic DNA) of mutated *Z. mays* CENH3 (mutant A107T), SEQ ID No. 81: the nucleotide sequence of the coding sequence (cDNA) of the mutated *Z. mays* CENH3 (mutant A107T), SEQ ID No. 82: the amino acid sequence of the mutated. *Z. mays* CENH3 (mutant A107T), SEQ ID No. 83: the nucleotide sequence of the genomic sequence (genomic DNA) of mutated *Z. mays* CENH3 (mutant Q114stop), SEQ ID No. 84: the nucleotide sequence of the coding sequence (cDNA) of the mutated *Z. mays* CENH3 (mutant Q114stop), SEQ ID No. 85: the amino acid sequence of the mutated *Z. mays* CENH3 (mutant Q114stop), SEQ ID No. 86: the nucleotide sequence of the genomic sequence (genomic DNA) of mutated *S. bicolor* CENH3 (mutant A95V), SEQ ID No. 87: the nucleotide sequence of the coding sequence (cDNA) of the mutated *S. bicolor* CENH3 (mutant A95V), SEQ ID No. 88: the amino acid sequence of the mutated. *S. bicolor* CENH3 (mutant A95V), SEQ ID No. 89: the nucleotide sequence of the genomic sequence (genomic DNA) of mutated *B. vulgaris* CENH3 (mutant L106Q), SEQ ID No. 90: the nucleotide sequence of the coding sequence (cDNA) of the mutated *B. vulgaris* CENH3 (mutant L106Q), SEQ ID No. 91: the amino acid sequence of the mutated *B. vulgaris* CENH3 (mutant L106Q), SEQ ID No. 92: the nucleotide sequence of the genomic sequence (genomic DNA) of mutated *B. vulgaris* CENH3 (mutant L109P), SEQ ID No. 93: the nucleotide sequence of the coding sequence (cDNA) of the mutated *B. vulgaris* CENH3 (mutant L109P), SEQ ID No. 94: the amino acid sequence of the mutated *B. vulgaris* CENH3 (mutant L109P), SEQ ID No. 95: the nucleotide sequence of the genomic sequence (genomic DNA) of mutated *B. vulgaris* CENH3 (mutant Q110L), SEQ ID No. 96: the nucleotide sequence of the coding sequence (cDNA) of the mutated *B. vulgaris* CENH3 (mutant Q110L), and SEQ ID No. 97: the amino acid sequence of the mutated *B. vulgaris* CENH3 (mutant Q110L).

EXAMPLES

Figure 1:
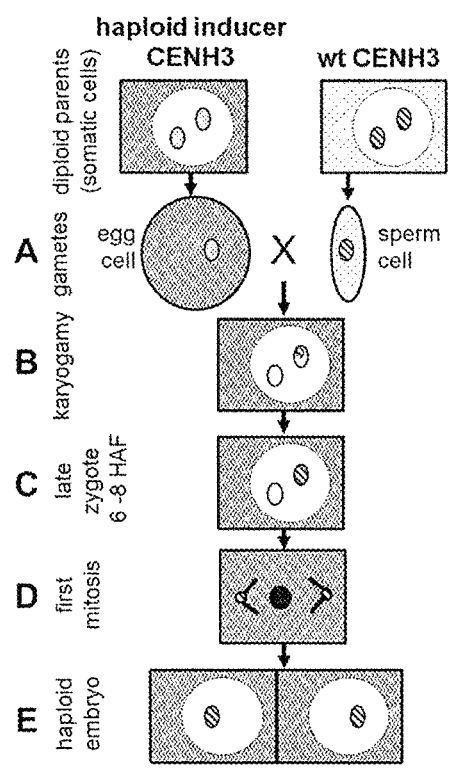
FIG. 1 shows schematically a mechanistic model relating to methods of the present invention.
Figure 1:
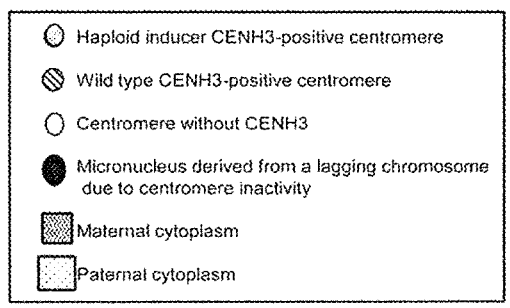
Figure 2:
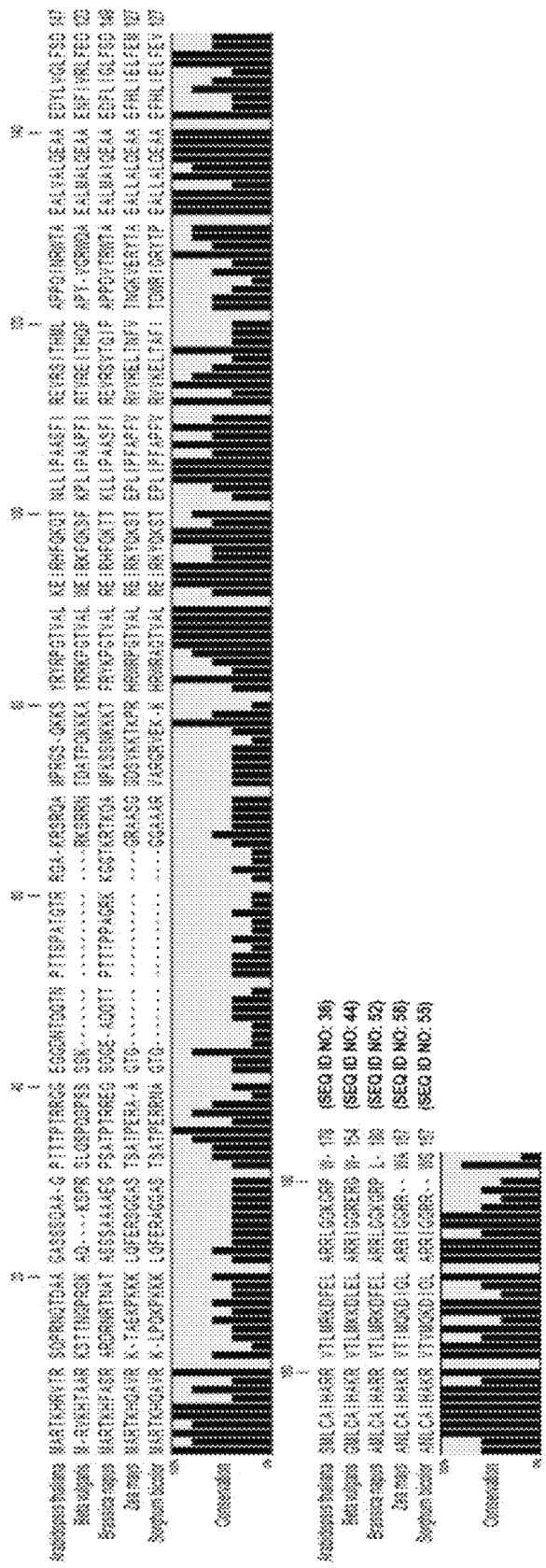
FIG. 2 shows an alignment of the amino acid sequences of *Arabidopsis thaliana* (first row), *Beta vulgaris* (second row), *Brassica napus* (third row), *Zea mays* (forth row), *Sorghum bicolor* (fifth row) as well as a diagram showing the level of conservation over these five plant species.

Example 1: Mutagenesis of Barley α and βCENH3 by Targeting Local Lesions IN Genomes (TILLING)

To identify whether a single point mutation of endogenous CENH3 could result in a haploid inducer an EMS-induced TILLING population of diploid barley (*Hordeum vulgare*) (Gottwald et al., 2 (2009), BMC Res Notes, 258), a species encoding two functional variants of CENH3 (α and βCENH3) (Sanei et al., 108 (2011), Proc Natl Acad Sci USA, E498-505) was screened. Assuming the complementation of either CENH3 variant a functional mutation of αCENH3 or βCENH3 would still allow the generation of offspring.

To do this, a TILLING population of 10,279 EMS treated diploid barley (*Hordeum vulgare*) plants of cv. Barke to identify mutant alleles of α and βCENH3 was screened. Four and three primer combinations

```
Hv_aCENH3_EX1 + 2 + 3_F:
                                        (SEQ ID No. 2)
AGGCAGGGTCTCAATTCCTT,

Hv_aCENH3_EX1 + 2 + 3_R:
                                        (SEQ ID No. 3)
GTCCCATCATCCATCGTCTT,

Hv_aCENH3_EX4 + 5_F:
                                        (SEQ ID No. 4)
CCCACTTCCTTGTTGTGGAC,

Hv_aCENH3_EX4 + 5_R:
                                        (SEQ ID No. 5)
GGCGATAAATGTATCTTGCATTC,

Hv_aCENH3_EX6_F:
                                        (SEQ ID No. 6)
TGGTAGCAACCAGAGCTACG,

Hv_aCENH3_EX6_R:
                                        (SEQ ID No. 7)
ACTGGCATGTTTCCTTCTGC,

Hv_aCENH3_EX7_F:
                                        (SEQ ID No. 8)
CGGACGGAGGGAGTATTTCT,

Hv_aCENH3_EX7_R:
                                        (SEQ ID No. 9)
GGACATGCCCAAAGAAAGTG,

Hv_bCENH3_EX1 + 2_F:
                                        (SEQ ID No. 10)
GCCAGCGAGTACTCCTACAAG,

Hv_bCENH3_EX1_R:
                                        (SEQ ID No. 11)
TTGAGTTACCAGCCACCACTC,

Hv_bCENH3_EX3_F:
                                        (SEQ ID No. 12)
GTCATGCACTGTGTCTTGCA,

Hv_bCENH3_EX3_R:
                                        (SEQ ID No. 13)
TGCTAAGATCGGATAACTGTGG,

Hv_bCENH3_EX4_F:
                                        (SEQ ID No. 14)
TGCTCCTGAACAAACTGAACC,

Hv_bCENH3_EX4_R:
                                        (SEQ ID No. 15)
GTGGCCGTCAGTACAATCG
``` were used to amplify all exons of the α and βCENH3 variants and parts of the corresponding introns, respectively, by using PCR with a heteroduplex step as described earlier (Gottwald et al., (2009), BMC Res Notes, 258). PCR products were digested with dsDNA Cleavage Kit and analysed using Mutation Discovery Kit and Gel-dsDNA reagent kit on the AdvanCE™ FS96 system according to manufacturer's guidelines (Advanced Analytical, IA, USA).

RNA Extraction, PCR and Quantitative Real Time RT-PCR

Total RNA was isolated from roots, leaves using the Trizol method (Chomczynski and Sacchi, 162 (1987), Anal Biochem, 156-159) from anthers (microscopically staged between meiosis and development of mature pollen), carpel, endosperm and embryo by Picopure RNA isolation kit (Arcturus) according to manufacturer. The absence of genomic DNA contamination was confirmed by PCR using GAPDH primers (see Table 3). 10 μl of PCR mixture contained 1 μl of cDNA template, 5 μl of 2× Power SYBR Green PCR Master Mix (Applied Biosystems), 0.33 mM of the forward and reverse primers for each gene (see Table 3). Reactions were run in an Applied Biosystems 7900HT Fast Real-Time PCR System. The PCR was performed using the following conditions: 95° C. for 10 min, followed by 40 cycles at 95° C. for 15 s, at the annealing temperature of 60° C. for 60 s. Three technical replicates were performed for each cDNA sample. Fast Real-Time PCR System and data were analyzed with SDS software v 2.2.2. Transcript levels of each gene were normalized to GAPDH by the following formula: $R=2^{\wedge(-(CtGOI-CtH))*100}$, where R=relative changes, GOI=gene of interest, and H=housekeeping (GAPDH). The specificity and efficiency of both primers were determined by qRT-PCR using a dilution series of plasmids of cloned full length barley α and βCENH3 genes. A similar Ct value (the PCR cycle at which the fluorescent signal of reporter dye exceeds background level) for equal amount of plasmid indicates that both primers can amplify specific transcripts with the same efficiency.

TABLE 3

| Primer name | Sequence (5' to 3') |
|---|---|
| GAPDH-F | CAATGATAGCTGCACCACCAACTG (SEQ ID No. 21) |
| GAPDH-R | CTAGCTGCCCTTCCACCTCTCCA (SEQ ID No. 22) |
| Hvα-F | AGTCGGTCAATTTTCTCATCCC (SEQ ID No. 23) |
| Hvα-R | CTCTGTAGCCTCTTGAACTGC (SEQ ID No. 24) |
| Hvβ-F | GCCATTGTCGAACAAGAAGG (SEQ ID No. 25) |
| Hvβ-R | TAACACGGTGCGAATGAATG (SEQ ID No. 26) |
| CH3A + L130_F_for | phos-GACAGCTGAAGCATTTGTTGCTCTTC (SEQ ID No. 27) |
| CENH3L130_I_for | phos_GACAGCTGAAGCTATTGTTGCTCTTC (SEQ ID No. 28) |
| CENH3L130_F + I_rev | phos-CAACGATTGATTTGGGGAGGG (SEQ ID No. 29) |
| cenh3-1_mut_for | GGTGCGATTTCTCCAGCAGTAAAAATC (SEQ ID No. 30) |
| cenh3-1_mut_rev | CTGAGAAGATGAAGCACCGGCGATAT (SEQ ID No. 31) |
| cenh3-1_mut2429r | AACTTTTGCCATCCTCGTTTCTGTT (SEQ ID No. 32) |

Only missense point mutations were identified for both barley CENH3 variants.

The non-functionality of mutated CENH3s of homozygous M2 mutants was tested by immunostaining of the centromeres with CENH3 variant-specific antibodies. Mitotic and meiotic chromosomes of *H. vulgare* wildtype and homozygous TILLING line 4528 (plant according to the present invention) have been subjected to immunostaining with antibodies specific for αCENH3 and βCENH3. αCENH3 and βCENH3 signals at centromeres were revealed in all mutants, while only the homozygous TILLING line 4528 which contains a leucine to phenylalanine substitution at amino acid 92 (SEQ ID No. 36), i.e. amino acid position 4 of the consensus sequence SEQ ID No. 1, displayed no centromeric βCENH3 signals in mitotic, meiotic and interphase cells. The leucine to phenylalanine substitution at amino acid 92 of SEQ ID No. 36 of the *H. vulgare* β-CENH3 sequence corresponds to a single nucleotide substitution from C to T at position 274 of the *H. vulgare* β-CENH3 cDNA sequence (SEQ ID No. 35).

Only weak dispersed βCENH3 signals outside centromeres were found in this line. Transcription levels of α and βCENH3 in wildtype (cv Barke) (SEQ ID no. 33 and 34) and TILLING line 4528 with mutated βCENH3 have been measured. The relative expression level of α and βCENH3 was measured in different tissues using specific primers (Table 3). cDNA was prepared from total RNA and gene expression levels were normalized to the expression level of glyceryl phosphate dehydrogenase (GRPTA). Obviously, the centromeric loading of the mutated βCENH3 variant seems to be impaired, while no different transcription level between wild type and mutated βCENH3 was found. Hence, centromeres exclusively composed of αCENH3 are sufficient for mitotic centromere function in barley as no obvious chromosome segregation defects, such as anaphase bridges, as well as changes of ploidy or cycle vales was found. In addition, no obvious changes of the plant habitus were observed in mutant plants. In particular, no significant differences in phenotype, ploidy levels, cycle values and growth phenotype between homozygous plants of TILLING line 4528 and barley wildtype could be detected.

The issue was addressed whether missing βCENH3 is compensated by additional αCENH3 to maintain the centromere function in the mutant. Therefore, αCENH3 immunostaining signals of wildtype (126 centromeres measured) and of line 4528 (56 centromeres measured) were comparatively quantified by pixel intensity measurements. An increase of 19.8% αCENH3 in the mutant indicates that the missing βCENH3 is partly compensated by additionally incorporated αCENH3. The βCENH3 mutation is located in an evolutionarily highly conserved targeting domain (CATD) defined by parts of α1 helix, loop 1 and α2 helix of the histone fold. This domain is required for centromere loading of CENH3 by chaperons.

Indirect Immunostaining

Indirect immunostaining of nuclei and chromosomes was carried out as described previously (Sanei et al., 108 (2011), Proc Natl Acad Sci USA, E498-505). CENH3 of barley was detected with guenia pig anti-αCENH3-specific and rabbit anti-βCENH3-specific antibodies. A rabbit HTR12-specific antibody (abcam, ab72001) was used for the detection of *A. thaliana* CENH3 (AtCENH3). Epifluorescence signals were recorded with a cooled CCD-camera (ORCA-ER, Hamamatsu). Imaging was performed by using an Olympus BX61 microscope and an ORCA-ER CCD camera (Hamamatsu). To analyse the structures of immunosignals and chromatin at an optical resolution of ~100 nm (super-resolution) Structured Illumination Microscopy (SIM) was applied using a C-Apo 63×/1.2 W Korr objective of an Elyra microscope system and the software ZEN (Zeiss, Germany). Images were captured separately for each fluorochrome using appropriate excitation and emission filters. The images were merged using the Adobe Photoshop 6.0 software. To determine the amount of α and βCENH3 in nuclei fluorescence intensities were measured using the TINA 2.0 software in maximum intensity projections generated from stacks of optical SIM sections through the specimens by the ZEN software. An intensity threshold was set to computationally subtract the background pixels from the image. The corrected sum of grey values of all signals within the nucleus was used to determine the CENH3 content. 3D-rendering based on SIM image stacks was done using the ZEN software.

Example 2: *Arabidopsis thaliana*

To proof whether the mutation in the CATD domain caused the observed impaired centromere loading, eYFP was N-terminally fused to the coding sequence (CDS) of *A. thaliana* CENH3 (SEQ ID No. 37, protein: SEQ ID No. 38) with an L/I (leucine/isoleucine) (CDS: SEQ ID No. 39, protein SEQ ID No. 40) or L/F (leucine/phenylalanine) (CDS: SEQ ID No. 41, protein SEQ ID No. 42) exchange of the corresponding positions (L130I or L130F, corresponding to amino acid position 92 in βCENH3 of barley, i.e. amino acid position 4 of the consensus sequence SEQ ID No. 1) in *A. thaliana* CENH3. The leucine to isoleucin substitution at position 130 of *A. thaliana* corresponds to a single nucleotide substitution from C to A at position 388 of SEQ ID no. 37.

The amino acid substitution from leucine to phenylalanine at position 130 is caused by two nucleotide substitutions, namely TC to AT at positions 387 and 388 of SEQ ID No. 37.

Double labelling of transgenic *A. thaliana* with corresponding anti-wild type CENH3 and anti-GFP revealed a significantly reduced centromere targeting of the mutated CENH3s.

Next, to test for haploid inducer ability *A. thaliana* genomic CENH3 constructs with a L130I or L130F exchange were used to transform heterozygous CENH3 knock-out *A. thaliana* plants (Ravi and Chan, Nature, 464 (2010), 615-618). Genotyping identified homozygous CENH3 null mutants which were complemented with either genomic CENH3 wild type, L130I or L130F constructs. As viable diploid plants containing either of the constructs were obtained, it is likely that this mutation does not impair the centromere function in homozygous *A. thaliana* plants. When CENH3 null mutants expressing a point mutated L130F CENH3 protein were crossed to wild type, chromosomes from the mutant are eliminated, producing haploid progeny. Flow cytometric analysis revealed that 10.7% of the F1 plants were haploid.

Cloning and Generation of CENH3 Transgenes

To generate CENH3 genomic fragments carrying mutations, resulting in phenylalanine 130 (F130) and isoleucine 130 (I130) instead of wild-type leucine 130 (L130), a genomic CENH3 fragment in pCAMBIA1300 vector used to complement cenh3-1/cenh3-1 (cenh3 null mutant) (Ravi and Chan, Nature, 464 (2010), 615-618; Ravi et al., Genetics, 186 (2010), 461-471) was subcloned via the unique HindIII and BamHI sites into pBlueScript II KS (Strategene, www.stratagene.com). Mutations of CENH3, L130I or L130F, were generated in pBlueScript II KS using a Phusion® Site-Directed Mutagenesis Kit (Finnzymes, www-.finnzymes.com) according to manufacturer's instructions with minor changes as described. Following 5'-phosphorylated primers were used for mutagenesis: CH3A+ L130_F_for, CENH3L130_I_for and CENH3L130_F+ I_rev. Mutated CENH3 genomic fragments were subcloned via the unique HindIII and BamHI sites into the initial pCAMBIA1300 containing a hygromycin resistance marker. All constructs were verified by sequencing. For primers see Table 3, above.

To generate p35S::eYFP-CENH3 fusion constructs containing mutations within the CENH3 CDS, resulting in L130I or L130F, a plasmid (p35S-BM; Schmidt, www.dna-cloning.com) containing a p35S::eYFP-CENH3 expression (Lermontova, 18 (2006), Plant Cell, 615-618) was used as template for the Phusion® Site-Directed Mutagenesis Kit (Finnzymes, www.finnzymes.com). Primers and strategies to introduce desired mutations were the same as above. Resulting expression cassettes (35Spro, eYFP-(mutated) CENH3 and NOS terminator) were subcloned via unique SfiI restriction sites into the pLH7000 vector containing a phosphinotricine resistance marker (Schmidt, www.dna-cloning.com) and verified by sequencing.

Plant Transformation, Culture Conditions and Cross-Pollination

*A. thaliana* wild-type (SEQ ID No. 37 and 38) and cenh3-1/CENH3 heterozygotes plants (both accession Columbia-0) were transformed by the floral dip method (Clough and Bent, 16 (1998), Plant J, 735-743). Transgenic progenies were selected on Murashige and Skoog solid medium containing the corresponding antibiotic. Plants were germinated on Petri dishes under long-day conditions (20° C. 1611 light/18° C. 8 h dark), grown for 4 weeks under short-day conditions (20° C. 8 h light/18° C. 16 h dark) and then shifted to long-day conditions again. For crossing, the closed buds of mutant cenh3 *A. thaliana* were emasculated by removing the immature anthers with the help of forceps. The stigmas of emasculated buds were fertilized with the yellowish pollen from mature anthers of freshly opened wild type *A. thaliana* flowers.

DNA Extraction and Genotyping of *A. thaliana*

Genomic DNA preparations and PCR-based genotyping were performed using standard methods. DNA was extracted according to Edwards et al. (1991), Nucleic Acids Res 19, 1349.

Plants were genotyped for cenh3-1 in a dCAPS genotyping reaction. The dCAPS primers, cenh3-1_mut_for and cenh3-1_mut_rev, were used to amplify CENH3. Amplicons were digested with EcoRV and resolved on a gel. cenh3-1 mutant allele is not cut (215 bp) while the WT CENH3 allele is cut (191 and 24 bp). For primers see Table 3. To genotype the endogenous CENH3 locus for cenh3-1 in the offspring of cenh3-1/CENH3 plants transformed with the CENH3 genomic locus (untagged CENH3 transgene with L130, L130I or L130F), an initial PCR reaction was performed with one primer outside of the transgene CENH3 locus, allowing specific amplification of the endogenous and not the transgenic CENH3 locus. Primers used were cenh3-1mut_for and cenh3-1_mut2320r/cenh3-1_mut2429r. Amplicons were purified and used as template for a second dCAPS PCR genotyping reaction as described above for cenh3-1 plants. For Primers see Table 3. Presence of transgene was verified by PCR.

Flow Cytometric Analysis of Plants and Seeds

For flow cytometric ploidy analyses of plants equal amounts of leaf material of 5 to 10 individuals were chopped simultaneously in nuclei isolation buffer (Galbraith et al. (1983), Science 220, 1049-1051) supplemented with DNas-free RNase (50 µg/ml) and propidium iodide (50 µg/ml) with a sharp razor blade. The nuclei suspensions were filtered through 35 µm cell strainer cap into 5 ml polystyrene tubes (BD Biosciences) and measured on a FACStar$^{PLUS}$ cell sorter (BD Biosciences) equipped with an argon ion laser INNOVA 90C (Coherent). Approximately 10,000 nuclei were measured and analysed using the software CELL Quest ver. 3.3 (BD Biosciences). The resulting histograms were compared to a reference histogram representing a diploid wild type plant. In cases where an additional peak at the haploid position was detected, the plants were individually measured again to identify the haploid individuals.

Nuclei isolation of seeds was performed as described above using the nuclei isolation buffer. MA VI (100 mM Tris-HCl, 5.3 mM $MgCl_2$, 86 mM NaCl, 30.6 mM sodium citrate, 1.45 mM Triton X-100, pH 7.0; supplemented with 50 DNas-free RNase and 50 µg/ml propidium iodide). Nuclei suspensions were measured on a FACSAria cell sorter (BD Biosciences) and analysed using the FACS Diva software ver. 6.1.3 (BD Biosciences). Similarly as above, first 10 to 20 seeds were pooled to identify lines with haploid embryos and in a second step single seeds were co-chopped together with leaf material from *Raphanus sativus* (Genebank Gatersleben, accession number: RA 34) as internal reference to confirm the occurrence of haploid seeds.

Example 3: *Beta vulgaris*

Further, the functional significance of the identified mutation was assayed also in the sugar beet *Beta vulgaris*. RFP reporter constructs containing the cDNA of *Beta vulgaris* CENH3 (SEQ ID No. 43, protein SEQ ID No. 44) with an L106F (SEQ ID No. 45, protein SEQ ID No. 46) or L106I (SEQ ID No. 47, protein SEQ ID No. 48) exchange (corresponding to amino acid position 92 of barley, amino acid position 4 of the consensus sequence SEQ ID No. 1) were generated and used for stable transformation of sugar beet and a reduced centromere targeting of the mutated CENH3s was detected.

The amino acid substitution from leucine to phenylalanine at position 106 is caused by two nucleotide substitutions, namely C to T at position 316 and G to T at position 318 of SEQ ID no. 43.

The amino acid substitution from leucine to isoleucine at position 106 is caused by two nucleotide substitutions, namely C to A at position 316 and G to T at position 318 of SEQ ID no. 43.

Plant Transformation and Culture Conditions

*Beta vulgaris* wild-type leaves of 6-8 week old plants (grown under semi-controlled greenhouse conditions) were transiently transformed by particle bombardment (300 μg gold coated with 0.5 μg plasmid DNA). Bombarded leaves were incubated for 48-72 h (25° C. 16 h light (350 μmolm$^{-2}$s$^{-1}$)/8 h dark) before microscopic analysis. Stable transformation of *B. vulgaris* callus was performed as described in Lindsey & Gallois, 1990 (*Journal of experimental botany*, 41(5), 529-536) (selection via kanamycin). After approx. 2 month (24° C. 16 h light (55 μmolm$^{-2}$s$^{-1}$)/8 h dark) callus cells were microscopically analysed.

Cloning and Generation of CENH3 Transgenes

To generate the 35S::RFP-CENH3 fusion construct, CENH3 was amplified from sugar beet cDNA with the following primers:

```
                              (SEQ ID No. 16)
BvCENH3-cds1:    GGATCCATGAGAGTTAAACACACTGC, (SEQ ID No. 17)
BvCENH3-cds2:    GGATCCTGTTCAGTTACCATCCCCTC,
``` cloned into a vector containing a 35Spro, RFP and 35S-terminator expression cassette For constructs containing mutations within the CENH3 coding sequence, resulting in F106 and I106 instead of L106, the above mentioned plasmid containing the 35S::RFP-CENH3 expression cassette was used as template for primer based mutagenesis. The PstI site close to the position of the desired mutation was used to split CENH3 into two parts. Via mutations in the Primers the desired mutations were integrated:

```
                              (SEQ ID No. 18)
BvCENH3_mut_Fw:    ATGGATCCATGAGAGTTAAACACACTGC, (SEQ ID No. 19)
BvCENH3_L -> F_Rv: CTCTGCAGCCTCTTGAAGGGCCATAAAAGC, (SEQ ID No. 20)
BvCENH3_L -> I_Rv: CTCTGCAGCCTCTTGAAGGGCCATAATAGC.
```

Resulting expression cassettes (35Spro, RFP-(mutated) CENH3 and 35S-terminator) were verified by sequencing.

Analysis of CENH3 binding in *B. vulgaris*

To analyse the binding of CENH3 and the mutated CENH3 either leaf or callus material was analysed using a C-Apo 63x/1.2 W Korr objective of an Axio Imager M2 microscope system and the software ZEN (Zeiss, Germany).

Example 4: Identification and Testing of Other CENH3 Mutants

For the identification of other single point mutations within the endogenous gene of CENH3 which cause an amino acid substitution or a deletion of one or more amino acids of the sequence of the translated CENH3. Even if Ravi und Chan 2010 highlighted only the particular importance of the N terminal domain, above described studies on mutants in another part of CENH3 like α2-helix (Example 1 to 3) gave indications that the modification of CATD domain of CENH3 can result in a destabilization of the CENH3 binding capacities to DNA. Therefore the focus was on identification of other mutations within the CATD, in particular in the loop1 and α2-helix. Additionally, it should be demonstrated that due to the high level of conservation of the CATD domain between the species, an identified mutation has the potential to confer the biological activity of a haploid inducer to different plant species.

For that TILLING populations having high mutation rates have been generated for two other monocot plants namely for corn (*Zea mays*) and sorghum (*Sorghum bicolor*), and for two dicot plants namely for rape seed (*Brassica napus*) and sugar beet (*Beta vulgaris*). In order to screen for mutations in the endogenous CENH3 gene which result in at least one amino acid substitution or a deletion of at least one amino acid in the CATD domain of the translated CENH3 protein, amplicons covering all exons of the CENH3 genes as well as parts of the corresponding introns, respectively, have been developed as exemplary described above for barley (Example 1) and between 1000 and 10000 individuals per plant species have been analyzed by means of Sanger's sequencing method. In addition, M2 sugar beet plants have been tested for mutations using specific PCR.

Furthermore, the affect of the identified mutation within the CENH3 gene on the primary and secondary structure of the encoded protein have been evaluated using inter alia the software Prof (Rost, B. and Sander, C. (1994a). Combining evolutionary information and neural networks to predict protein secondary structure. Proteins, 19(1), 55-72. Rost, B. and Sander, C. (1994b). Conservation and prediction of solvent accessibility in protein families. Proteins, 20(3), 216-26. Rost, B., Casadio, R., Fariselli, P., and Sander, C. (1995). Transmembrane helices predicted at 95% accuracy. Protein Sci, 4(3), 521-33).

The non-functionality of mutated CENH3s of homozygous mutants has been tested for example by immunostaining of centromeres with CENH3 specific antibodies as described above (Examples 1 and 2). Identified TILLING lines showed significantly reduced or impaired centromeric loading by the mutated CENH3. Plants having a genome which was heterozygous for such mutation(s) were viable and no obvious changes of the plant habitus were observed, i.e. phenotype, poidy levels, cycle values and growth were comparable to corresponding wildtype plants with regard to statistic accuracy.

The biological activity of a haploid inducer in the identified mutants has been evaluated by crossing the mutant plants with a tester plant of the same species: The tester plant carries the wildtype form of CENH3. The maternal as well as the paternal performance of haploid induction have been tested. For that, the mutant plants have been used either as ovule parent or as pollen parent in the cross with the tester plant. Putative haploid progeny from this cross can be determined quickly if the used tester lines carry a recessive non-CENH3 mutation. So, the haploid plants show the recessive phenotype. For example, in corn the manifestation of the mutation glossy (Mutants of maize, Neuffer, M G et al. 1997. Cold Spring Harbor Laboratory, New York) can be used. Haploid progeny from these crosses can be determined quickly if the used tester lines carry a recessive non-CENH3 mutation. So, the haploid plants show the recessive phenotype. For example, in corn the manifestation of the mutation glossy (Mutants of maize, Neuffer, M G et al. 1997. Cold Spring Harbor Laboratory, New York) can be used.

Additionally, cytogenetic analyses of mitose and meiose with the inductors indicates also for suitability of mutants as haploid inducers and homozygosity has been determined by use of molecular markers, polymorph for tester and potential inductor. Haploidy as such could be tested cytogenetically.

The following Tables shows the missense and deletion mutations which confer the biological activity of a haploid inducer to investigated plant species:

TABLE 4 mutation of the CENH3 derived from *Brassica napus* (aa: amino acid; nd: not determined, y: yes, n: no). Amino acid substitution is given as X#Y, i.e. amino acid X (one letter code) is substituted for amino acid Y at position #.

| mutation identifier (SEQ ID Nos of genomic DNA; cDNA; amino acid) | codon wildtype | codon mutant | mutation | chance in secondary structure |
|---|---|---|---|---|
| BN_CenH3_26 (62; 63; 64) | cct | tct | P121S | n |
| BN_CenH3_27 (65; 66; 67) | tgg | tga | W127stop | n |
| BN_CenH3_28 (68; 69; 70) | ctt | ttt | L132F | y |
| BN_CenH3_29 (71; 72; 73) | gcg | acg | A138T | n |
| BN_CenH3_30 (74; 75; 76) | tgc | tac | C153Y | y |
| BN_CenH3_31 (77; 78; 79) | gct | gtt | A154V | y |

TABLE 5 mutation of the CENH3 derived from *Zea mays* (aa: amino acid; nd: not determined, y: yes, n: no). Amino acid substitution is given as X#Y, i.e. amino acid X (one letter code) is substituted for amino acid Y at position #.

| mutation identifier (SEQ ID Nos of genomic DNA; cDNA; amino acid) | codon wildtype | codon mutant | mutation | chance in secondary structure |
|---|---|---|---|---|
| ZM_CenH3_07 (80; 81; 82) | gca | aca | A107T | nd |
| ZM_CenH3_08 (83; 84; 85) | caa | taa | Q114stop | nd |

TABLE 6 mutation of the CENH3 derived from *Sorghum bicolor* (aa: amino acid; nd: not determined, y: yes, n: no). Amino acid substitution is given as X#Y, i.e. amino acid X (one letter code) is substituted for amino acid Y at position #.

| mutation identifier (SEQ ID Nos of genomic DNA; cDNA; amino acid) | codon wildtype | codon mutant | mutation | chance in secondary structure |
|---|---|---|---|---|
| SB_CenH3_04 (86; 87; 88) | gca | gta | A95V | nd |

TABLE 7 mutation of the CENH3 derived from *Beta vulgaris* (nd: not determined, y: yes, n: no). Amino acid substitution is given as X#Y, i.e. amino acid X (one letter code) is substituted for amino acid Y at position #.

| mutation identifier (SEQ ID Nos of genomic DNA; cDNA; amino acid) | codon wildtype | codon mutant | mutation | chance in secondary structure |
|---|---|---|---|---|
| Bv_CenH3_04 (89; 90; 91) | ctg | cag | L106Q | nd |
| Bv_CenH3_05 (92; 93; 94) | ctt | cct | L109P | nd |
| Bv_CenH3_06 (95; 96; 97) | caa | cta | Q110L | nd |

The crossings with the tester plants the TILLING plants with mutated endogenous CENH3 yielded at least 0.5% haploid progeny. For example, in *Brassica napus* the mutations C153Y and A154V showed induction rates between 0.5% and 1%. In a few cases induction rates of 2% or more could be reached. Frequently the induction rate was higher if the tester was used as male parent in the cross.

Moreover, the result of crossing demonstrated that identified mutations could be functional also in other plant species. Thus, mutation at amino acid position 4 of the consensus sequence SEQ ID No. 1, whereby leucine has been substituted for phenylalanine created induction activity in *Hordeum vulgare* (L92F) as shown in Examples 1 to 3 but also in *Brassica napus* (L132F). Therefore mutations could be introduced into other plant species by techniques like TILLING, Mutagenesis or genome editing (e.g. CRISPR/Cas, TALENs, Zinc Finger nucleases etc.). Moreover, the biological activity and efficiency of a haploid inducer could be further improved by combining different identified mutations in one plant and/or modifying the genetic background of the haploid inducer. The combination of different mutations could be achieved efficiently by genome editing, or the mutant haploid inducer is mutagenized for a second time.

The invention claimed is:

1. A plant having biological activity of a haploid inducer and comprising a nucleotide sequence encoding a centromere histone H3 (CENH3) protein comprising a CATD domain, wherein the nucleotide sequence comprises a mutation encoding a polypeptide having one or more amino acid substitutions at positions 1, 4, 8, 10, 22, 25 and 26 of an α2-helix consensus sequence, wherein said alteration confers the biological activity of a haploid inducer, wherein the plant is homozygous with respect to the mutation and is not able to express a native CENH3 protein, and
wherein the α2-helix consensus sequence comprises A, P, V or L at position 1; E, D, Q, H or L at position 2; A at position 3; L or V at position 4; V, L, M, I, R, Y or T at position 5; S or A at position 6; Q at position 8; E at position 9; A or S at position 10; A or T at position 11; E at position 12; D, N, F, I or Y at position 13; Y, F or H at position 14; L, I or V at position 15; V or I at position 16; G, R, E, H, N, T, E, D or Q at position 17; L, M or I at position 18; F, M or L at position 19; S, E, D or G at position 20; D, M, V, N, E, A, R or K at position 21; S, G, A or T at position 22; M, W, N or H at position 23; L or H at position 24; C or L at position 25; A or T at position 26; L or I at position 27; H at position 28; and A or S at position 29.

2. The plant according to claim 1, wherein crossing between the plant and a wildtype plant or a plant expressing wildtype CENH3 protein yields at least 0.1% haploid progeny.

3. The plant according to claim 1, wherein the nucleotide sequence comprising the mutation is an endogenous gene or a transgene.

4. The plant according to claim 3, wherein the nucleotide sequence comprising the mutation is a transgene.

5. The plant according to claim 1, wherein the one or more amino acid substitutions comprise:
   a substitution for the amino acid A, P, V or L at position 1 of the α2-helix consensus sequence;
   a substitution for the amino acid L or V at position 4 of the α2-helix consensus sequence;
   a substitution for the amino acid Q at position 8 of the α2-helix consensus sequence;
   a substitution for the amino acid A or S at position 10 of the α2-helix consensus sequence;
   a substitution for the amino acid A at position 22 of the α2-helix consensus sequence;
   a substitution for the amino acid C or L at position 25 of the α2-helix consensus sequence; and
   a substitution for the amino acid A or T at position 26 of the α2-helix consensus sequence.

6. A part of the plant according to claim 1 comprising a mutation causing in the CATD domain an alteration of the amino acid sequence at position 4 of the α2-helix sequence of the α2-helix consensus sequence.

7. A method of generating a haploid plant, comprising the steps of:
   a) crossing a plant according to claim 1 to a plant expressing wildtype CENH3 protein, and
   b) identifying the haploid progeny plant generated from the crossing step.

8. A method of generating a double haploid plant, comprising the steps of:
   a) crossing a plant according to claim 1 to a plant expressing wildtype CENH3 protein,
   b) identifying a haploid progeny plant generated from the crossing step, and
   c) converting the haploid progeny plant into a double haploid plant.

9. A method of facilitating a cytoplasm exchange, comprising the steps of:
x) crossing a plant according to claim 1 as ovule parent with a plant expressing wildtype CENH3 protein as pollen parent, and
y) obtaining a haploid progeny plant comprising the chromosomes of the pollen parent and the cytoplasm of ovule parent.

10. A method of generating a plant according to claim 1, comprising the steps of:
i) subjecting seeds of a plant to a sufficient amount of the mutagen ethylmethane sulfonate to obtain M1 plants,
ii) allowing sufficient production of fertile M2 plants,
iii) isolating genomic DNA of M2 plants and
iv) selecting individuals comprising said nucleotide sequence comprising said one or more mutations of the α2-helix consensus sequence, wherein said substitution confers the biological activity of a haploid inducer, and wherein the plant is homozygous with respect to the mutation and is not able to express a native CENH3 protein.

11. An isolated nucleotide sequence encoding a centromere histone H3 (CENH3) protein comprising a CATD domain, wherein the nucleotide sequence encodes a polypeptide having substitutions at one or more of positions 1, 4, 8, 10, 22, 25 and 26 of an α2-helix consensus sequence of SEQ ID NO: 1.

12. A vector comprising the nucleotide sequence of claim 11.

13. A plant cell or a host cell comprising the nucleotide sequence of claim 11, or a vector comprising said nucleotide sequence, as a transgene.

14. A method of generating a transgenic plant comprising the steps of:
yy) transforming a plant cell with the nucleotide sequence of claim 11, or a vector comprising said nucleotide sequence, and
zz) regenerating a plant having the biological activity of a haploid inducer from the plant cell.

15. The part of the plant according to claim 6, wherein the part is a shoot vegetative organ, root, flower or floral organ, seed, fruit, ovule, embryo, plant tissue or cell.

16. The plant according to claim 1, wherein the one or more mutations comprise:
a T at position 1 of the α2-helix sequence of the α2-helix consensus sequence; a F at position 4 of the α2-helix sequence of the α2-helix consensus sequence; a stop codon or a L at position 8 of the α2-helix sequence of the α2-helix consensus sequence; a T at position 10 of the α2-helix sequence of the α2-helix consensus sequence; a T at position 22 of the α2-helix sequence of the α2-helix consensus sequence; a Y at position 25 of the α2-helix sequence of the α2-helix consensus sequence; and/or a V at position 26 of the α2-helix sequence of the α2-helix consensus sequence.

* * * * *

UNITED STATES PATENT AND TRADEMARK OFFICE
CERTIFICATE OF CORRECTION

PATENT NO. : 10,993,391 B2
APPLICATION NO. : 15/507538
DATED : May 4, 2021
INVENTOR(S) : Andreas Houben et al.

It is certified that error appears in the above-identified patent and that said Letters Patent is hereby corrected as shown below:

On the Title Page

Under "(72) Inventors:",
Please correct Jochen Kumlehm to Jochen Kumlehn

Signed and Sealed this
Twenty-sixth Day of March, 2024

Katherine Kelly Vidal
*Director of the United States Patent and Trademark Office*

SEQUENCE LISTING

<160> NUMBER OF SEQ ID NOS: 97

<210> SEQ ID NO 1
<211> LENGTH: 29
<212> TYPE: PRT
<213> ORGANISM: Artificial Sequence

```
<220> FEATURE:
<223> OTHER INFORMATION: amino acid consensus sequence of the
      Alpha-2-helix of the CENH3

<400> SEQUENCE: 1

Ala Glu Ala Leu Leu Ala Leu Gln Glu Ala Ala Glu Asp Phe Leu Val
1               5                   10                  15

His Leu Phe Glu Asp Ala Met Leu Cys Ala Ile His Ala
            20                  25

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aggcagggtc tcaattcctt                                              20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gtcccatcat ccatcgtctt                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cccacttcct tgttgtggac                                              20

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
ggcgataaat gtatcttgca ttc                                          23

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tggtagcaac cagagctacg                                              20

<210> SEQ ID NO 7
<211> LENGTH: 20
<212> TYPE: DNA
<213> ORGANISM: Artificial Sequence
<220> FEATURE:
<223> OTHER INFORMATION: Primer
```

<400> SEQUENCE: 7
actggcatgt ttccttctgc                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cggacggagg gagtatttct                                              20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ggacatgccc aaagaaagtg                                              20

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gccagcgagt actcctacaa g                                            21

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ttgagttacc agccaccact c                                            21

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gtcatgcact gtgtcttgca                                              20

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
tgctaagatc ggataactgt gg                                           22

<210> SEQ ID NO 14

<211> LENGTH: 21
<212> TYPE: DNA
<213> ORGANISM: Artificial Sequence
<220> FEATURE:
<223> OTHER INFORMATION: Primer

<400> SEQUENCE: 14
tgctcctgaa caaactgaac c                                              21

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
gtggccgtca gtacaatcg                                                 19

<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
ggatccatga gagttaaaca cactgc                                         26

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
ggatcctgtt cagttaccat cccctc                                         26

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
atggatccat gagagttaaa cacactgc                                       28

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
ctctgcagcc tcttgaaggg ccataaaagc                                     30

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20

```
ctctgcagcc tcttgaaggg ccataatagc                                    30

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
caatgatagc tgcaccacca actg                                          24

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
ctagctgccc ttccacctct cca                                           23

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
agtcggtcaa ttttctcatc cc                                            22

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
ctctgtagcc tcttgaactg c                                             21

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gccattgtcg aacaagaagg                                               20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
taacacggtg cgaatgaatg                                               20

<210> SEQ ID NO 27
<211> LENGTH: 26
<212> TYPE: DNA
```

```
<213> ORGANISM: Artificial Sequence
<220> FEATURE:
<223> OTHER INFORMATION: Primer

<400> SEQUENCE: 27
gacagctgaa gcatttgttg ctcttc                                          26

<210> SEQ ID NO 28
<211> LENGTH: 26
<212> TYPE: DNA
<213> ORGANISM: Artificial Sequence
<220> FEATURE:
<223> OTHER INFORMATION: Primer

<400> SEQUENCE: 28
gacagctgaa gctattgttg ctcttc                                          26

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
caacgattga tttggggagg g                                               21

<210> SEQ ID NO 30
<211> LENGTH: 27
<212> TYPE: DNA
<213> ORGANISM: Artificial Sequence
<220> FEATURE:
<223> OTHER INFORMATION: Primer

<400> SEQUENCE: 30
ggtgcgattt ctccagcagt aaaaatc                                         27

<210> SEQ ID NO 31
<211> LENGTH: 26
<212> TYPE: DNA
<213> ORGANISM: Artificial Sequence
<220> FEATURE:
<223> OTHER INFORMATION: Primer

<400> SEQUENCE: 31
ctgagaagat gaagcaccgg cgatat                                          26

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
aacttttgcc atcctcgttt ctgtt                                           25

<210> SEQ ID NO 33
<211> LENGTH: 420
<212> TYPE: DNA
<213> ORGANISM: Hordeum vulgare

<400> SEQUENCE: 33
atggctcgca cgaagaaaac ggtggcggcg aaggagaagc gccccccttg ctccaagtcg     60
gagccgcagt cgcagccgaa gaagaaggag aagcgggcgt accggttccg gccgggcacg    120
```

```
gtggcgctgc gggagatccg gaagtaccgc aagtccacca atatgctcat cccctttgcg    180
ccctccgtcc gcctggtcag ggacatcgcc gacaacttga cgccattgtc gaacaagaag    240
gagagcaagc cgacgccatg gactcctctc gcgctcctct cgttgcaaga gtctgcagag    300
tatcacttgg tcgatctatt tggaaaggca aatctgtgtg ccattcattc gcaccgtgtt    360
accatcatgc taaaggacat gcagcttgcg aggcgtatcg ggacgagaag cctttggtga    420
```

<210> SEQ ID NO 34
<211> LENGTH: 139
<212> TYPE: PRT
<213> ORGANISM: Hordeum vulgare

<400> SEQUENCE: 34

```
Met Ala Arg Thr Lys Lys Thr Val Ala Ala Lys Glu Lys Arg Pro Pro
 1               5                  10                  15

Cys Ser Lys Ser Glu Pro Gln Ser Gln Pro Lys Lys Lys Glu Lys Arg
                20                  25                  30

Ala Tyr Arg Phe Arg Pro Gly Thr Val Ala Leu Arg Glu Ile Arg Lys
            35                  40                  45

Tyr Arg Lys Ser Thr Asn Met Leu Ile Pro Phe Ala Pro Phe Val Arg
        50                  55                  60

Leu Val Arg Asp Ile Ala Asp Asn Leu Thr Pro Leu Ser Asn Lys Lys
 65                  70                  75                  80

Glu Ser Lys Pro Thr Pro Trp Thr Pro Leu Ala Leu Ser Leu Gln
                85                  90                  95

Glu Ser Ala Glu Tyr His Leu Val Asp Leu Phe Gly Lys Ala Asn Leu
            100                 105                 110

Cys Ala Ile His Ser His Arg Val Thr Ile Met Leu Lys Asp Met Gln
        115                 120                 125

Leu Ala Arg Arg Ile Gly Thr Arg Ser Leu Trp
    130                 135
```

<210> SEQ ID NO 35
<211> LENGTH: 420
<212> TYPE: DNA
<213> ORGANISM: Hordeum vulgare
<220> FEATURE:
<221> NAME/KEY: misc_feature
<222> LOCATION: (1)..(420)
<223> OTHER INFORMATION: obtained from Tilling Line 4528 Mutant

<400> SEQUENCE: 35

```
atggctcgca cgaagaaaac ggtggcggcg aaggagaagc gccccccttg ctccaagtcg     60
gagccgcagt cgcagccgaa gaagaaggag aagcgggcgt accggttccg gccgggcacg    120
gtggcgctgc gggagatccg gaagtaccgc aagtccacca atatgctcat cccctttgcg    180
ccctccgtcc gcctggtcag ggacatcgcc gacaacttga cgccattgtc gaacaagaag    240
gagagcaagc cgacgccatg gactcctctc gcgttcctct cgttgcaaga gtctgcagag    300
tatcacttgg tcgatctatt tggaaaggca aatctgtgtg ccattcattc gcaccgtgtt    360
accatcatgc taaaggacat gcagcttgcg aggcgtatcg ggacgagaag cctttggtga    420
```

<210> SEQ ID NO 36
<211> LENGTH: 139
<212> TYPE: PRT
<213> ORGANISM: Hordeum vulgare
<220> FEATURE:
<221> NAME/KEY: MISC_FEATURE
<222> LOCATION: (1)..(139)
<223> OTHER INFORMATION: obtained from Tilling Line 4528 Mutant

<400> SEQUENCE: 36

```
Met Ala Arg Thr Lys Lys Thr Val Ala Ala Lys Glu Lys Arg Pro Pro
1               5                   10                  15

Cys Ser Lys Ser Glu Pro Gln Ser Gln Pro Lys Lys Lys Glu Lys Arg
            20                  25                  30

Ala Tyr Arg Phe Arg Pro Gly Thr Val Ala Leu Arg Glu Ile Arg Lys
        35                  40                  45

Tyr Arg Lys Ser Thr Asn Met Leu Ile Pro Phe Ala Pro Phe Val Arg
    50                  55                  60

Leu Val Arg Asp Ile Ala Asp Asn Leu Thr Pro Leu Ser Asn Lys Lys
65                  70                  75                  80

Glu Ser Lys Pro Thr Pro Trp Thr Pro Leu Ala Phe Leu Ser Leu Gln
                85                  90                  95

Glu Ser Ala Glu Tyr His Leu Val Asp Leu Phe Gly Lys Ala Asn Leu
            100                 105                 110

Cys Ala Ile His Ser His Arg Val Thr Ile Met Leu Lys Asp Met Gln
        115                 120                 125

Leu Ala Arg Arg Ile Gly Thr Arg Ser Leu Trp
    130                 135
```

<210> SEQ ID NO 37
<211> LENGTH: 537
<212> TYPE: DNA
<213> ORGANISM: Arabidopsis thaliana

<400> SEQUENCE: 37

```
atggcgagaa ccaagcatcg cgttaccagg tcacaacctc ggaatcaaac tgatgccgcc    60
ggtgcttcat cttctcaggc ggcaggtcca actacgaccc cgacaaggag aggcggtgaa   120
ggtggagata atactcaaca aacaaatcct acaacttcac cagctactgg tacaaggaga   180
ggggctaaga gatccagaca ggctatgcca cgaggctcac agaagaagtc ttatcgatac   240
aggccaggaa ccgttgctct aaaagagatt cgccatttcc agaagcagac aaaccttctt   300
attccggctg ccagtttcat aagagaagtg agaagtataa cccatatgtt ggcccctccc   360
caaatcaatc gttggacagc tgaagctctt gttgctcttc aagaggcggc agaagattac   420
ttggttggtt tgttctcaga ttcaatgctc tgtgctatcc atgcaagacg tgttactcta   480
atgagaaaag actttgaact tgcacgccgg cttggaggaa aaggcagacc atggtga     537
```

<210> SEQ ID NO 38
<211> LENGTH: 178
<212> TYPE: PRT
<213> ORGANISM: Arabidopsis thaliana

<400> SEQUENCE: 38

```
Met Ala Arg Thr Lys His Arg Val Thr Arg Ser Gln Pro Arg Asn Gln
1               5                   10                  15

Thr Asp Ala Ala Gly Ala Ser Ser Gln Ala Ala Gly Pro Thr Thr
            20                  25                  30

Thr Pro Thr Arg Arg Gly Gly Glu Gly Gly Asp Asn Thr Gln Gln Thr
        35                  40                  45

Asn Pro Thr Thr Ser Pro Ala Thr Gly Thr Arg Arg Gly Ala Lys Arg
    50                  55                  60

Ser Arg Gln Ala Met Pro Arg Gly Ser Gln Lys Lys Ser Tyr Arg Tyr
```

```
                65                  70                  75                  80
Arg Pro Gly Thr Val Ala Leu Lys Glu Ile Arg His Phe Gln Lys Gln
                    85                  90                  95

Thr Asn Leu Leu Ile Pro Ala Ala Ser Phe Ile Arg Glu Val Arg Ser
                100                 105                 110

Ile Thr His Met Leu Ala Pro Pro Gln Ile Asn Arg Trp Thr Ala Glu
                115                 120                 125

Ala Leu Val Ala Leu Gln Glu Ala Ala Glu Asp Tyr Leu Val Gly Leu
            130                 135                 140

Phe Ser Asp Ser Met Leu Cys Ala Ile His Ala Arg Arg Val Thr Leu
145                 150                 155                 160

Met Arg Lys Asp Phe Glu Leu Ala Arg Arg Leu Gly Gly Lys Gly Arg
                165                 170                 175

Pro Trp

<210> SEQ ID NO 39
<211> LENGTH: 537
<212> TYPE: DNA
<213> ORGANISM: Arabidopsis thaliana

<400> SEQUENCE: 39
atggcgagaa ccaagcatcg cgttaccagg tcacaacctc ggaatcaaac tgatgccgcc      60
ggtgcttcat cttctcaggc ggcaggtcca actacgaccc cgacaaggag aggcggtgaa     120
ggtggagata atactcaaca aacaaatcct acaacttcac cagctactgg tacaaggaga     180
ggggctaaga gatccagaca ggctatgcca cgaggctcac agaagaagtc ttatcgatac     240
aggccaggaa ccgttgctct aaaagagatt cgccatttcc agaagcagac aaaccttctt     300
attccggctg ccagtttcat aagagaagtg agaagtataa cccatatgtt ggcccctccc     360
caaatcaatc gttggacagc tgaagctatt gttgctcttc aagaggcggc agaagattac     420
ttggttggtt tgttctcaga ttcaatgctc tgtgctatcc atgcaagacg tgttactcta     480
atgagaaaag actttgaact tgcacgccgg cttggaggaa aaggcagacc atggtga        537

<210> SEQ ID NO 40
<211> LENGTH: 178
<212> TYPE: PRT
<213> ORGANISM: Arabidopsis thaliana

<400> SEQUENCE: 40

Met Ala Arg Thr Lys His Arg Val Thr Arg Ser Gln Pro Arg Asn Gln
1               5                   10                  15

Thr Asp Ala Ala Gly Ala Ser Ser Ser Gln Ala Ala Gly Pro Thr Thr
                20                  25                  30

Thr Pro Thr Arg Arg Gly Gly Glu Gly Gly Asp Asn Thr Gln Gln Thr
            35                  40                  45

Asn Pro Thr Thr Ser Pro Ala Thr Gly Thr Arg Arg Gly Ala Lys Arg
        50                  55                  60

Ser Arg Gln Ala Met Pro Arg Gly Ser Gln Lys Lys Ser Tyr Arg Tyr
65                  70                  75                  80

Arg Pro Gly Thr Val Ala Leu Lys Glu Ile Arg His Phe Gln Lys Gln
                    85                  90                  95

Thr Asn Leu Leu Ile Pro Ala Ala Ser Phe Ile Arg Glu Val Arg Ser
                100                 105                 110

Ile Thr His Met Leu Ala Pro Pro Gln Ile Asn Arg Trp Thr Ala Glu
                115                 120                 125
```

Ala Ile Val Ala Leu Gln Glu Ala Ala Glu Asp Tyr Leu Val Gly Leu
            130                 135                 140

Phe Ser Asp Ser Met Leu Cys Ala Ile His Ala Arg Arg Val Thr Leu
145                 150                 155                 160

Met Arg Lys Asp Phe Glu Leu Ala Arg Arg Leu Gly Gly Lys Gly Arg
            165                 170                 175

Pro Trp

<210> SEQ ID NO 41
<211> LENGTH: 537
<212> TYPE: DNA
<213> ORGANISM: Arabidopsis thaliana

<400> SEQUENCE: 41
atggcgagaa ccaagcatcg cgttaccagg tcacaacctc ggaatcaaac tgatgccgcc      60
ggtgcttcat cttctcaggc ggcaggtcca actacgaccc cgacaaggag aggcggtgaa     120
ggtggagata atactcaaca acaaatcct acaacttcac cagctactgg tacaaggaga      180
ggggctaaga gatccagaca ggctatgcca cgaggctcac agaagaagtc ttatcgatac     240
aggccaggaa ccgttgctct aaaagagatt cgccatttcc agaagcagac aaaccttctt     300
attccggctg ccagtttcat aagagaagtg agaagtataa cccatatgtt ggcccctccc     360
caaatcaatc gttggacagc tgaagcattt gttgctcttc aagaggcggc agaagattac     420
ttggttggtt tgttctcaga ttcaatgctc tgtgctatcc atgcaagacg tgttactcta     480
atgagaaaag actttgaact tgcacgccgg cttggaggaa aggcagacc atggtga        537

<210> SEQ ID NO 42
<211> LENGTH: 178
<212> TYPE: PRT
<213> ORGANISM: Arabidopsis thaliana

<400> SEQUENCE: 42

Met Ala Arg Thr Lys His Arg Val Thr Arg Ser Gln Pro Arg Asn Gln
1               5                   10                  15

Thr Asp Ala Ala Gly Ala Ser Ser Gln Ala Ala Gly Pro Thr Thr
            20                  25                  30

Thr Pro Thr Arg Arg Gly Gly Glu Gly Gly Asp Asn Thr Gln Gln Thr
            35                  40                  45

Asn Pro Thr Thr Ser Pro Ala Thr Gly Thr Arg Gly Ala Lys Arg
50                  55                  60

Ser Arg Gln Ala Met Pro Arg Gly Ser Gln Lys Lys Ser Tyr Arg Tyr
65                  70                  75                  80

Arg Pro Gly Thr Val Ala Leu Lys Glu Ile Arg His Phe Gln Lys Gln
            85                  90                  95

Thr Asn Leu Leu Ile Pro Ala Ala Ser Phe Ile Arg Glu Val Arg Ser
            100                 105                 110

Ile Thr His Met Leu Ala Pro Pro Gln Ile Asn Arg Trp Thr Ala Glu
            115                 120                 125

Ala Phe Val Ala Leu Gln Glu Ala Ala Glu Asp Tyr Leu Val Gly Leu
            130                 135                 140

Phe Ser Asp Ser Met Leu Cys Ala Ile His Ala Arg Arg Val Thr Leu
145                 150                 155                 160

Met Arg Lys Asp Phe Glu Leu Ala Arg Arg Leu Gly Gly Lys Gly Arg
            165                 170                 175

Pro Trp

<210> SEQ ID NO 43
<211> LENGTH: 465
<212> TYPE: DNA
<213> ORGANISM: Beta vulgaris

<400> SEQUENCE: 43

```
atgagagtta aacacactgc tgccaggaaa tcaaccacca atggtcctcg ttcaaaggct      60
cagaaatctc cgcgcagttt gcaatcacca caatcgcctt ctagtagttc aaagcgcaaa     120
tcacgcagaa acactgatgc aactcctcaa aagaagaagg cttaccgccg taagccgggc     180
actgtggcac tctgggaaat acgcaaattt cagaagtcat tcaagccctt gattcctgct     240
gcgcctttca ttcgaacagt gagagagatt actcaccagt ttgctcctta tgttggtcgt     300
tggcaagctg aagctctgat ggcccttcaa gaggctgcag agaatttat tgtccgtttg      360 tttgaagatg gtatgctttg tgcaattcat gccaaacgag ttacactcat gaaaaaggat     420
ttggagctcg cgcgaaggat tgggggcaga gagagggat ggtaa                      465
```

<210> SEQ ID NO 44
<211> LENGTH: 154
<212> TYPE: PRT
<213> ORGANISM: Beta vulgaris

<400> SEQUENCE: 44

```
Met Arg Val Lys His Thr Ala Ala Arg Lys Ser Thr Asn Gly Pro
1               5                   10                  15

Arg Ser Lys Ala Gln Lys Ser Pro Arg Ser Leu Gln Ser Pro Gln Ser
                20                  25                  30

Pro Ser Ser Ser Lys Arg Lys Ser Arg Arg Asn Thr Asp Ala Thr
            35                  40                  45

Pro Gln Lys Lys Lys Ala Tyr Arg Arg Lys Pro Gly Thr Val Ala Leu
        50                  55                  60

Trp Glu Ile Arg Lys Phe Gln Lys Ser Phe Lys Pro Leu Ile Pro Ala
65                  70                  75                  80

Ala Pro Phe Ile Arg Thr Val Arg Glu Ile Thr His Gln Phe Ala Pro
                85                  90                  95

Tyr Val Gly Arg Trp Gln Ala Glu Ala Leu Met Ala Leu Gln Glu Ala
                100                 105                 110

Ala Glu Asn Phe Ile Val Arg Leu Phe Glu Asp Gly Met Leu Cys Ala
            115                 120                 125

Ile His Ala Lys Arg Val Thr Leu Met Lys Lys Asp Leu Glu Leu Ala
        130                 135                 140

Arg Arg Ile Gly Gly Arg Glu Arg Gly Trp
145                 150
```

<210> SEQ ID NO 45
<211> LENGTH: 465
<212> TYPE: DNA
<213> ORGANISM: Beta vulgaris

<400> SEQUENCE: 45

```
atgagagtta aacacactgc tgccaggaaa tcaaccacca atggtcctcg ttcaaaggct      60
cagaaatctc cgcgcagttt gcaatcacca caatcgcctt ctagtagttc aaagcgcaaa     120
tcacgcagaa acactgatgc aactcctcaa aagaagaagg cttaccgccg taagccgggc     180
actgtggcac tctgggaaat acgcaaattt cagaagtcat tcaagccctt gattcctgct     240
```

```
gcgcctttca ttcgaacagt gagagagatt actcaccagt ttgctcctta tgttggtcgt    300
tggcaagctg aagctttat ggcccttcaa gaggctgcag agaattttat tgtccgtttg     360
tttgaagatg gtatgctttg tgcaattcat gccaaacgag ttacactcat gaaaaaggat    420
ttggagctcg cgcgaaggat tgggggcaga gagagggat ggtaa                     465
```

<210> SEQ ID NO 46
<211> LENGTH: 154
<212> TYPE: PRT
<213> ORGANISM: Beta vulgaris

<400> SEQUENCE: 46

```
Met Arg Val Lys His Thr Ala Ala Arg Lys Ser Thr Thr Asn Gly Pro
1               5                   10                  15

Arg Ser Lys Ala Gln Lys Ser Pro Arg Ser Leu Gln Ser Pro Gln Ser
            20                  25                  30

Pro Ser Ser Ser Lys Arg Lys Ser Arg Arg Asn Thr Asp Ala Thr
        35                  40                  45

Pro Gln Lys Lys Lys Ala Tyr Arg Arg Lys Pro Gly Thr Val Ala Leu
    50                  55                  60

Trp Glu Ile Arg Lys Phe Gln Lys Ser Phe Lys Pro Leu Ile Pro Ala
65                  70                  75                  80

Ala Pro Phe Ile Arg Thr Val Arg Glu Ile Thr His Gln Phe Ala Pro
                85                  90                  95

Tyr Val Gly Arg Trp Gln Ala Glu Ala Phe Met Ala Leu Gln Glu Ala
            100                 105                 110

Ala Glu Asn Phe Ile Val Arg Leu Phe Glu Asp Gly Met Leu Cys Ala
        115                 120                 125

Ile His Ala Lys Arg Val Thr Leu Met Lys Lys Asp Leu Glu Leu Ala
    130                 135                 140

Arg Arg Ile Gly Gly Arg Glu Arg Gly Trp
145                 150
```

<210> SEQ ID NO 47
<211> LENGTH: 465
<212> TYPE: DNA
<213> ORGANISM: Beta vulgaris

<400> SEQUENCE: 47

```
atgagagtta aacacactgc tgccaggaaa tcaaccacca atggtcctcg ttcaaaggct    60
cagaaatctc cgcgcagttt gcaatcacca caatcgcctt ctagtagttc aaagcgcaaa   120
tcacgcagaa acactgatgc aactcctcaa aagaagaagg cttaccgccg taagccgggc   180
actgtggcac tctgggaaat acgcaaattt cagaagtcat tcaagccctt gattcctgct   240
gcgcctttca ttcgaacagt gagagagatt actcaccagt ttgctcctta tgttggtcgt   300
tggcaagctg aagctattat ggcccttcaa gaggctgcag agaattttat tgtccgtttg   360
tttgaagatg gtatgctttg tgcaattcat gccaaacgag ttacactcat gaaaaaggat   420
ttggagctcg cgcgaaggat tgggggcaga gagagggat ggtaa                    465
```

<210> SEQ ID NO 48
<211> LENGTH: 154
<212> TYPE: PRT
<213> ORGANISM: Beta vulgaris

<400> SEQUENCE: 48

```
Met Arg Val Lys His Thr Ala Ala Arg Lys Ser Thr Thr Asn Gly Pro
1               5                   10                  15

Arg Ser Lys Ala Gln Lys Ser Pro Arg Ser Leu Gln Ser Pro Gln Ser
            20                  25                  30

Pro Ser Ser Ser Lys Arg Lys Ser Arg Arg Asn Thr Asp Ala Thr
        35                  40                  45

Pro Gln Lys Lys Lys Ala Tyr Arg Arg Lys Pro Gly Thr Val Ala Leu
    50                  55                  60

Trp Glu Ile Arg Lys Phe Gln Lys Ser Phe Lys Pro Leu Ile Pro Ala
65                  70                  75                  80

Ala Pro Phe Ile Arg Thr Val Arg Glu Ile Thr His Gln Phe Ala Pro
                85                  90                  95

Tyr Val Gly Arg Trp Gln Ala Glu Ala Ile Met Ala Leu Gln Glu Ala
                100                 105                 110

Ala Glu Asn Phe Ile Val Arg Leu Phe Glu Asp Gly Met Leu Cys Ala
            115                 120                 125

Ile His Ala Lys Arg Val Thr Leu Met Lys Lys Asp Leu Glu Leu Ala
        130                 135                 140

Arg Arg Ile Gly Gly Arg Glu Arg Gly Trp
145                 150
```

<210> SEQ ID NO 49
<211> LENGTH: 13
<212> TYPE: PRT
<213> ORGANISM: Artificial Sequence
<220> FEATURE:
<223> OTHER INFORMATION: amino acid consensus sequence of the loop1 of
      the CENH3
<220> FEATURE:
<221> NAME/KEY: misc_feature
<222> LOCATION: (7)..(7)
<223> OTHER INFORMATION: Xaa can be any naturally occurring amino acid

<400> SEQUENCE: 49

```
Thr Asn Phe Leu Ala Pro Xaa Glu Val Thr Arg Trp Thr
1               5                   10
```

<210> SEQ ID NO 50
<211> LENGTH: 4001
<212> TYPE: DNA
<213> ORGANISM: Brassica napus
<220> FEATURE:
<221> NAME/KEY: Intron
<222> LOCATION: (1892)..(1972)
<220> FEATURE:
<221> NAME/KEY: Intron
<222> LOCATION: (2020)..(2104)
<220> FEATURE:
<221> NAME/KEY: Intron
<222> LOCATION: (2148)..(2208)
<220> FEATURE:
<221> NAME/KEY: Intron
<222> LOCATION: (2264)..(2358)
<220> FEATURE:
<221> NAME/KEY: Intron
<222> LOCATION: (2399)..(2507)
<220> FEATURE:
<221> NAME/KEY: Intron
<222> LOCATION: (2624)..(2755)
<220> FEATURE:
<221> NAME/KEY: Intron
<222> LOCATION: (2832)..(2933)
<220> FEATURE:
<221> NAME/KEY: Intron
<222> LOCATION: (3012)..(3091)

<400> SEQUENCE: 50

```
tgtccgggag gatccaccgg cggtggtcgt tactccattt taacttgatg tcttgaaagc    60
agaggacatg gtatggtggc ggcagaatct atttttagtt gttaattttt cttttcctct   120
gattcttttt attttttcg aatgaactaa ctttgggttt attcagaaga attatcatct    180
aaaaactgat tcaataaaca aaataattta catatttcac aatgagccat tagtaaacaa   240
gtcgaaagtg aaaccaaatg ggaagagaac aatttaata aaaatatgtt ctaatttcct    300 acttttatg aattgaactc ccgaagagaa tggccgaaga acggagtaaa agctcaatga    360
ttgtaaaagc tatgtattct cttgctttga ggaaaaagct ttttgtttgc actcataggc   420
ctgatatgtt gtgatggctc tttacatatt gggtcttttg tggtctatta aacggttact   480
gaagaattag tttatcgcat ttaaaaaaaa atatttgaaa accacatatc taaaatctca   540
atatattatt tattgataga tgaaaagaaa aatagtttat aaaataatat taattggtaa   600
atggaagtca aaattttaca tttaatacat gactagttcg attctccggc tgaaacccat   660
ttaccactga gccaagacca cttgattata tatatcaagc tcttgttttt tgcattaaca   720
aaagttgcat ccaaaatttc aaaacaacaa ctaaattaat gtctttctat tttcaaagtt   780
ttatctccaa acctattaat agtttaattt ttttttttaa aattaggaaa ccggttaaaa   840
tatattttaa atacaaaaaa cttaaacaat gaatcattta tttatttatt cttcaaaatt   900
taaatatccg aacccggccc aaaatatccg aacccgaaca taaatatcc gaacccgact    960 cgaagtgtag aaaatatccg aacgggtttt ataccttat actgaaatac cctatacgaa   1020
cccgaatgtg tatccgaacg cccctacaa tatatgatca tcatttgtat cttgattgaa    1080 caaaaaaaa gttaaactat tgatcacaaa attttcaatg tgagactttt accattttta   1140
gtcatttata gtcgtttta aaaattcaaa atataactta taagaaaaaa tctaattttt    1200
tttattatat gcttaatgtg attgtttaat ttcttttaat aatataaaat taaacaaaaa   1260
atgagaggtt aaaaaaattg ttatcaaata tgtattattc ataatcatta attgtcatat   1320
atatgttaat tatattaggt aatttcgtag ttttttattta agaaaagaaa aaaatattat   1380
tttgtacact actaattaat ttgatagtta gtttaataaa aaatatatta tattattata   1440
tggaccaact tattttctta aaaaaaaacc actgttttaa aaaccaaacc aactataaac   1500
cggagatata ccggattgag tggctaaaac actctttgta tatatgtgct gagcaaaccc   1560
tctgagtgag atggcgtgtt aagaagtagg aggaccattc atgcctctta tgagttgtag   1620
tctgtgtgta caaaaagaa gcgttggtgt gaaagaaagc agaaggattt gaaaatcaaa    1680
aaaattgaag gagaagcggg aaaacaaata atctctccct ccgcttttt ttctccaaat    1740 aatcaatctc tcatttcatt tgttaaccca gttttgat aattatttca aaggggttta    1800
tttatctttt attcctccgg cggcagtaag tagtaatcaa tggcgagaac caaacatttc   1860
gcttccaggg cacgagatcg caatcgaact agttagtact ctctctctct ctgcctttt    1920 tttgatattt attttctagg ttaaaccta atttggcatc tgaaatttgt agatgcgact    1980
gcttcatctt cggcggcggc ggcggaaggt ccgagtgcgg tacgtcatct attttctttt   2040
cccgttttag gtttttacgc aaatctcgtt actgttttt tgacgaatcg attgaaatgt    2100
gtagaccccg acgagaagag aaggcagcca aggagaagct caacagagtg agtctttcta   2160
tttcattttc tgagatccat gaatcctttt catctctcgt gtgttgtgac atgaatcaat   2220
tgcagcagca actcctacta cgactccacc agccggtaga aaagtaagtt acatttccat   2280
ttcacaccat tcatttgctt ctttatcaac aaactgctct ctcatctgtt ttttttgttt   2340
```

| | |
|---|---|
| tgttttggtt ttgtgaagaa aggagggact aagcgaacta acaagctatg cctaaaagt | 2400 |
| tagtgacaga ttttaaaatc tctattttgg atcatcattc tctcaggaca tgtctatttg | 2460 |
| catttgttct tattatgtct gtctgtctgt ctttgtcccc cttgtaggtt ccaacaagaa | 2520 |
| gaagacattc cgttacaagc ctggaaccgt tgccctcaga gagattcgcc atttccagaa | 2580 |
| gaccaccaaa cttcttatcc ctgccgctag tttcatccga gaagttagta atgaactttg | 2640 |
| ttattcatac attcccgctt acttgttttc aatgactctg caattactga tatagaattt | 2700 |
| ggagcaacca ttatggggtg atttctctaa ctacaaatta ctaatactat cccaggtgag | 2760 |
| aagtgtcacc cagatctttg cccctcccga tgttacccgt tggactgctg aagctcttat | 2820 |
| ggctattcaa gaggtacgtg tactccttcc ctcttttgtt tcctattttc cacttgatgt | 2880 |
| ctaatttaaa ctgatcgttt ttttttttata tttcttttgg tgtggggcgg ggcaggcggc | 2940 |
| tgaagatttt ttaattggct tgttctctga tgctatgctt tgcgctatcc atgcaaggcg | 3000 |
| tgttactcta agtaagtagt actccccaaa ataaggaaac ccatttata tacaacattg | 3060 |
| cctcatccat gtctgcttct cttcatatca gtgagaaaag attttgagct gcacgccgt | 3120 |
| cttggaggaa aaggcagacc attgtgatcg tttcgcaggt tgtataactt tgttcactcc | 3180 |
| ttatgtcttg tcatttgtga tctgactgac actttctttt gaaacataac tgcttgattc | 3240 |
| aatatctagg ctgtaaaact tatccctcct tgtttactat cttatatgct ttttccttgg | 3300 |
| aattgatagt ttccattgag atttcacttg cacgaaacat atctgctttc tcaatatctc | 3360 |
| tcagtcttag aaagggctat tgactaaaag aaaagaaaat ttagaggaag atttgtaaag | 3420 |
| acatgtgttt agagagggct taattaaaaa cacacgcttc tgctagcctt gctatttgat | 3480 |
| tcccaatttc aactttttc gaggcatatt ataaagtttt taaatgtact tggcacttca | 3540 |
| acttttataa tttatataac gattttattc taatagagca tttgtgattt catagtgttg | 3600 |
| tcatgaaact caagtaattc acaccgtccg atgttgctat tgtctaataa aatgttgaaa | 3660 |
| aaattgtcaa aacagaacaa aaaacaacat agttgtctct atggtataaa actatcacta | 3720 |
| agttgtctct atagtataat atttttcgca atcccaaaac taattttct ttaatcaaat | 3780 |
| taaacataaa ctaaaaccat ttttaaaaag tttaatggaa aaagataaaa aaataaggta | 3840 |
| atctcgtaat gttttaaaaa ggaaaaaaaa tgtaaaaaca atttaaaaaa aagaacacac | 3900 |
| gacacagatc aaaaatatca tgtaatctaa ttgcatttgg tttctaaaat cttccaaaac | 3960 |
| tattctttta aaattctcta aggtaaaact tgattccaat a | 4001 |

<210> SEQ ID NO 51
<211> LENGTH: 540
<212> TYPE: DNA
<213> ORGANISM: Artificial Sequence
<220> FEATURE:
<223> OTHER INFORMATION: Brassica napus - cDNA coding for CENH3

<400> SEQUENCE: 51

| | |
|---|---|
| atggcgagaa ccaaacattt cgcttccagg gcacgagatc gcaatcgaac taatgcgact | 60 |
| gcttcatctt cggcggcggc ggcggaaggt ccgagtgcga ccccgacgag aagagaaggc | 120 |
| agccaaggag aagctcaaca gacaactcct actacgactc caccagccgg tagaaaaaaa | 180 |
| ggagggacta agcgaactaa acaagctatg cctaaaagtt ccaacaagaa gaagacattc | 240 |
| cgttacaagc ctggaaccgt tgccctcaga gagattcgcc atttccagaa gaccaccaaa | 300 |
| cttcttatcc ctgccgctag tttcatccga gaagtgagag tgtcaccca gatctttgcc | 360 |
| cctcccgatg ttacccgttg gactgctgaa gctcttatgg ctattcaaga ggcggctgaa | 420 |

```
gatttttaa ttggcttgtt ctctgatgct atgctttgcg ctatccatgc aaggcgtgtt      480
actctaatga gaaaagattt tgagcttgca cgccgtcttg gaggaaaagg cagaccattg      540
```

<210> SEQ ID NO 52
<211> LENGTH: 180
<212> TYPE: PRT
<213> ORGANISM: Brassica napus
<400> SEQUENCE: 52

```
Met Ala Arg Thr Lys His Phe Ala Ser Arg Ala Arg Asp Arg Asn Arg
1               5                   10                  15

Thr Asn Ala Thr Ala Ser Ser Ala Ala Ala Ala Glu Gly Pro Ser
            20                  25                  30

Ala Thr Pro Thr Arg Arg Glu Gly Ser Gln Gly Glu Ala Gln Gln Thr
        35                  40                  45

Thr Pro Thr Thr Thr Pro Pro Ala Gly Arg Lys Lys Gly Gly Thr Lys
    50                  55                  60

Arg Thr Lys Gln Ala Met Pro Lys Ser Ser Asn Lys Lys Lys Thr Phe
65                  70                  75                  80

Arg Tyr Lys Pro Gly Thr Val Ala Leu Arg Glu Ile Arg His Phe Gln
                85                  90                  95

Lys Thr Thr Lys Leu Leu Ile Pro Ala Ala Ser Phe Ile Arg Glu Val
            100                 105                 110

Arg Ser Val Thr Gln Ile Phe Ala Pro Pro Asp Val Thr Arg Trp Thr
        115                 120                 125

Ala Glu Ala Leu Met Ala Ile Gln Glu Ala Ala Glu Asp Phe Leu Ile
    130                 135                 140

Gly Leu Phe Ser Asp Ala Met Leu Cys Ala Ile His Ala Arg Arg Val
145                 150                 155                 160

Thr Leu Met Arg Lys Asp Phe Glu Leu Ala Arg Arg Leu Gly Gly Lys
                165                 170                 175

Gly Arg Pro Leu
            180
```

<210> SEQ ID NO 53
<211> LENGTH: 3088
<212> TYPE: DNA
<213> ORGANISM: Sorghum bicolor
<220> FEATURE:
<221> NAME/KEY: Intron
<222> LOCATION: (377)..(487)
<220> FEATURE:
<221> NAME/KEY: Intron
<222> LOCATION: (514)..(618)
<220> FEATURE:
<221> NAME/KEY: Intron
<222> LOCATION: (662)..(1094)
<220> FEATURE:
<221> NAME/KEY: Intron
<222> LOCATION: (1217)..(1312)
<220> FEATURE:
<221> NAME/KEY: Intron
<222> LOCATION: (1391)..(2087)
<220> FEATURE:
<221> NAME/KEY: Intron
<222> LOCATION: (2164)..(2556)

<400> SEQUENCE: 53

```
catctctcac tgccatccgg gtccactact cccaacgttc ggcacgccag gtatagccgt      60
taccccggta ggccccactg gtacacggac aaaggttagc ggtcaccgcg aatcgtgaat     120
```

```
acttgtgact acggggtgct aattataaaa acgccgcaca tcctttcgtt tcgccatttc      180
accccccttc ccttcccgta gagaggaaaa aaacccaccg tcgacccgcc cggccgcccg      240
agagttctga atcgaaaccg tcggccgcga ccgcgagagc agcgcggggc gcccaccgtg      300
atggctcgaa ccaagcacca ggccgtgagg aagctgccgc agaagcccaa gaagaagctc      360
cagttcgagc gcgcaggtaa gcccgcgtcc ccgcgctgaa ccccctccg cctcgcgagc       420 agacgctgcc gctgctctcc gtcgcccctg gtgctaagcg cgttccttttt ttttccttct    480 tttgcaggtg gggcgagtac gtcggcgacc ccggtgagtg cgtgcgtgcg tgcgggaatt      540
ggttttagcc ctccttttgc ggtttcgcct tttgttgggc tggtctcact tgcttgcaat      600
ctgtttgatg gaatgcagga gaggaggaat gctgggaccg ggggaggagc cgcggctcgc      660
ggtgaggatc tctttgtcgt tgctgggttt gggaatttcc ggcgcgaaat tatgtggatt      720
tctaggttta tctgccgtct ttcttcttgt cttctctttt ggctctgggg tgagaagtta      780
gggtggttgg gcggacatgg tgcgttattt cgccgtatcg tttggtttgg tgctttctca      840
tccttttaat tccaacatgc cttgtaaaaa ttgcacaaga tttgttttttt catgcatgtc     900 tcagtgttgc taatttgctt ttccggttcg gttggtagaa ttcaatttct ggcgcaata       960 tgcatcttct tttgttgcaa catgagggcg aatgtgccag ttccatatgg gcgtcgcggt     1020
tttgaagtta ctaccttgct tgctcttcgt attataggcg tcattcacaa tagtatgttt     1080
tcttggagat gcagttgcac gggggcgtgt ggagaagaag catcgctggc gggcagggac     1140
tgtagcgctg cgggagatca ggaagtacca gaagtccact gagccgctca tccccttgc      1200 gcccttcgta cgtgtggtgg gtgcatcttg taccaattgt tgtccactcc atagaatggg     1260
tttgttctgc agtctgtctg atggaaagtt attcttctga gaaaaatgc aggtcaaaga      1320 gttaactgca ttcataacag actggaggat agggcgctac accccctgaag ccctccttgc    1380 gctgcaagag gtcagttatg aaacatgtct tgtgtatcag ttaagatcat cttctataga     1440
cataattgtt atcatgaagt ctttttctgt taatcggtct ggtactactt aataatcagg     1500
atttcagatt gctgcctttc ctagtggtgt agtcaaaagg gaatttaagt gctgttaggt     1560
actgtttgtt ttggtgtttt gaaccctgcc gcgatcggtt ttgttattc catgtttgtt      1620 tctgtggcag cggacgttca cggtgagatg ggatacgggc gtgtgaaaca tagttacggt     1680
ccatcttcat ggcttatcca tttacgctgc tcgtccgctc acttgttatg tgcggcaacc     1740
aaacttttgt tactagtgta actggtagcg ttgcaaatct ttccatttgc gttaccactc     1800
cctatgggag ccaaacagca ccttagtgta gattccattt gtattacttg agctagcttc     1860
cttgctattg gtgcctcgat tgtactgtta tgatcgaagt gctgaaaact ttgtcgcctg     1920
catagcatga ttagagaact tgagtttaca tttattcaat accttaagac tgcatttcgt     1980
atagataaat tattttcct aattgttctg gttaactgtt ttaggtttcc atattttgt      2040 atgtgtatca tttaaattat tgtgttgttt ttcctcctg tctacaggca gcagaattcc      2100
acttgataga actgtttgaa gtggcgaatc tgtgtgccat ccatgccaag cgcgtaacag     2160
tcagtaagtt atcactgaat gaactccttt tcctctgtac tattacgcct aatggagatg     2220
tgtgatgcat ttttggttac acgattcttt agtgattctg cttcagttgg atatgataaa     2280
tctagatgtt atttaaagtg gcaaattgct tacgagtgga aatagtaatg ttcaaatagt     2340
gaaaagtgca attaaacttt taataggcca ttatatggtt tgattgtcaa caaatgcatc     2400
aagaaatagt aaatattata acagttatgg cttagagagt ggacaaaaaa tcggtaatgg     2460
tgagctttgt ataaacacta aaactggctg agaaatctga taactcaagg atctataggaa   2520
```

```
aatgtattat cctaaatgtt ttccttcctg ctgcagtgca aaaggacata caacttgcaa    2580
ggcgtatcgg aggaaggcgt tggtcgtgat atccattctg attctgatta ccttgttcgg    2640
gtggaatttg tttagaggag ttagacatta gtcttgttga atgctgtgca tggttcctaa    2700
tctgtttcac agttagtggg ctcttctggg atgatctgtt aacacctgtg gagtatgtta    2760
tgtaggaaac acctgaactg aacaacccaa agttgttttg gttgctcttc aaccatttgt    2820
ttgcttcaga gatcgattct aaactgcatg ctaattagtc tatggttgaa caaaaattat    2880
caaatataaa tgaaagtgat atagtagcaa aatccaaaaa aaaaggatc caaacaaggc     2940 ctaaaatcat ggttctttct cctttttgaac tgggtgcaag tatggacagg cacagaagaa    3000
aaccgcctag caaaccgttt gttttttttt cttcgttgta ccacacgaca ctgttcgttc    3060
ctagttgcgc ctttttgttg tagaagtc                                       3088

<210> SEQ ID NO 54
<211> LENGTH: 471
<212> TYPE: DNA
<213> ORGANISM: Artificial Sequence
<220> FEATURE:
<223> OTHER INFORMATION: Sorghum bicolor - cDNA coding for CENH3

<400> SEQUENCE: 54
atggctcgaa ccaagcacca ggccgtgagg aagctgccgc agaagcccaa gaagaagctc      60
cagttcgagc gcgcaggtgg ggcgagtacg tcggcgaccc cggagaggag gaatgctggg     120
accgggggag gagccgcggc tcgcgttgca cgggggcgtg tggagaagaa gcatcgctgg     180
cgggcaggga ctgtagcgct gcgggagatc aggaagtacc agaagtccac tgagccgctc     240 atccccttg cgcccttcgt acgtgtggtc aaagagttaa ctgcattcat aacagactgg      300
aggatagggc gctacacccc tgaagccctc cttgcgctgc aagaggcagc agaattccac     360
ttgatagaac tgtttgaagt ggcgaatctg tgtgccatcc atgccaagcg cgtaacagtc     420
atgcaaaagg acatacaact tgcaaggcgt atcggaggaa ggcgttggtc g              471

<210> SEQ ID NO 55
<211> LENGTH: 157
<212> TYPE: PRT
<213> ORGANISM: Sorghum bicolor

<400> SEQUENCE: 55

Met Ala Arg Thr Lys His Gln Ala Val Arg Lys Leu Pro Gln Lys Pro
1               5                   10                  15

Lys Lys Lys Leu Gln Phe Glu Arg Ala Gly Gly Ala Ser Thr Ser Ala
            20                  25                  30

Thr Pro Glu Arg Arg Asn Ala Gly Thr Gly Gly Ala Ala Ala Arg
        35                  40                  45

Val Ala Arg Gly Arg Val Glu Lys Lys His Arg Trp Arg Ala Gly Thr
    50                  55                  60

Val Ala Leu Arg Glu Ile Arg Lys Tyr Gln Lys Ser Thr Glu Pro Leu
65                  70                  75                  80

Ile Pro Phe Ala Pro Phe Val Arg Val Val Lys Glu Leu Thr Ala Phe
                85                  90                  95

Ile Thr Asp Trp Arg Ile Gly Arg Tyr Thr Pro Glu Ala Leu Leu Ala
            100                 105                 110

Leu Gln Glu Ala Ala Glu Phe His Leu Ile Glu Leu Phe Glu Val Ala
        115                 120                 125
```

```
Asn Leu Cys Ala Ile His Ala Lys Arg Val Thr Val Met Gln Lys Asp
    130                 135                 140

Ile Gln Leu Ala Arg Arg Ile Gly Gly Arg Arg Trp Ser
145                 150                 155
```

<210> SEQ ID NO 56
<211> LENGTH: 5834
<212> TYPE: DNA
<213> ORGANISM: Zea mays
<220> FEATURE:
<221> NAME/KEY: Intron
<222> LOCATION: (1820)..(1917)
<220> FEATURE:
<221> NAME/KEY: Intron
<222> LOCATION: (1944)..(2035)
<220> FEATURE:
<221> NAME/KEY: Intron
<222> LOCATION: (2085)..(2239)
<220> FEATURE:
<221> NAME/KEY: Intron
<222> LOCATION: (2356)..(2446)
<220> FEATURE:
<221> NAME/KEY: Intron
<222> LOCATION: (2525)..(4530)
<220> FEATURE:
<221> NAME/KEY: Intron
<222> LOCATION: (4607)..(5346)

<400> SEQUENCE: 56

```
ttatgtagag gcaattgcag tagtgcctct gttttagagt gtaactacag atttgtccct    60
atttttttag agtttgcgtg tttgtccctg tttttttcaaa tcaaactatt gtataccct   120
actccattag ttatacttaa caatgttaag tcttgataaa aagacaaggg ataattggat   180
tagtgaccct gttttagagt gtaattatag ctttgcccga tgttttagac ttcacatgtt   240
tttatgacaa ttcaaattgt ttccataaca tcttaaatta ttttgacaac atttagaatt   300
gttttgcaat aatttaaatt attttccaaa taaaaatatt ttgacaatta ttttatcaac   360
aaattaaatt attttttta caaaataatt tgtcaaggta cttttttaaa attttgaaaa   420
taatcaaatt attgtaaata taatttgaat tgttgcgaaa ataatttgga ttgtcataaa   480
aacacgtaag tctaaaaatt aggcgtaaaa ctacaattat actctaaaaa ggtggtaatg   540
gcgtagttgt tccttgtcta ttttatcaag acatagcacc gtgcagtaca actaatggag   600
tagtgacata caacaatttt gttttaaata atagggtaa atacgcaaag tctaaaaaac    660
agaggtaaat ctacaattac atgttaaaat agaggcatcg atacaattgt acctttata    720
tagcagcatg cgccctgttg ggatacaatt gtacctttca catgtcttct agatggttcc   780
caaccctttg gccaagatcg tacagataat attgcgagga gcccaaatca acggtgtcca   840
tatgttatgt tgatgtggat ggtttaccta ggcgcaaaag tgcgctggtt tcgtccgtac   900
aaatatactt taagtatggt tttgattttt ttctatttt cattttttaa ataaaacgag   960
acaatcaaat ctgatataaa aatcaaatga attataaata gagacggaaa gagtatatat  1020
atttgttttg ctattatta aagtattaaa agatagtgga cgaatgaacg tcctctatgt  1080
ttaaaagaac gttttagagg acgttgtgtt gttgaaggaa atatgaaaaa aaaatcttct  1140
gcatatttag aagggaggag cgtttacaca ttactttcgg gacttcaacc caaatatgtc  1200
aaggtttgtg agtggctcag tgcggaaaaa aaatcctata taccagat gtaaacacta   1260
tcttttacag cctatcacat tcacatttag aggttcacaa agatagatca aaatttataa  1320
aataatcatt taatatttt tttatttat ttatatggat aagcagctgg tgtatgtgag  1380
gagctgtaaa agatatttt tacatccgag atgtaaagat tttttttaac tcaatgctgg  1440
```

```
ttaccggctg ggaggacgat gataaagaaa gcatctctca ctgcattccg ggcccactac    1500
tcaaacgttc ggcacgccag gttggcaggt agccgttaca tcgataggca ctcggccact    1560
cgcacgcaga caccacacca gtgtgctcag tgctcactgc tcaccataat aacgctgcac    1620
ctcttttcat ttcaccatct cctgcccct taaaaaaaag actcaccgtc gacacgccct    1680
cccgtcccga gagttctgaa tcgaaaccgt cggccacgag agcagtgcga ggcgcccacc    1740
gcgatggctc gaaccaagca ccaggccgtg aggaagacgg cggagaagcc caagaagaag    1800
ctccagttcg agcgctcagg taacccgggt cccgcgctcc ccccgcttc gcaagcagac     1860 gctgtcgctt ctctccgacc ctggtgctaa gcacgttcct tgttccgtct tttgcaggtg    1920
gtgcgagtac ctcggcgacg ccggtgagcg cgtgcgtgcg gggatcagtt ccctcctttt    1980 gcctttttt gttgggctgc tcttacttgc ttgcaagctg tttgatggaa tgcaggaaag     2040
ggctgctggg accgggggaa gagcggcgtc tggaggtgac tcaggtgagg acctatttgt    2100
cgttgctgga tgctgggttt cgcttgcaat ctaattttgt tgcaagatga gggcgaatgt    2160
gccagttcca tgtgggtgtc atggtctcgg agttactacc ttaattgctc accatagtat    2220
gttttcttaa aaaaaacagt taagaagacg aaaccacgcc accgctggcg gccagggact    2280
gtagcgctgc gggagatcag gaagtaccag aagtccactg aaccgctcat ccccttgcg     2340 cctttcgtcc gtgtggtggg tgcaggcgtg tttgtcctct gcatagtatg gggttgttcc    2400
gcattctgtc taatggaaag ttattcttct gagaaaaaaa atgcaggtga gggagttaac    2460
caatttcgta acaaacggga aagtagagcg ctataccgca gaagccctcc ttgcgctgca    2520
agaggtcagt tatgaaaaat gtcttatctc tctgttaaga tcctcttcat atacatagtt    2580
gctattgcta tcgtgaagtc ttttttttct gttaattggt ctggtactac ttactagtca    2640
ggatttcata ttgcggtttt tcctagtggt gtgtagttaa aaagtagttt aattgctttt    2700
agttaaaagg ggtgttcagg gctaaagatc aactatgaga aaacagaaat tttcccaatt    2760
cgatacccga cagcattatg gcctgcgcta atggaggtgt ttccgggcaa atactctagc    2820
ctacctggga agtaccttgg gttgcccctt catttcagga agtaaaaag gaatgatctt      2880 caacctctaa tcgaaaaaat caacaacagg ctggccttgc tggaaaggca agatgttgtc    2940
caaggctggt atagaaactc ttgtaaaatc gatgctatcc gcacaaccaa tctaccatct    3000
aatggttttt ccacctcaaa aatggctgct gcaaacaatt gacaaaatac gaagaaactt    3060
cctgtggaga gggagcaatc cagaagtttg cagcggggt cactgcctcg tcaactggcc     3120
cgtaacttgc ctcccaaaga acaagggagg tcttggaatt ctggaccttg atcgttttgc    3180 gaggggcta agactaagat ggctgtggct acgatggaag agcaaagata gggcgtggac      3240
tgccttgaag cttccttgtg acaaaactga tgaagatctc ttcaatgctt ccacaactgt    3300
cacggtaggc aatggaaaga tagctgaatt ctggaattct agttggatcc aaggccaagc    3360
ccctaagaac attgcgccaa cactgttcaa gaaggaaaag aggaagaaca tcacggtcgc    3420
caaagcgctc actaacaaca attggattcg tttatgctca ccatacacgg gtgaggggga    3480
gtttagagag gtcgtctctc tttggcaggc cataggtaac atgcaagagc ttaacggttt    3540
ggaagacaac atctccttgga gatggacggc agatgggcag tacagtgcta gcagtgcata    3600
caaaatccag ttcgcatcca atttcactaa aatgaacctc tgccctattt ggaaggctaa    3660
agtggaaccg aaatgccgat tttttgcttg gacactactt cataagagaa ttctgactgc    3720
cgataacctt cataaaagag gttgcaactc agcctcagaa acaattcccc acttatgcaa    3780
```

```
ggattgcccc tttagtagag aggtgtggaa caaagttttg tctcgggcca acttccttt     3840
actgactggg tctcccagtg acacttcttt gtatgattgg tggacggaca tgtgcagcct     3900
ttgcagcaga caggcaagaa gaggtttcga cggtctgcta tttcactttt ggtggaactt     3960
atggctggaa agaaataaca gaatctttca aaggcagcgt agaagtgtag atcaagttgc     4020
tctggcagtc aaggattatg ctagtagctg aagtctagtt ggtttggact agtggttttg     4080
ttgcttttct ttttaatttc tttttagttc tttttatgtt gttttcgttt ccttaagttg     4140
cttggagtct gtattatcct cttcttcta atatagatcg gagcgacaaa ccttttgccc     4200
cttcctttca aaaaaagtt aaagggaat ttaactgctt tcctagtggt gtagttaaaa     4260
tggatttcat attgcggcct ttcctagctt gcttgctatt gattggacta tagtgatcca     4320
aatgctgata actttgtcgc ttgtgtaggc atggttagag agcttagagt ttgcattat     4380
tcaatacctt gagactgcat ttcatataca taaattattc atgattattt cttttctcta     4440
tttgttctgg ttaattaaga gttttaggtt tccatatttt tgtacgtgca tcattaaat     4500
tcttgtattg ttttcgttc ttgtctacag gcagcagaat tccacttgat agaactgttt     4560
gaaatggcga atctgtgtgc catccatgcc aagcgtgtca caatcagtaa gttatcactg     4620
agtgaactcc ttttctctg tagcattact cctaatgaat atgtgtgatg cattttggtt     4680
gcacgattct ttagtgattc tgcttcagat ggatatgata aatctagatg ttattttgaa     4740
gtggcgaatt gcttacgagc ggaaatagta atgttcaaat agcgcaaagt gcaactgttg     4800
acttttagta ggccatttat atggtttgat taccaacaaa tacgtcaatc atatgatttg     4860
attatcaaca aaggaatcag ctatatggtt tgattatcaa caaggaatc agctaggttt     4920
gcttatcaac attcaacaaa ggcatcaagt aatactccat ccgttcaat ttataattcg     4980
tttgactttt tttatctaag tttgatcggc tcgacttatt aaaaaaaatc ataattattg     5040
ttaattttg ttgtgatatt gtttagtata atatacttta aatgtgactt tgagttttc     5100
atttttcgc aaaaaaaaat gaataggacg agccggtcaa acgtgacaca aaaaagtcaa     5160
acgaattata atttgggaca cacggagtag taaataatgt aacaacttag agagtgggac     5220
aaaaaaatct ctagtggtgc taaatttagt tcagctttgt ataaacacaa gcattgattg     5280
agaaatctga caactcaagg atctgtagga aatgtgttac cctaaatgtt ttccttactg     5340
atgcagtgca aaaggacata caacttgcaa ggcgtatcgg aggaaggcgt tgggcatgat     5400
ataataatc cattctgatt gcatcattct tgtgaatttg tttgtaggag ctagacatta     5460
gtgttgttga atgctgcatg gttcctaatc cttttcgcag tctaacatct gtggagttag     5520
tatgttacat ggcaacagct gaacatctgt ggactatatg gcaacagccg aagattgtgt     5580
ctgtgggata actggttgtt ttggttgctc ttcagtagtt tgtttgcttc aggtaaccat     5640
gctgcgaact atgatgttt cattctcggt ttgcttcagc taaccgagat cgattcagtc     5700
tgcagtatgg actatggagt aaactgcatg ctgaaacccg aaccactgct gaaactgcat     5760
gctgaaaccc gaaccactgc tacggcagtt gccaggatag caggagggcc tttatgcaca     5820
gtggaattga gtag                                                      5834
```

<210> SEQ ID NO 57
<211> LENGTH: 471
<212> TYPE: DNA
<213> ORGANISM: Artificial Sequence
<220> FEATURE:
<223> OTHER INFORMATION: Zea mays - cDNA coding for CENH3

<400> SEQUENCE: 57

```
atggctcgaa ccaagcacca ggccgtgagg aagacggcgg agaagcccaa gaagaagctc      60
cagttcgagc gctcaggtgg tgcgagtacc tcggcgacgc cggaaagggc tgctgggacc     120
gggggaagag cggcgtctgg aggtgactca gttaagaaga cgaaaccacg ccaccgctgg     180
cggccaggga ctgtagcgct gcgggagatc aggaagtacc agaagtccac tgaaccgctc     240 atccccttg cgcctttcgt ccgtgtggtg agggagttaa ccaatttcgt aacaaacggg      300
aaagtagagc gctataccgc agaagccctc cttgcgctgc aagaggcagc agaattccac     360
ttgatagaac tgtttgaaat ggcgaatctg tgtgccatcc atgccaagcg tgtcacaatc     420
atgcaaaagg acatacaact tgcaaggcgt atcggaggaa ggcgttgggc a              471
```

<210> SEQ ID NO 58
<211> LENGTH: 157
<212> TYPE: PRT
<213> ORGANISM: Zea mays

<400> SEQUENCE: 58

```
Met Ala Arg Thr Lys His Gln Ala Val Arg Lys Thr Ala Glu Lys Pro
1               5                   10                  15
Lys Lys Lys Leu Gln Phe Glu Arg Ser Gly Gly Ala Ser Thr Ser Ala
            20                  25                  30
Thr Pro Glu Arg Ala Ala Gly Thr Gly Gly Arg Ala Ala Ser Gly Gly
        35                  40                  45
Asp Ser Val Lys Lys Thr Lys Pro Arg His Arg Trp Arg Pro Gly Thr
    50                  55                  60
Val Ala Leu Arg Glu Ile Arg Lys Tyr Gln Lys Ser Thr Glu Pro Leu
65                  70                  75                  80
Ile Pro Phe Ala Pro Phe Val Arg Val Arg Glu Leu Thr Asn Phe
                85                  90                  95
Val Thr Asn Gly Lys Val Glu Arg Tyr Thr Ala Glu Ala Leu Leu Ala
            100                 105                 110
Leu Gln Glu Ala Ala Glu Phe His Leu Ile Glu Leu Phe Glu Met Ala
        115                 120                 125
Asn Leu Cys Ala Ile His Ala Lys Arg Val Thr Ile Met Gln Lys Asp
    130                 135                 140
Ile Gln Leu Ala Arg Arg Ile Gly Gly Arg Arg Trp Ala
145                 150                 155
```

<210> SEQ ID NO 59
<211> LENGTH: 8441
<212> TYPE: DNA
<213> ORGANISM: Beta vulgaris
<220> FEATURE:
<221> NAME/KEY: Intron
<222> LOCATION: (99)..(203)
<220> FEATURE:
<221> NAME/KEY: Intron
<222> LOCATION: (245)..(331)
<220> FEATURE:
<221> NAME/KEY: Intron
<222> LOCATION: (344)..(488)
<220> FEATURE:
<221> NAME/KEY: Intron
<222> LOCATION: (591)..(3263)
<220> FEATURE:
<221> NAME/KEY: Intron
<222> LOCATION: (3339)..(4377)
<220> FEATURE:
<221> NAME/KEY: Intron
<222> LOCATION: (4458)..(8130)

<400> SEQUENCE: 59

```
ctactctttc tctctctctc tctctccatt tctgtttgaa atcatgagag ttaaacacac      60
tgctgccagg aaatcaacca ccaacggtcc tcgttcaagt tagtttcctc tctcttcttc     120
ttttttgttc gcattctctc aatctatatt tcaaatttga aaaaaattgt gatgctcata     180
aaccctaaaa ttttcttgta cagaggctca gaaatctccg cgcagtttgc aatcaccaca     240
atcggttctc tctttgtact tttgatttgt ttttccttca tttgttcgat gaatggctct     300
taattgtctt ttatttactt gaaaattgca gccttctagt agttcaaagc gcaaatcact     360
cagaaacact gatgcaactc ctcaaagtaa cttttctttt aatattaggt ttaattttac     420
tgctgtttgc caaattctgt tgaaattgta aaatattttt tttcttaaat ttgacggttt     480
cagagaagaa ggcttaccgc cgtaagccgg gcactgtggc actctgggaa atacgcaaat     540
ttcagaagtc attcaagccc ttgattcctg ctgcgccttt cattcgaaca gtatgtattt     600
tttttgtttg tacttaataa atgaattttg gactggtgtt tgtgtggctg catagaaata     660
tatttccata caactgaaat tgtcctagga ggtatcgatg aatgtttgct acaaaataaa     720
taaatataag tgattatatc ttgttaaaaa gccattataa ttgcaactta tatgtatgtt     780
gtaatgaggt caactagcta ttttgtgcaa agtcacccac actttaacat aattttgtgc     840
tctcgtaacc ttaaaaaaat ataagtaaag ggttgatttg gtctaattag agctgatgaa     900
acccaattag attgaaacat aaggtgaaat caggtggtga tcagcttcaa ttagatctaa     960
taagtgcagt ttagtttagc ttcggtgaaa tgaacacacc cttaaagata gaaaatcgac    1020
actatatatg gtccttttta gatatgatag ttcgatattc tgttttgggg tgtgttgaat    1080
gattaaatgg agtggtgaat agctgatggg aactagagaa gatgctcagt agacagttat    1140
tgtggagact atattactga ttacccctgt ttctgagtgg ttaggacaat gtgacaattg    1200
attttgggta ttatttgtag atgttttttct ttttgttaaa agtgccaaga taggtgtgca    1260
gttgctgatt ctcagtttgc taagaattag ctgtgtctgt atttcgtacc tcagttgatt    1320
ctaagtgaac atttctttga attgatgctt tgttcttgca tcatgcaact tggtgaagct    1380
ttcttgtagt tgctccagtg gcaatctagt ctggtatgtt tagaactctt gtgatggtat    1440
gagttcatca agatattggt gatccaatta gcctaaccaa tgttttttac ccctattgt     1500
cactgactta tactccctta tctataaaaa taattgtgac attgatccat ctcctcacaa    1560
tcattaatat tatatgtact gaccatcttt acactctcaa cactgaatct aagtagggga    1620
attttgggaa attcaatgat gaactagtac accttcttc ccaataatat tgttgacctt    1680
tttattttga tttgtcccat attgtcctct ttggtaattt aatgtatatt cacccaattt    1740
tcttttcaat acccactata ccaacatata attggttaat tcattttat taattatatt     1800
tcctaagagc ttgttgtgta aacgtggatg aatttgtagg catggatgaa gtattgttat    1860
aatgaggtga caacattact taatttcgaa ctgagggaca gagggatatg atgataaaac    1920
aactttgct tgcttcttaa actcagaaga tagggtttac accaagtggc atgtaaaagt    1980
cactagatga ttatctatta caagggcttg tacaatctga agtacgatag gatttgaagt    2040
taacaacatt catcgaaagc tcataacttg tccttatatc aatataagtt gctggcatgt    2100
gaaattgcgt tgcaagcatc catgagctag ctcaactatt aactattaaa ctttatattt    2160
ttgcttgatc tagtatgagt cctactattt agtttctcca tctacctaa tatgtcgcat     2220
acaccaacta atcattatcg ctagaatcaa taaacaaagc tttctttcct taggtgtatt    2280
agtacctagc tcctgtaata ccaagagcac ccaaatgggg aagaaaaagt agaattggct    2340
```

```
catatctcta atcctacatt gatcattgaa aaggacctta aggttctcat actgaaacat      2400 catcttttg  agcaggatat ctacgtagac gacaagaaag actactttgg ttgcccgtgc      2460
atttgagtgc atcagacaac ttctttacca ctgtctaacg gcttgctttg gccatattgt     2520
ggtcttctat gccaaaatta atgatatttc ttggcaccgc gctaatgata ttactgaatg     2580
cggatatcgt acgattagaa tttattcaaa gtaggtagca attactagtt ttgagcattg     2640
agtttcaata attagtaaat taagtgctaa acttgtacat tttggctaca tgtatttgaa     2700
ttagaattgg tacgaggaaa tatagcaaca ttacgggcaa tgttcactca agtagaagcc     2760
attacatcaa atagtactag ttgaagtatt agttctcata atactaatca ttgtcattaa     2820
tggaatattg aacgtaaat  gcctttaagg tgctgtagtt ttagtagaaa ttctactatt     2880
ctagtatgat aatgcaattt attgaaactg tttgtaagat agcttggatc ccacatcagt     2940
cttgatgcta aataaatgga tgtccataat cttctaatct ttaatttgtg tctcttacca     3000
aacgagaaaa aataggagaa atccaatttg catgacctca ataaggaaat gttgttaatg     3060
tgtgatgctt gtttctcatt tatagtctag agagagttat catgtccaag attgcagtct     3120
tggtactgag aaagtttgat tgttggttgg ctgcttcttg agcctctttt ttttagagta     3180
agacacttcc tagatataat tttctttatt tttttgtaaa ttccatatat actactacat     3240
taacaggttt aagtttatat taggtgagag agattactca ccagtttgct ccttatgttg     3300
gtcgttggca agctgaagct ctgatggccc ttcaagaggt gcagaccaac tcttttagcc     3360
tttttttttc tggcatgtca agtgtggcta ttagatttc  tgtgtgattc tcactcccat     3420
atatctatat atgtacatat taaagcacat tgatacctat cttgtcagat gtggtctttt    3480
caattctttt ctaagttgag attcttctct tggtcgtaga tatgctcctg ccgaaatata     3540
ctgctgtctt gttatccatc atgacttggt tatgcttgta tctgggcatt atcttggcat     3600
gcttaaaaac aagtattgaa cgagcctcct attgataaat tttactatta atattggatg     3660
gcttctcaaa ttctaatggc agtgagatac tgttaagttg ggagaaatag attaagaaac     3720
agaaagatgt ttaccatgag agcaattgaa atagaaaata gagtaacttt ttgcaaagat     3780
tttggtcctt tagattgttg aatactacct gataatgaag cattttctaa atttatgtgc     3840
tttctatcta tcagatactg gaatacaatc aaattcctat cacgtactga gcattgtgat     3900
cagattcttg cttgcttcct atcacatact ggaatccttt tgattgttga atacaaagat     3960
aatgaagcat tctctaactt tatgtgctgt aactacttat aatgattctt gcttgcctcc     4020
tatcacgtac tcaaatcctt tgtttgattt gtctcttata agaggaactt cctgtctttc     4080
tttgtcatga cttagtattt atagaggtgc aacttatgg  ccttgacaac tgaagctttt     4140
atgcaaactc cggattttgt tgatggaagt acaagtaaca ctttagcatg tggattcagg     4200
tctaacggtt aagactttt  aatgaatgtt ttaactgtag tagtttattg atataaaaaa     4260
agtggtctct caaactttt  atgagatcat atcgaagtaa tcaaatttat gattcaggtg     4320
cttctgctat tattcttggt taagcatgtg ctattttga  cagtctgtca attgtaggct     4380
gcagagaatt ttattgtccg tttgtttgaa gatggtatgc tttgtgcaat tcatgccaaa     4440
cgagttacac tcagtgagta tctgatttcc ttcggtggtg ctgctattat gcattatata     4500
cactttgcct caatatcgtt atataaggag tccttgtttt catatttgtt tgatgcatat     4560
gttatatcct gtttagtggc tgctgcagtt gtgaacttac ggcctgtttg attagtggtc     4620
ataaatgatg gtaatactaa tataatttag tataaatttg taaaaaaaat gctaatatca     4680
```

```
atatttatgg taatgaaatt ttatcataaa acatgagttc tcttttataa gttttcatta      4740
ctatccaata ccaccttccc aagtggtaat gaacggtaat gaaattttag gaagaaaatg      4800
gatatttggg gattagatag cattaccatg ggtaatgaca tgagattttc tttacaactt      4860
tatactacga tgcattatca ttaccaccat ttatgaccca taaccaaaaa aaccataatg      4920
tgttaggttc attttttcatt tttctaataa tttgcttcat gaattttttc tggagatatc     4980
ttatctagat atttcttgcc aacatgtttc acctgataat tgatcgattt aatagttcag      5040
aactttccaa aaactatgct gctcggtgtt ggctgtcatc catcagttta agaaaactat      5100
tgacatgatt taagcctcgt cctgtactac taggaagggt aaactattgt tgcttccaaa      5160
aatgtctttt aagggcgtgt tcagcaacaa tagttgtagt agtagctttt agctgttagt      5220
tgtgctcgta gctgttagtg gttagtgtgt aactgttagc tgttcaagta gcggtataag      5280
atattgatgt tcggtaaaag aagctgtcaa aatagctgtt tacaaagaat taataaaaaa      5340
ctcaaacaaa gctttaatat ataatttatg caccactaaa gctaccccaa aagctacaaa      5400
ttgtagcttt ttacaaacac tactaaaaca ctacttgtaa cactaaaagc tacttatact      5460 actatttgc caaacattat tatttttct taattagtgt tttgacctag tcaagacact        5520
aaaagctact tgaaaagctt ttgccgaaca cgcccttagt agacaagagg ggggaggggg      5580
tcatcaagaa aatatgatta tactctcaac aaaaaaaaaa tgtaacttaa aaaaaataaa     5640
aataaataat tgactacttc aattaagaaa agaatagaat aaaaacatta cagtggatgt      5700
ctcatccaca tccctaattt aatggcacaa tagaataatt gttttaaatt ttagaaatta     5760
caacacaaga tgtaaattac tcttatcttc ctcttcgtaa tcttttttact cttcctttac      5820 ctcttccttt acctctacat aaaatagaga attagagatt gattaagata attataagat      5880
tttagaaaca ttggttaaga aattcttcaa caaacatat caagtaactc cattatttta      5940
gtttagtgac ttgctattta tcaccctaat ttcaccatct accgccctcc ttggacaata      6000
ttgccccttc cactttcttc actcttcctt cctcacgcat cttatcatct ccttccacta      6060
tcacctttaa aaaagtgtgt caggcacaac aaaaacgctt ttatcaaccc acgcgaggcg      6120
aagtacgtca ggcgcaacaa ggcgcgcacc taattctgtc ttttgccaag gctgatggtg      6180
cacttagttt taaaaagcgc agcaaagatg tgcctaggcg caaggcggtg aaaaaattgc      6240
atccgtcagc agcggagtag aggctcacaa caataggtgc gaagaggcgt gcacgtacaa      6300
aagaagcaaa aataagaaac tcaaatatga gacccagtgt ttaacatgta aattcgatac      6360
ccagtgttta acatgtaaat tcgattaaaa gccccttaatt aattgcatga aattaattca      6420
ttttaaccta tactaaaagc cctaatatta gaaaatccta gtttgcaggt tgaggaattt      6480
ggaaaattga tgattgttgg atttgaaaaa attgttgccg gcgatgaatg tgaggtggtt      6540
tatggcacta gagaggttgg cgttcgttgc cgatgaagct ttccaaggtc attctctcct      6600
tgtcttcttc ctatgcctag ctctcttccc tctccttaat cttctcttct tttctattct      6660 ctctcttttat cactacatta tgtttatttc tcgttcttcc cctatgtctt tcacttggac    6720
acttcggggg tatcttcatc ttttatctgc aatttgaagt ttgagaagct tccagagtcg      6780
agtgttaaac ttttgcttct ttttttttaa tcttttgccc tttttttctta gtggcccttg     6840 actagtgatg cacatgtgac caattactaa atgagctttt attttgtctc tcttcttttt      6900
caagcaattt tttttaagta aatcatctaa aacaaagtac tatccatttt agttgtgtaa      6960
atggtgctat tttaaaaccg cacaaaaatt aaaaacataa aaataaaggt gtgcttcgca      7020
tacaagatgt atgcgccttc gtcttgcccc ttttgagact aagactacca taagaactta      7080
```

-continued

```
gtcacttgag aatggaatgg gtgcaagatg gacgacgata attctaaaga cctctagaag    7140
gatagtgtat agtaactaat acgaaccgaa atataagttt aactaaaatt ttaaagtcta    7200
tatttccata tggtatatgc tggaatacac gaaatgtcca gaatttgtag tggaccacga    7260
tccacacgtc ttttcaggat tctaggtgta ttccaacgaa aaatataaga aaaccatatt    7320
ctactatctg gttgttgtca tcctttcctt gccggcgtga cttctcatcc ttttattttt    7380
gtccggtgct ggtgacacac tttcctatga tagtgtggtg caaagtaagg tgatgatatg    7440
gtgttttgta gaggtgtggt gattttttgtg gtggtgggtg aagaggggt ggttgcatat    7500 agaaaggggt aagagtcaat gaggggtgga aggggacaag gggtatattg gtaaatgcat    7560
gtaacattag ggtggtgttg agtaattttt gggaagttaa tataaactac ccccttttgg    7620
tacaagagag aatacccgaa ctactgctct gatattttg ttcacgttat ttgatgtaat    7680
tacgcaatta atttgttttc tataagcttc cgcacacaat tgtgcatata aggctagtct    7740
aatatgagac accaacataa ctgactttct tttgcaacga aggtaccttg tcagatttag    7800
aacatagcat caggatttta tttgttgtat ctgtcatcct tgtttattgc tttaattatg    7860
ctttgtatga tgcattttac cacttcgtat gaaaaaagt gaaatttcat ttagtggtca    7920
tttacatatt acgagttgtg gacatgtttg aacatttgat tttggaaatt ttaagcctca    7980
tattatggag atttattgga cacaaatata gccataattc tccatcaact tgtttctaga    8040
agtgttgctc ttcctgatgt acttgaattc taattaggtt ttatcagaca ttatattata    8100
atgatatgat ttacaattttg ttgtagtgaa aaaggatttg gagctcgcgc gaaggattgg    8160
gggcagagag aggggatggt aactaaacaa cacagatgac tcatttattt aagggccaac    8220
aattgaattc gctgttgatt tcatctgtat atactgctct aggcttctat tccaatgtaa    8280
tttataaatc caaggttagt agcatgttaa gctttgtatt cagtataatg agacttatat    8340
tttgcagttg agattttagt tgtttgatgt gacttgtaaa ttgtaacttg taagtgacgt    8400
cttgaggatt atcgggacaa tatactattt ttttttcaa a                        8441
```

<210> SEQ ID NO 60
<211> LENGTH: 462
<212> TYPE: DNA
<213> ORGANISM: Artificial Sequence
<220> FEATURE:
<223> OTHER INFORMATION: Sorghum bicolor - cDNA coding for CENH3

<400> SEQUENCE: 60

```
atgagagtta aacacactgc tgccaggaaa tcaaccacca atggtcctcg ttcaaaggct     60
cagaaatctc cgcgcagttt gcaatcacca caatcgcctt ctagtagttc aaagcgcaaa    120
tcacgcagaa acactgatgc aactcctcaa aagaagaagg cttaccgccg taagccgggc    180
actgtggcac tctgggaaat acgcaaattt cagaagtcat tcaagcccett gattcctgct    240 gcgccttca ttcgaacagt gagagagatt actcaccagt ttgctcctta tgttggtcgt    300
tggcaagctg aagctctgat ggcccttcaa gaggctgcag agaattttat tgtccgtttg    360
tttgaagatg gtatgctttg tgcaattcat gccaaacgag ttacactcat gaaaaaggat    420
ttggagctcg cgcgaaggat tgggggcaga gagagggat gg                        462
```

<210> SEQ ID NO 61
<211> LENGTH: 154
<212> TYPE: PRT
<213> ORGANISM: Beta vulgaris

<400> SEQUENCE: 61

```
Met Arg Val Lys His Thr Ala Ala Arg Lys Ser Thr Thr Asn Gly Pro
1               5                   10                  15

Arg Ser Lys Ala Gln Lys Ser Pro Arg Ser Leu Gln Ser Pro Gln Ser
            20                  25                  30

Pro Ser Ser Ser Lys Arg Lys Ser Arg Arg Asn Thr Asp Ala Thr
                35                  40                  45

Pro Gln Lys Lys Lys Ala Tyr Arg Arg Lys Pro Gly Thr Val Ala Leu
    50                  55                  60

Trp Glu Ile Arg Lys Phe Gln Lys Ser Phe Lys Pro Leu Ile Pro Ala
65                  70                  75                  80

Ala Pro Phe Ile Arg Thr Val Arg Glu Ile Thr His Gln Phe Ala Pro
                85                  90                  95

Tyr Val Gly Arg Trp Gln Ala Glu Ala Leu Met Ala Leu Gln Glu Ala
            100                 105                 110

Ala Glu Asn Phe Ile Val Arg Leu Phe Glu Asp Gly Met Leu Cys Ala
            115                 120                 125

Ile His Ala Lys Arg Val Thr Leu Met Lys Lys Asp Leu Glu Leu Ala
    130                 135                 140

Arg Arg Ile Gly Gly Arg Glu Arg Gly Trp
145                 150
```

<210> SEQ ID NO 62
<211> LENGTH: 4001
<212> TYPE: DNA
<213> ORGANISM: Brassica napus

<400> SEQUENCE: 62

| | | | | | |
|---|---|---|---|---|---|
| tgtccgggag | gatccaccgg | cggtggtcgt | tactccattt | taacttgatg | tcttgaaagc | 60 |
| agaggacatg | gtatggtggc | ggcagaatct | attttagtt | gttaattttt | cttttcctct | 120 |
| gattctttt | atttttttcg | aatgaactaa | ctttgggttt | attcagaaga | attatcatct | 180 |
| aaaaactgat | tcaataaaca | aaataattta | catatttcac | aatgagccat | tagtaaacaa | 240 |
| gtcgaaagtg | aaaccaaatg | ggaagagaac | aatttttaata | aaaatatgtt | ctaatttcct | 300 |
| acttttatg | aattgaactc | ccgaagagaa | tggccgaaga | acggagtaaa | agctcaatga | 360 |
| ttgtaaaagc | tatgtattct | cttgctttga | ggaaaaagct | ttttgtttgc | actcataggc | 420 |
| ctgatatgtt | gtgatggctc | tttacatatt | gggtcttttg | tggtctatta | aacggttact | 480 |
| gaagaattag | tttatcgcat | ttaaaaaaaa | atatttgaaa | accacatatc | taaaatctca | 540 |
| atatattatt | tattgataga | tgaaagaaa | aatagtttat | aaaataatat | taattggtaa | 600 |
| atggaagtca | aaattttaca | tttaatacat | gactagttcg | attctccggc | tgaaacccat | 660 |
| ttaccactga | gccaagacca | cttgattata | tatatcaagc | tcttgttttt | tgcattaaca | 720 |
| aaagttgcat | ccaaaatttc | aaaacaacaa | ctaaattaat | gtctttctat | tttcaaagtt | 780 |
| ttatctccaa | acctattaat | agtttaattt | ttttttttaa | aattaggaaa | ccggttaaaa | 840 |
| tatattttaa | atacaaaaaa | cttaaacaat | gaatcattta | tttatttatt | cttcaaaatt | 900 |
| taaatatccg | aacccggccc | aaaatatccg | aacccgaaca | taaatatcc | gaacccgact | 960 |
| cgaagtgtag | aaaatatccg | aacgggtttt | ataccttat | actgaaatac | cctatacgaa | 1020 |
| cccgaatgtg | tatccgaacg | ccccctacaa | tatatgatca | tcatttgtat | cttgattgaa | 1080 |
| caaaaaaaaa | gttaaactat | tgatcacaaa | atttcaatg | tgagactttt | accattttta | 1140 |
| gtcatttata | gtcgtttta | aaaattcaaa | atataactta | taagaaaaaa | tctaatttt | 1200 |

```
tttattatat gcttaatgtg attgtttaat ttcttttaat aatataaaat taaacaaaaa    1260
atgagaggtt aaaaaaattg ttatcaaata tgtattattc ataatcatta attgtcatat    1320
atatgttaat tatattaggt aatttcgtag tttttattta agaaaagaaa aaaatattat    1380
tttgtacact actaattaat ttgatagtta gtttaataaa aaatatatta tattattata    1440
tggaccaact tattttttcta aaaaaaaacc actgttttaa aaaccaaacc aactataaac    1500
cggagatata ccggattgag tggctaaaac actctttgta tatatgtgct gagcaaaccc    1560
tctgagtgag atggcgtgtt aagaagtagg aggaccattc atgcctctta tgagttgtag    1620
tctgtgtgta caaaaaagaa gcgttggtgt gaaagaaagc agaaggattt gaaaatcaaa    1680
aaaattgaag gagaagcggg aaaacaaata atctctccct ccgctttttt ttctccaaat    1740
aatcaatctc tcatttcatt tgttaaccca agtttttgat aattatttca aagggggttta   1800 tttatctttt attcctccgg cggcagtaag tagtaatcaa tggcgagaac caaacatttc    1860
gcttccaggg cacgagatcg caatcgaact agttagtact ctctctctct ctgcctttt    1920 tttgatattt attttctagg ttaaaccta atttggcatc tgaaatttgt agatgcgact    1980
gcttcatctt cggcggcggc ggcggaaggt ccgagtgcgg tacgtcatct attttctttt    2040
cccgttttag gttttacgc aaatctcgtt actgttttt tgacgaatcg attgaaatgt    2100 gtagacccg acgagaagag aaggcagcca aggagaagct caacagagtg agtctttcta    2160
tttcattttc tgagatccat gaatccttt catctctcgt gtgttgtgac atgaatcaat    2220
tgcagcagca actcctacta cgactccacc agccggtaga aaagtaagtt acatttccat    2280
ttcacaccat tcatttgctt ctttatcaac aaactgctct ctcatctgtt tttttgttt    2340 tgttttggtt ttgtgaagaa aggagggact aagcgaacta acaagctat gcctaaaagt    2400 tagtgacaga ttttaaaatc tctatttgg atcatcattc tctcaggaca tgtctatttg    2460
catttgttct tattatgtct gtctgtctgt ctttgtcccc cttgtaggtt ccaacaagaa    2520
gaagacattc cgttacaagc ctggaaccgt tgccctcaga gagattcgcc atttccagaa    2580
gaccaccaaa cttcttatcc ctgccgctag tttcatccga gaagttagta atgaactttg    2640
ttattcatac attcccgctt acttgttttc aatgactctg caattactga tatagaattt    2700
ggagcaacca ttatggggtg atttctctaa ctacaaatta ctaatactat cccaggtgag    2760
aagtgtcacc cagatctttg cctctcccga tgttacccgt tggactgctg aagctcttat    2820
ggctattcaa gaggtacgtg tactccttcc ctcttttgtt tcctattttc cacttgatgt    2880
ctaatttaaa ctgatcgttt ttttttata tttcttttgg tgtggggcgg ggcaggcggc    2940
tgaagatttt ttaattggct tgttctctga tgctatgctt tgcgctatcc atgcaaggcg    3000
tgttactcta agtaagtagt actccccaaa ataaggaaac ccatttata tacaacattg    3060 cctcatccat gtctgcttct cttcatatca gtgagaaaag attttgagct tgcacgccgt    3120
cttggaggaa aaggcagacc attgtgatcg tttcgcaggt tgtataactt tgttcactcc    3180
ttatgtcttg tcatttgtga tctgactgac actttctttt gaaacataac tgcttgattc    3240
aatatctagg ctgtaaaact tatccctcct tgtttactat cttatatgct ttttccttgg    3300
aattgatagt ttccattgag atttcacttg cacgaaacat atctgctttc tcaatatctc    3360
tcagtcttag aaagggctat tgactaaaag aaaagaaaat ttagaggaag atttgtaaag    3420
acatgtgttt agagagggct taattaaaaa cacacgcttc tgctagcctt gctatttgat    3480
tcccaatttc aacttttttc gaggcatatt ataaagtttt taaatgtact tggcacttca    3540
```

```
acttttataa tttatataac gatttttattc taatagagca tttgtgattt catagtgttg     3600
tcatgaaact caagtaattc acaccgtccg atgttgctat tgtctaataa atgttgaaa      3660 aaattgtcaa aacagaacaa aaaacaacat agttgtctct atggtataaa actatcacta     3720
agttgtctct atagtataat attttttcgca atcccaaaac taattttttct ttaatcaaat   3780 taaacataaa ctaaaaccat tttttaaaaag tttaatggaa aaagataaaa aaataaggta    3840
atctcgtaat gtttttaaaaa ggaaaaaaaa tgtaaaaaca atttaaaaaa aagaacacac    3900
gacacagatc aaaaatatca tgtaatctaa ttgcatttgg tttctaaaat cttccaaaac    3960
tattctttta aaattctcta aggtaaaact tgattccaat a                         4001
```

<210> SEQ ID NO 63  
<211> LENGTH: 540  
<212> TYPE: DNA  
<213> ORGANISM: Brassica napus

<400> SEQUENCE: 63

```
atggcgagaa ccaaacattt cgcttccagg gcacgagatc gcaatcgaac taatgcgact    60
gcttcatctt cggcggcggc ggcggaaggt ccgagtgcga ccccgacgag aagagaaggc   120
agccaaggag aagctcaaca gacaactcct actacgactc caccagccgg tagaaaaaaa   180
ggagggacta agcgaactaa acaagctatg cctaaaagtt ccaacaagaa gaagacattc   240
cgttacaagc ctggaaccgt tgccctcaga gagattcgcc atttccagaa gaccaccaaa   300
cttcttatcc ctgccgctag tttcatccga gaagtgagaa gtgtcaccca gatctttgcc   360
tctcccgatg ttacccgttg gactgctgaa gctcttatgg ctattcaaga ggcggctgaa   420
gattttttaa ttggcttgtt ctctgatgct atgctttgcg ctatccatgc aaggcgtgtt   480
actctaatga gaaaagattt tgagcttgca cgccgtcttg gaggaaaagg cagaccattg   540
```

<210> SEQ ID NO 64  
<211> LENGTH: 180  
<212> TYPE: PRT  
<213> ORGANISM: Brassica napus

<400> SEQUENCE: 64

```
Met Ala Arg Thr Lys His Phe Ala Ser Arg Ala Arg Asp Arg Asn Arg
1               5                   10                  15

Thr Asn Ala Thr Ala Ser Ser Ser Ala Ala Ala Glu Gly Pro Ser
            20                  25                  30

Ala Thr Pro Thr Arg Arg Glu Gly Ser Gln Gly Glu Ala Gln Gln Thr
        35                  40                  45

Thr Pro Thr Thr Thr Pro Pro Ala Gly Arg Lys Lys Gly Gly Thr Lys
    50                  55                  60

Arg Thr Lys Gln Ala Met Pro Lys Ser Ser Asn Lys Lys Lys Thr Phe
65                  70                  75                  80

Arg Tyr Lys Pro Gly Thr Val Ala Leu Arg Glu Ile Arg His Phe Gln
                85                  90                  95

Lys Thr Thr Lys Leu Leu Ile Pro Ala Ala Ser Phe Ile Arg Glu Val
            100                 105                 110

Arg Ser Val Thr Gln Ile Phe Ala Ser Pro Asp Val Thr Arg Trp Thr
        115                 120                 125

Ala Glu Ala Leu Met Ala Ile Gln Glu Ala Ala Glu Asp Phe Leu Ile
    130                 135                 140

Gly Leu Phe Ser Asp Ala Met Leu Cys Ala Ile His Ala Arg Arg Val
145                 150                 155                 160
```

Thr Leu Met Arg Lys Asp Phe Glu Leu Ala Arg Arg Leu Gly Gly Lys
             165                 170                 175

Gly Arg Pro Leu
             180

<210> SEQ ID NO 65
<211> LENGTH: 4001
<212> TYPE: DNA
<213> ORGANISM: Brassica napus

<400> SEQUENCE: 65

| | | | | | |
|---|---|---|---|---|---|
| tgtccgggag | gatccaccgg | cggtggtcgt | tactccattt | taacttgatg | tcttgaaagc | 60 |
| agaggacatg | gtatggtggc | ggcagaatct | atttttagtt | gttaattttt | cttttcctct | 120 |
| gattcttttt | attttttcg | aatgaactaa | ctttgggttt | attcagaaga | attatcatct | 180 |
| aaaaactgat | tcaataaaca | aaataattta | catatttcac | aatgagccat | tagtaaacaa | 240 |
| gtcgaaagtg | aaaccaaatg | gaagagaac | aattttaata | aaaatatgtt | ctaatttcct | 300 |
| acttttatg | aattgaactc | ccgaagagaa | tggccgaaga | acggagtaaa | agctcaatga | 360 |
| ttgtaaaagc | tatgtattct | cttgctttga | ggaaaaagct | ttttgtttgc | actcataggc | 420 |
| ctgatatgtt | gtgatggctc | tttacatatt | gggtctttg | tggtctatta | aacggttact | 480 |
| gaagaattag | tttatcgcat | ttaaaaaaaa | atatttgaaa | accacatatc | taaaatctca | 540 |
| atatattatt | tattgataga | tgaaagaaa | aatagtttat | aaaataatat | taattggtaa | 600 |
| atggaagtca | aaattttaca | tttaatacat | gactagttcg | attctccggc | tgaaacccat | 660 |
| ttaccactga | gccaagacca | cttgattata | tatatcaagc | tcttgttttt | tgcattaaca | 720 |
| aaagttgcat | ccaaaatttc | aaaacaacaa | ctaaattaat | gtctttctat | tttcaaagtt | 780 |
| ttatctccaa | acctattaat | agtttaattt | tttttttaa | aattaggaaa | ccggttaaaa | 840 |
| tatatttaa | atacaaaaaa | cttaaacaat | gaatcattta | tttatttatt | cttcaaaatt | 900 |
| taaatatccg | aacccggccc | aaaatatccg | aacccgaaca | taaatatcc | gaacccgact | 960 |
| cgaagtgtag | aaaatatccg | aacgggtttt | ataccttat | actgaaatac | cctatacgaa | 1020 |
| cccgaatgtg | tatccgaacg | cccctacaa | tatatgatca | tcatttgtat | cttgattgaa | 1080 |
| caaaaaaaaa | gttaaactat | tgatcacaaa | attttcaatg | tgagactttt | accattttta | 1140 |
| gtcatttata | gtcgttttta | aaaattcaaa | atataactta | taagaaaaaa | tctaattttt | 1200 |
| tttattatat | gcttaatgtg | attgtttaat | ttcttttaat | aatataaaat | taaacaaaaa | 1260 |
| atgagaggtt | aaaaaaattg | ttatcaaata | tgtattattc | ataatcatta | attgtcatat | 1320 |
| atatgttaat | tatattaggt | aatttcgtag | ttttttattta | agaaaagaaa | aaaatattat | 1380 |
| tttgtacact | actaattaat | ttgatagtta | gtttaataaa | aaatatatta | tattattata | 1440 |
| tggaccaact | tatttttcta | aaaaaaaacc | actgttttaa | aaaccaaacc | aactataaac | 1500 |
| cggagatata | ccggattgag | tggctaaaac | actctttgta | tatatgtgct | gagcaaaccc | 1560 |
| tctgagtgag | atggcgtgtt | aagaagtagg | aggaccattc | atgcctctta | tgagttgtag | 1620 |
| tctgtgtgta | caaaaaagaa | gcgttggtgt | gaaagaaagc | agaaggattt | gaaaatcaaa | 1680 |
| aaaattgaag | gagaagcggg | aaaacaaata | atctctccct | ccgcttttt | ttctccaaat | 1740 |
| aatcaatctc | tcatttcatt | tgttaaccca | agttttgat | aattatttca | aggggttta | 1800 |
| tttatctttt | attcctccgg | cggcagtaag | tagtaatcaa | tggcgagaac | caaacatttc | 1860 |
| gcttccaggg | cacgagatcg | caatcgaact | agttagtact | ctctctctct | ctgccttttt | 1920 |

| | | | |
|---|---|---|---|
| tttgatatttt | attttctagg | ttaaaccta atttggcatc | tgaaatttgt agatgcgact | 1980 |
| gcttcatctt | cggcggcggc | ggcggaaggt | ccgagtgcgg tacgtcatct attttctttt | 2040 |
| cccgttttag | gttttacgc | aaatctcgtt | actgttttt tgacgaatcg attgaaatgt | 2100 |
| gtagaccccg | acgagaagag | aaggcagcca | aggagaagct caacagagtg agtcttctcta | 2160 |
| tttcattttc | tgagatccat | gaatcctttt | catctctcgt gtgttgtgac atgaatcaat | 2220 |
| tgcagcagca | actcctacta | cgactccacc | agccggtaga aagtaagtt acatttccat | 2280 |
| ttcacaccat | tcatttgctt | ctttatcaac | aaactgctct ctcatctgtt ttttttgttt | 2340 |
| tgttttggtt | ttgtgaagaa | aggagggact | aagcgaacta acaagctat gcctaaaagt | 2400 |
| tagtgacaga | ttttaaaatc | tctatttgg | atcatcattc tctcaggaca tgtctatttg | 2460 |
| catttgttct | tattatgtct | gtctgtctgt | ctttgtcccc cttgtaggtt ccaacaagaa | 2520 |
| gaagacattc | cgttacaagc | ctggaaccgt | tgccctcaga gagattcgcc atttccagaa | 2580 |
| gaccaccaaa | cttcttatcc | ctgccgctag | tttcatccga gaagttagta atgaactttg | 2640 |
| ttattcatac | attcccgctt | acttgttttc | aatgactctg caattactga tatagaattt | 2700 |
| ggagcaacca | ttatgggtg | atttctctaa | ctacaaatta ctaatactat cccaggtgag | 2760 |
| aagtgtcacc | cagatctttg | cccctcccga | tgttacccgt tgaactgctg aagctcttat | 2820 |
| ggctattcaa | gaggtacgtg | tactccttcc | ctcttttgtt tcctatttc cacttgatgt | 2880 |
| ctaatttaaa | ctgatcgttt | tttttttata | tttcttttgg tgtggggcgg ggcaggcggc | 2940 |
| tgaagatttt | ttaattggct | tgttctctga | tgctatgctt tgcgctatcc atgcaaggcg | 3000 |
| tgttactcta | agtaagtagt | actccccaaa | ataaggaaac ccatttatata tacaacattg | 3060 |
| cctcatccat | gtctgcttct | cttcatatca | gtgagaaaag attttgagct gcacgccgt | 3120 |
| cttggaggaa | aaggcagacc | attgtgatcg | tttcgcaggt tgtataactt tgttcactcc | 3180 |
| ttatgtcttg | tcatttgtga | tctgactgac | actttctttt gaaacataac tgcttgattc | 3240 |
| aatatctagg | ctgtaaaact | tatccctcct | tgtttactat cttatatgct tttcccttgg | 3300 |
| aattgatagt | ttccattgag | atttcacttg | cacgaaacat atctgctttc tcaatatctc | 3360 |
| tcagtcttag | aaagggctat | tgactaaaag | aaaagaaaat ttagaggaag atttgtaaag | 3420 |
| acatgtgttt | agagagggct | taattaaaaa | cacacgcttc tgctagcctt gctatttgat | 3480 |
| tcccaatttc | aacttttttc | gaggcatatt | ataaagtttt taaatgtact ggcacttca | 3540 |
| acttttataa | tttatataac | gatttttattc | taatagagca tttgtgattt catagtgttg | 3600 |
| tcatgaaact | caagtaattc | acaccgtccg | atgttgctat tgtctaataa aatgttgaaa | 3660 |
| aaattgtcaa | aacagaacaa | aaaacaacat | agttgtctct atggtataaa actatcacta | 3720 |
| agttgtctct | atagtataat | attttttcgca | atcccaaaac taattttct ttaatcaaat | 3780 |
| taaacataaa | ctaaaccat | ttttaaaaag | tttaatggaa aaagataaaa aaataaggta | 3840 |
| atctcgtaat | gttttaaaaa | ggaaaaaaaa | tgtaaaaaca atttaaaaaa aagaacacac | 3900 |
| gacacagatc | aaaatatca | tgtaatctaa | ttgcatttgg tttctaaaat cttccaaaac | 3960 |
| tattcttta | aaattctcta | aggtaaaact | tgattccaat a | 4001 |

<210> SEQ ID NO 66
<211> LENGTH: 540
<212> TYPE: DNA
<213> ORGANISM: Brassica napus

<400> SEQUENCE: 66

| | | |
|---|---|---|
| atggcgagaa ccaaacatttt cgcttccagg gcacgagatc gcaatcgaac taatgcgact | | 60 |

```
gcttcatctt cggcggcggc ggcggaaggt ccgagtgcga ccccgacgag aagagaaggc    120
agccaaggag aagctcaaca gacaactcct actacgactc caccagccgg tagaaaaaaa    180
ggagggacta agcgaactaa acaagctatg cctaaaagtt ccaacaagaa gaagacattc    240
cgttacaagc ctggaaccgt tgccctcaga gagattcgcc atttccagaa gaccaccaaa    300
cttcttatcc ctgccgctag tttcatccga gaagtgagaa gtgtcaccca gatctttgcc    360
cctcccgatg ttacccgttg aactgctgaa gctcttatgg ctattcaaga ggcggctgaa    420 gatttttaa ttggcttgtt ctctgatgct atgctttgcg ctatccatgc aaggcgtgtt     480
actctaatga gaaaagattt tgagcttgca cgccgtcttg gaggaaaagg cagaccattg    540
```

<210> SEQ ID NO 67
<211> LENGTH: 126
<212> TYPE: PRT
<213> ORGANISM: Brassica napus

<400> SEQUENCE: 67

```
Met Ala Arg Thr Lys His Phe Ala Ser Arg Ala Arg Asp Arg Asn Arg
1               5                   10                  15

Thr Asn Ala Thr Ala Ser Ser Ser Ala Ala Ala Glu Gly Pro Ser
            20                  25                  30

Ala Thr Pro Thr Arg Arg Glu Gly Ser Gln Gly Glu Ala Gln Gln Thr
        35                  40                  45

Thr Pro Thr Thr Thr Pro Pro Ala Gly Arg Lys Lys Gly Gly Thr Lys
    50                  55                  60

Arg Thr Lys Gln Ala Met Pro Lys Ser Ser Asn Lys Lys Lys Thr Phe
65                  70                  75                  80

Arg Tyr Lys Pro Gly Thr Val Ala Leu Arg Glu Ile Arg His Phe Gln
                85                  90                  95

Lys Thr Thr Lys Leu Leu Ile Pro Ala Ala Ser Phe Ile Arg Glu Val
            100                 105                 110

Arg Ser Val Thr Gln Ile Phe Ala Pro Pro Asp Val Thr Arg
        115                 120                 125
```

<210> SEQ ID NO 68
<211> LENGTH: 4001
<212> TYPE: DNA
<213> ORGANISM: Brassica napus

<400> SEQUENCE: 68

```
tgtccgggag gatccaccgg cggtggtcgt tactccattt taacttgatg tcttgaaagc     60
agaggacatg gtatggtggc ggcagaatct attttagtt gttaattttt cttttcctct     120 gattctttt attttttcg aatgaactaa ctttgggttt attcagaaga attatcatct      180
aaaaactgat tcaataaaca aaataattta catatttcac aatgagccat tagtaaacaa    240
gtcgaaagtg aaaccaaatg ggaagagaac aattttaata aaaatatgtt ctaatttcct    300 acttttatg aattgaactc ccgaagagaa tggccgaaga acggagtaaa agctcaatga     360
ttgtaaaagc tatgtattct cttgctttga ggaaaaagct ttttgtttgc actcataggc    420
ctgatatgtt gtgatggctc tttacatatt gggtcttttg tggtctatta aacggttact    480
gaagaattag tttatcgcat ttaaaaaaaa atatttgaaa accacatatc taaaatctca    540
atatattatt tattgataga tgaaagaaa aatagtttat aaaataatat taattggtaa     600
atggaagtca aaatttttaca tttaatacat gactagttcg attctccggc tgaaacccat   660
```

```
ttaccactga gccaagacca cttgattata tatatcaagc tcttgttttt tgcattaaca    720
aaagttgcat ccaaaatttc aaaacaacaa ctaaattaat gtctttctat tttcaaagtt    780
ttatctccaa acctattaat agtttaattt ttttttttaa aattaggaaa ccggttaaaa    840
tatattttaa atacaaaaaa cttaaacaat gaatcattta tttatttatt cttcaaaatt    900
taaatatccg aacccggccc aaaatatccg aacccgaaca taaatatccc gaacccgact    960
cgaagtgtag aaaatatccg aacgggtttt atacctttat actgaaatac cctatacgaa   1020
cccgaatgtg tatccgaacg cccctacaa tatatgatca tcatttgtat cttgattgaa    1080
caaaaaaaaa gttaaactat tgatcacaaa attttcaatg tgagactttt accattttta   1140
gtcatttata gtcgttttta aaaattcaaa ataaactta taagaaaaaa tctaattttt    1200
tttattatat gcttaatgtg attgtttaat ttcttttaat aatataaaat taaacaaaaa   1260
atgagaggtt aaaaaaattg ttatcaaata tgtattattc ataatcatta attgtcatat   1320
atatgttaat tatattaggt aatttcgtag ttttttattta agaaaagaaa aaatatattat 1380
tttgtacact actaattaat ttgatagtta gtttaataaa aatatatta tattattata    1440
tggaccaact tatttttcta aaaaaaaacc actgttttaa aaaccaaacc aactataaac   1500
cggagatata ccggattgag tggctaaaac actcttgta tatatgtgct gagcaaaccc    1560
tctgagtgag atggcgtgtt aagaagtagg aggaccattc atgcctctta tgagttgtag   1620
tctgtgtgta caaaaaagaa gcgttggtgt gaaagaaagc agaaggattt gaaatcaaa    1680
aaaattgaag gagaagcggg aaaacaaata atctctccct ccgcttttt ttctccaaat    1740
aatcaatctc tcatttcatt tgttaaccca agttttgat aattatttca aagggggttta   1800
tttatctttt attcctccgg cggcagtaag tagtaatcaa tggcgagaac caaacatttc   1860
gcttccaggg cacgagatcg caatcgaact agttagtact ctctctctct ctgccttttt   1920
tttgatattt attttctagg ttaaacccta atttggcatc tgaaatttgt agatgcgact   1980
gcttcatctt cggcggcggc ggcggaaggt ccgagtgcgg tacgtcatct attttcttt    2040
cccgttttag gttttttacgc aaatctcgtt actgtttttt tgacgaatcg attgaaatgt   2100
gtagaccccg acgagaagag aaggcagcca aggagaagct caacagagtg agtcttctca   2160
tttcattttc tgagatccat gaatcctttt catctctcgt gtgttgtgac atgaatcaat   2220
tgcagcagca actcctacta cgactccacc agccggtaga aaagtaagtt acatttccat   2280
ttcacaccat tcatttgctt ctttatcaac aaactgctct ctcatctgtt ttttttgttt   2340
tgttttggtt ttgtgaagaa aggagggact aagcgaacta acaagctat gcctaaaagt    2400
tagtgacaga ttttaaaatc tctatttggg atcatcattc tctcaggaca tgtctatttg   2460
catttgttct tattatgtct gtctgtctgt ctttgtcccc cttgtaggtt ccaacaagaa   2520
gaagacattc cgttacaagc ctggaaccgt tgccctcaga gagattcgcc atttccagaa   2580
gaccaccaaa cttcttatcc ctgccgctag tttcatccga gaagttagta atgaactttg   2640
ttattcatac attcccgctt acttgttttc aatgactctg caattactga tatagaattt   2700
ggagcaacca ttatggggtg atttctctaa ctacaaatta ctaatactat cccaggtgag   2760
aagtgtcacc cagatctttg cccctcccga tgttacccgt tggactgctg aagcttttat   2820
ggctattcaa gaggtacgtg tactccttcc ctcttttgtt tcctatttc cacttgatgt    2880
ctaatttaaa ctgatcgttt ttttttata tttcttttgg tgtggggcgg ggcaggcggc   2940
tgaagatttt ttaattggct tgttctctga tgctatgctt tgcgctatcc atgcaaggcg   3000
tgttactcta agtaagtagt actccccaaa ataaggaaac ccatttttata tacaacattg  3060
```

```
cctcatccat gtctgcttct cttcatatca gtgagaaaag attttgagct tgcacgccgt    3120
cttggaggaa aaggcagacc attgtgatcg tttcgcaggt tgtataactt tgttcactcc    3180
ttatgtcttg tcatttgtga tctgactgac actttctttt gaaacataac tgcttgattc    3240
aatatctagg ctgtaaaact tatccctcct tgtttactat cttatatgct ttttccttgg    3300
aattgatagt ttccattgag atttcacttg cacgaaacat atctgctttc tcaatatctc    3360
tcagtcttag aaagggctat tgactaaaag aaaagaaaat ttagaggaag atttgtaaag    3420
acatgtgttt agagagggct taattaaaaa cacacgcttc tgctagcctt gctatttgat    3480
tcccaatttc aactttttc gaggcatatt ataaagtttt taaatgtact tggcacttca    3540
acttttataa tttatataac gattttattc taatagagca tttgtgattt catagtgttg    3600
tcatgaaact caagtaattc acaccgtccg atgttgctat tgtctaataa aatgttgaaa    3660
aaattgtcaa aacagaacaa aaaacaacat agttgtctct atggtataaa actatcacta    3720
agttgtctct atagtataat attttcgca atcccaaaac taattttct ttaatcaaat    3780 taaacataaa ctaaaaccat tttaaaaag tttaatggaa aaagataaaa aataaggta    3840 atctcgtaat gttttaaaaa ggaaaaaaaa tgtaaaaaca atttaaaaaa aagaacacac    3900
gacacagatc aaaaatatca tgtaatctaa ttgcatttgg tttctaaaat cttccaaaac    3960 tattcttta aaattctcta aggtaaaact tgattccaat a                        4001

<210> SEQ ID NO 69
<211> LENGTH: 540
<212> TYPE: DNA
<213> ORGANISM: Brassica napus

<400> SEQUENCE: 69
atggcgagaa ccaaacattt cgcttccagg gcacgagatc gcaatcgaac taatgcgact      60
gcttcatctt cggcggcggc ggcggaaggt ccgagtgcga ccccgacgag aagagaaggc     120
agccaaggag aagctcaaca gacaactcct actacgactc caccagccgg tagaaaaaaa     180
ggagggacta gcgaactaa acaagctatg cctaaaagtt ccaacaagaa gaagacattc     240
cgttacaagc ctggaaccgt tgccctcaga gagattcgcc atttccagaa gaccaccaaa     300
cttcttatcc ctgccgctag tttcatccga gaagtgagaa gtgtcaccca gatctttgcc     360
cctcccgatg ttacccgttg gactgctgaa gcttttatgg ctattcaaga ggcggctgaa     420 gatttttaa ttggcttgtt ctctgatgct atgctttgcg ctatccatgc aaggcgtgtt     480
actctaatga gaaaagattt tgagcttgca cgccgtcttg gaggaaaagg cagaccattg     540

<210> SEQ ID NO 70
<211> LENGTH: 180
<212> TYPE: PRT
<213> ORGANISM: Brassica napus

<400> SEQUENCE: 70

Met Ala Arg Thr Lys His Phe Ala Ser Arg Ala Arg Asp Arg Asn Arg
1               5                   10                  15

Thr Asn Ala Thr Ala Ser Ser Ser Ala Ala Ala Glu Gly Pro Ser
            20                  25                  30

Ala Thr Pro Thr Arg Arg Glu Gly Ser Gln Gly Glu Ala Gln Gln Thr
        35                  40                  45

Thr Pro Thr Thr Thr Pro Pro Ala Gly Arg Lys Lys Gly Gly Thr Lys
    50                  55                  60
```

```
Arg Thr Lys Gln Ala Met Pro Lys Ser Ser Asn Lys Lys Thr Phe
 65                  70                  75                  80

Arg Tyr Lys Pro Gly Thr Val Ala Leu Arg Glu Ile Arg His Phe Gln
                 85                  90                  95

Lys Thr Thr Lys Leu Leu Ile Pro Ala Ala Ser Phe Ile Arg Glu Val
                100                 105                 110

Arg Ser Val Thr Gln Ile Phe Ala Pro Pro Asp Val Thr Arg Trp Thr
            115                 120                 125

Ala Glu Ala Phe Met Ala Ile Gln Glu Ala Ala Glu Asp Phe Leu Ile
        130                 135                 140

Gly Leu Phe Ser Asp Ala Met Leu Cys Ala Ile His Ala Arg Arg Val
145                 150                 155                 160

Thr Leu Met Arg Lys Asp Phe Glu Leu Ala Arg Arg Leu Gly Gly Lys
                165                 170                 175

Gly Arg Pro Leu
            180

<210> SEQ ID NO 71
<211> LENGTH: 4001
<212> TYPE: DNA
<213> ORGANISM: Brassica napus

<400> SEQUENCE: 71
tgtccgggag gatccaccgg cggtggtcgt tactccattt taacttgatg tcttgaaagc      60
agaggacatg gtatggtggc ggcagaatct attttagtt gttaattttt cttttcctct     120
gattcttttt attttttcg aatgaactaa ctttgggttt attcagaaga attatcatct     180
aaaaactgat tcaataaaca aaataattta catatttcac aatgagccat tagtaaacaa     240
gtcgaaagtg aaaccaaatg ggaagagaac aattttaata aaaatatgtt ctaatttcct     300 acttttatg aattgaactc ccgaagagaa tggccgaaga acggagtaaa agctcaatga     360
ttgtaaaagc tatgtattct cttgctttga ggaaaaagct ttttgtttgc actcataggc     420
ctgatatgtt gtgatggctc tttacatatt gggtcttttg tggtctatta aacggttact     480
gaagaattag tttatcgcat ttaaaaaaaa atatttgaaa accacatatc taaaatctca     540
atatattatt tattgataga tgaaaagaaa aatagtttat aaaataatat taattggtaa     600
atggaagtca aaattttaca tttaatacat gactagttcg attctccggc tgaaacccat     660
ttaccactga gccaagacca cttgattata tatatcaagc tcttgttttt tgcattaaca     720
aaagttgcat ccaaaatttc aaaacaacaa ctaaattaat gtctttctat tttcaaagtt     780
ttatctccaa acctattaat agtttaattt ttttttttaa aattaggaaa ccggttaaaa     840
tatattttaa atacaaaaaa cttaaacaat gaatcattta tttatttatt cttcaaaatt     900
taaatatccg aacccggccc aaaatatccg aacccgaaca taaatatcc gaacccgact     960 cgaagtgtag aaaatatccg aacgggtttt ataccttat actgaaatac cctatacgaa    1020
cccgaatgtg tatccgaacg cccctacaa tatatgatca tcatttgtat cttgattgaa    1080
caaaaaaaaa gttaaactat tgatcacaaa attttcaatg tgagactttt accatttta    1140 gtcatttata gtcgttttta aaattcaaa atataactta taagaaaaaa tctaattttt    1200
tttattatat gcttaatgtg attgtttaat ttctttaat aatataaaat taaacaaaaa    1260
atgagaggtt aaaaaaattg ttatcaaata tgtattattc ataatcatta attgtcatat    1320
atatgttaat tatattaggt aatttcgtag ttttttattta agaaaagaaa aaatatatt    1380 tttgtacact actaattaat ttgatagtta gtttaataaa aaatatatta tattattata    1440
```

```
tggaccaact tatttttcta aaaaaaaacc actgttttaa aaaccaaacc aactataaac    1500
cggagatata ccggattgag tggctaaaac actctttgta tatatgtgct gagcaaaccc    1560
tctgagtgag atggcgtgtt aagaagtagg aggaccattc atgcctctta tgagttgtag    1620
tctgtgtgta caaaaaagaa gcgttggtgt gaaagaaagc agaaggattt gaaaatcaaa    1680
aaaattgaag gagaagcggg aaaacaaata atctctccct ccgctttttt ttctccaaat    1740
aatcaatctc tcatttcatt tgttaaccca agttttttgat aattatttca aaggggttta    1800
tttatctttt attcctccgg cggcagtaag tagtaatcaa tggcgagaac caaacatttc    1860
gcttccaggg cacgagatcg caatcgaact agttagtact ctctctctct ctgccttttt    1920
tttgatattt attttctagg ttaaacccta atttggcatc tgaaatttgt agatgcgact    1980
gcttcatctt cggcggcggc ggcggaaggt ccgagtgcgg tacgtcatct attttctttt    2040
cccgttttag gttttacgc aaatctcgtt actgtttttt tgacgaatcg attgaaatgt     2100
gtagaccccg acgagaagag aaggcagcca aggagaagct caacagagtg agtctttcta    2160
tttcattttc tgagatccat gaatcctttt catctctcgt gtgttgtgac atgaatcaat    2220
tgcagcagca actcctacta cgactccacc agccggtaga aaagtaagtt acatttccat    2280
ttcacaccat tcatttgctt ctttatcaac aaactgctct ctcatctgtt ttttttgttt    2340
tgttttggtt ttgtgaagaa aggagggact aagcgaacta acaagctat gcctaaaagt     2400 tagtgacaga ttttaaaatc tctattttgg atcatcattc tctcaggaca tgtctatttg    2460
catttgttct tattatgtct gtctgtctgt ctttgtcccc cttgtaggtt ccaacaagaa    2520
gaagacattc cgttacaagc ctggaaccgt tgccctcaga gagattcgcc atttccagaa    2580
gaccaccaaa cttcttatcc ctgccgctag tttcatccga gaagttagta atgaactttg    2640
ttattcatac attcccgctt acttgttttc aatgactctg caattactga tatagaattt    2700
ggagcaacca ttatggggtg atttctctaa ctacaaatta ctaatactat cccaggtgag    2760
aagtgtcacc cagatctttg cccctcccga tgttacccgt tggactgctg aagctcttat    2820
ggctattcaa gaggtacgtg tactccttcc ctctttttgtt tcctatttttc cacttgatgt    2880 ctaatttaaa ctgatcgttt ttttttttata tttcttttgg tgtggggcgg ggcagacggc    2940
tgaagatttt ttaattggct tgttctctga tgctatgctt tgcgctatcc atgcaaggcg    3000
tgttactcta agtaagtagt actccccaaa ataaggaaac ccatttttata tacaacattg    3060 cctcatccat gtctgcttct cttcatatca gtgagaaaag attttgagct tgcacgccgt    3120
cttggaggaa aaggcagacc attgtgatcg tttcgcaggt tgtataactt tgttcactcc    3180
ttatgtcttg tcatttgtga tctgactgac actttctttt gaaacataac tgcttgattc    3240
aatatctagg ctgtaaaact tatccctcct tgtttactat cttatatgct ttttccttgg    3300
aattgatagt ttccattgag atttcacttg cacgaaacat atctgctttc tcaatatctc    3360
tcagtcttag aaagggctat tgactaaaag aaaagaaaat ttagaggaag atttgtaaag    3420
acatgtgttt agagagggct taattaaaaa cacacgcttc tgctagcctt gctatttgat    3480
tcccaatttc aacttttttc gaggcatatt ataaagtttt taaatgtact tggcacttca    3540
acttttataa tttatataac gatttttattc taatagagca tttgtgatttt catagtgttg    3600 tcatgaaact caagtaattc acaccgtccg atgttgctat tgtctaataa aatgttgaaa    3660
aaattgtcaa aacagaacaa aaaacaacat agttgtctct atggtataaa actatcacta    3720
agttgtctct atagtataat attttttcgca atcccaaaac taatttttct ttaatcaaat    3780
```

```
taaacataaa ctaaaaccat ttttaaaaag tttaatggaa aaagataaaa aaataaggta      3840
atctcgtaat gttttaaaaa ggaaaaaaaa tgtaaaaaca atttaaaaaa aagaacacac      3900
gacacagatc aaaaatatca tgtaatctaa ttgcatttgg tttctaaaat cttccaaaac      3960
tattctttta aaattctcta aggtaaaact tgattccaat a                          4001
```

<210> SEQ ID NO 72
<211> LENGTH: 540
<212> TYPE: DNA
<213> ORGANISM: Brassica napus

<400> SEQUENCE: 72

```
atggcgagaa ccaaacattt cgcttccagg gcacgagatc gcaatcgaac taatgcgact       60
gcttcatctt cggcggcggc ggcggaaggt ccgagtgcga ccccgacgag aagagaaggc      120
agccaaggag aagctcaaca dacaactcct actacgactc caccagccgg tagaaaaaaa      180
ggagggacta agcgaactaa acaagctatg cctaaaagtt ccaacaagaa gaagacattc      240
cgttacaagc ctggaaccgt tgccctcaga gagattcgcc atttccagaa gaccaccaaa      300
cttcttatcc ctgccgctag tttcatccga gaagtgagaa gtgtcaccca gatctttgcc      360
cctcccgatg ttacccgttg gactgctgaa gctcttatgg ctattcaaga gacggctgaa      420
gattttttaa ttggcttgtt ctctgatgct atgctttgcg ctatccatgc aaggcgtgtt      480
actctaatga gaaagatttt tgagcttgca cgccgtcttg gaggaaaagg cagaccattg      540
```

<210> SEQ ID NO 73
<211> LENGTH: 180
<212> TYPE: PRT
<213> ORGANISM: Brassica napus

<400> SEQUENCE: 73

```
Met Ala Arg Thr Lys His Phe Ala Ser Arg Ala Arg Asp Arg Asn Arg
1               5                   10                  15

Thr Asn Ala Thr Ala Ser Ser Ser Ala Ala Ala Glu Gly Pro Ser
            20                  25                  30

Ala Thr Pro Thr Arg Arg Glu Gly Ser Gln Gly Glu Ala Gln Gln Thr
        35                  40                  45

Thr Pro Thr Thr Thr Pro Pro Ala Gly Arg Lys Lys Gly Gly Thr Lys
    50                  55                  60

Arg Thr Lys Gln Ala Met Pro Lys Ser Ser Asn Lys Lys Lys Thr Phe
65                  70                  75                  80

Arg Tyr Lys Pro Gly Thr Val Ala Leu Arg Glu Ile Arg His Phe Gln
                85                  90                  95

Lys Thr Thr Lys Leu Leu Ile Pro Ala Ala Ser Phe Ile Arg Glu Val
            100                 105                 110

Arg Ser Val Thr Gln Ile Phe Ala Pro Pro Asp Val Thr Arg Trp Thr
        115                 120                 125

Ala Glu Ala Leu Met Ala Ile Gln Glu Thr Ala Glu Asp Phe Leu Ile
    130                 135                 140

Gly Leu Phe Ser Asp Ala Met Leu Cys Ala Ile His Ala Arg Arg Val
145                 150                 155                 160

Thr Leu Met Arg Lys Asp Phe Glu Leu Ala Arg Arg Leu Gly Gly Lys
                165                 170                 175

Gly Arg Pro Leu
            180
```

<210> SEQ ID NO 74
<211> LENGTH: 4001
<212> TYPE: DNA
<213> ORGANISM: Brassica napus

<400> SEQUENCE: 74

| | | | | | |
|---|---|---|---|---|---|
| tgtccgggag | gatccaccgg | cggtggtcgt | tactccattt | taacttgatg | tcttgaaagc | 60 |
| agaggacatg | gtatggtggc | ggcagaatct | attttagtt | gttaatttt | cttttcctct | 120 |
| gattctttt | atttttcg | aatgaactaa | ctttgggttt | attcagaaga | attatcatct | 180 |
| aaaaactgat | tcaataaaca | aaataattta | catatttcac | aatgagccat | tagtaaacaa | 240 |
| gtcgaaagtg | aaaccaaatg | ggaagagaac | aatttaata | aaaatatgtt | ctaatttcct | 300 |
| actttatg | aattgaactc | ccgaagagaa | tggccgaaga | acggagtaaa | agctcaatga | 360 |
| ttgtaaaagc | tatgtattct | cttgctttga | ggaaaaagct | ttttgtttgc | actcataggc | 420 |
| ctgatatgtt | gtgatggctc | tttacatatt | gggtctttg | tggtctatta | aacggttact | 480 |
| gaagaattag | ttatcgcat | ttaaaaaaaa | atatttgaaa | accacatatc | taaaatctca | 540 |
| atatattatt | tattgataga | tgaaagaaa | aatagtttat | aaaataatat | taattggtaa | 600 |
| atggaagtca | aaattttaca | tttaatacat | gactagttcg | attctccggc | tgaaacccat | 660 |
| ttaccactga | gccaagacca | cttgattata | tatatcaagc | tcttgttttt | tgcattaaca | 720 |
| aaagttgcat | ccaaaatttc | aaaacaacaa | ctaaattaat | gtctttctat | tttcaaagtt | 780 |
| ttatctccaa | acctattaat | agtttaattt | tttttttaa | aattaggaaa | ccggttaaaa | 840 |
| tatattttaa | atacaaaaaa | cttaaacaat | gaatcattta | tttatttatt | cttcaaaatt | 900 |
| taaatatccg | aacccggccc | aaaatatccg | aacccgaaca | taaatatcc | gaacccgact | 960 |
| cgaagtgtag | aaaatatccg | aacgggtttt | ataccttat | actgaaatac | cctatacgaa | 1020 |
| cccgaatgtg | tatccgaacg | cccctacaa | tatatgatca | tcatttgtat | cttgattgaa | 1080 |
| caaaaaaaa | gttaaactat | tgatcacaaa | attttcaatg | tgagactttt | accattttta | 1140 |
| gtcatttata | gtcgttttta | aaaattcaaa | ataaactta | taagaaaaaa | tctaattttt | 1200 |
| tttattatat | gcttaatgtg | attgtttaat | ttcttttaat | aatataaaat | taaacaaaaa | 1260 |
| atgagaggtt | aaaaaaattg | ttatcaaata | tgtattattc | ataatcatta | attgtcatat | 1320 |
| atatgttaat | tatattaggt | aatttcgtag | tttttattta | agaaaagaaa | aaaatattat | 1380 |
| tttgtacact | actaattaat | ttgatagtta | gtttaataaa | aatatatta | tattattata | 1440 |
| tggaccaact | tattttctca | aaaaaaaacc | actgttttaa | aaaccaaacc | aactataaac | 1500 |
| cggagatata | ccggattgag | tggctaaaac | actcttgta | tatatgtgct | gagcaaaccc | 1560 |
| tctgagtgag | atggcgtgtt | aagaagtagg | aggaccattc | atgcctctta | tgagttgtag | 1620 |
| tctgtgtgta | caaaaagaa | gcgttggtgt | gaaagaaagc | agaaggattt | gaaaatcaaa | 1680 |
| aaaattgaag | gagaagcggg | aaaacaaata | atctctccct | ccgctttttt | ttctccaaat | 1740 |
| aatcaatctc | tcatttcatt | tgttaaccca | agttttgat | aattatttca | aaggggttta | 1800 |
| tttatctttt | attcctccgg | cggcagtaag | tagtaatcaa | tggcgagaac | caaacatttc | 1860 |
| gcttccaggg | cacgagatcg | caatcgaact | agttagtact | ctctctctct | ctgccttttt | 1920 |
| tttgatattt | attttctagg | ttaaacccta | atttggcatc | tgaaatttgt | agatgcgact | 1980 |
| gcttcatctt | cggcggcggc | ggcggaaggt | ccgagtgcgg | tacgtcatct | attttctttt | 2040 |
| cccgttttag | gttttacgc | aaatctcgtt | actgttttt | tgacgaatcg | attgaaatgt | 2100 |
| gtagaccccg | acgagaagag | aaggcagcca | aggagaagct | caacagagtg | agtctttcta | 2160 |

| | |
|---|---|
| tttcattttc tgagatccat gaatcctttt catctctcgt gtgttgtgac atgaatcaat | 2220 |
| tgcagcagca actcctacta cgactccacc agccggtaga aaagtaagtt acatttccat | 2280 |
| ttcacaccat tcatttgctt ctttatcaac aaactgctct ctcatctgtt ttttttgttt | 2340 |
| tgttttggtt ttgtgaagaa aggagggact aagcgaacta acaagctat gcctaaaagt | 2400 |
| tagtgacaga ttttaaaatc tctattttgg atcatcattc tctcaggaca tgtctatttg | 2460 |
| catttgttct tattatgtct gtctgtctgt ctttgtcccc cttgtaggtt ccaacaagaa | 2520 |
| gaagacattc cgttacaagc ctggaaccgt tgccctcaga gagattcgcc atttccagaa | 2580 |
| gaccaccaaa cttcttatcc ctgccgctag tttcatccga aagttagta atgaactttg | 2640 |
| ttattcatac attcccgctt acttgttttc aatgactctg caattactga tatagaatttt | 2700 |
| ggagcaacca ttatggggtg atttctctaa ctacaaatta ctaatactat cccaggtgag | 2760 |
| aagtgtcacc cagatctttg cccctcccga tgttacccgt tggactgctg aagctcttat | 2820 |
| ggctattcaa gaggtacgtg tactccttcc ctcttttgtt tcctattttc cacttgatgt | 2880 |
| ctaatttaaa ctgatcgttt ttttttata tttcttttgg tgtggggcgg ggcaggcggc | 2940 |
| tgaagatttt ttaattggct tgttctctga tactatgctt tgcgctatcc atgcaaggcg | 3000 |
| tgttactcta agtaagtagt actccccaaa ataaggaaac ccattttata tacaacattg | 3060 |
| cctcatccat gtctgcttct cttcatatca gtgagaaaag attttgagct tgcacgccgt | 3120 |
| cttggaggaa aaggcagacc attgtgatcg tttcgcaggt tgtataactt tgttcactcc | 3180 |
| ttatgtcttg tcatttgtga tctgactgac actttcttt gaaacataac tgcttgattc | 3240 |
| aatatctagg ctgtaaaact tatccctcct tgtttactat cttatatgct ttttccttgg | 3300 |
| aattgatagt ttccattgag atttcacttg cacgaaacat atctgctttc tcaatatctc | 3360 |
| tcagtcttag aaagggctat tgactaaaag aaaagaaaat ttagaggaag atttgtaaag | 3420 |
| acatgtgttt agagagggct taattaaaaa cacacgcttc tgctagcctt gctatttgat | 3480 |
| tcccaatttc aacttttttc gaggcatatt ataaagtttt taaatgtact tggcacttca | 3540 |
| actttttataa tttatataac gattttattc taatagagca tttgtgattt catagtgttg | 3600 |
| tcatgaaact caagtaattc acaccgtccg atgttgctat tgtctaataa aatgttgaaa | 3660 |
| aaattgtcaa aacagaacaa aaaacaacat agttgtctct atggtataaa actatcacta | 3720 |
| agttgtctct atagtataat attttttcgca atcccaaaac taattttttct ttaatcaaat | 3780 |
| taaacataaa ctaaaaccat ttttaaaaag tttaatggaa aaagataaaa aaataaggta | 3840 |
| atctcgtaat gttttaaaaa ggaaaaaaaa tgtaaaaaca atttaaaaaa aagaacacac | 3900 |
| gacacagatc aaaaatatca tgtaatctaa ttgcatttgg tttctaaaat cttccaaaac | 3960 |
| tattctttta aaattctcta aggtaaaact tgattccaat a | 4001 |

<210> SEQ ID NO 75
<211> LENGTH: 540
<212> TYPE: DNA
<213> ORGANISM: Brassica napus

<400> SEQUENCE: 75

| | |
|---|---|
| atggcgagaa ccaaacattt cgcttccagg gcacgagatc gcaatcgaac taatgcgact | 60 |
| gcttcatctt cggcggcggc ggcggaaggt ccgagtgcga ccccgacgag aagagaaggc | 120 |
| agccaaggag aagctcaaca gacaactcct actacgactc caccagccgg tagaaaaaaa | 180 |
| ggagggacta agcgaactaa acaagctatg cctaaaagtt ccaacaagaa gaagacattc | 240 |
| cgttacaagc ctggaaccgt tgccctcaga gagattcgcc atttccagaa gaccaccaaa | 300 |

```
cttcttatcc ctgccgctag tttcatccga gaagtgagaa gtgtcaccca gatctttgcc      360
cctcccgatg ttacccgttg gactgctgaa gctcttatgg ctattcaaga ggcggctgaa      420
gattttttaa ttggcttgtt ctctgatact atgctttgcg ctatccatgc aaggcgtgtt      480
actctaatga gaaagatttt gagcttgca cgccgtcttg aggaaaagg cagaccattg        540
```

<210> SEQ ID NO 76
<211> LENGTH: 180
<212> TYPE: PRT
<213> ORGANISM: Brassica napus

<400> SEQUENCE: 76

```
Met Ala Arg Thr Lys His Phe Ala Ser Arg Ala Arg Asp Arg Asn Arg
1               5                   10                  15

Thr Asn Ala Thr Ala Ser Ser Ala Ala Ala Glu Gly Pro Ser
            20                  25                  30

Ala Thr Pro Thr Arg Arg Glu Gly Ser Gln Gly Glu Ala Gln Gln Thr
        35                  40                  45

Thr Pro Thr Thr Thr Pro Pro Ala Gly Arg Lys Lys Gly Gly Thr Lys
    50                  55                  60

Arg Thr Lys Gln Ala Met Pro Lys Ser Ser Asn Lys Lys Lys Thr Phe
65                  70                  75                  80

Arg Tyr Lys Pro Gly Thr Val Ala Leu Arg Glu Ile Arg His Phe Gln
                85                  90                  95

Lys Thr Thr Lys Leu Leu Ile Pro Ala Ala Ser Phe Ile Arg Glu Val
            100                 105                 110

Arg Ser Val Thr Gln Ile Phe Ala Pro Pro Asp Val Thr Arg Trp Thr
        115                 120                 125

Ala Glu Ala Leu Met Ala Ile Gln Glu Ala Ala Glu Asp Phe Leu Ile
    130                 135                 140

Gly Leu Phe Ser Asp Ala Met Leu Tyr Ala Ile His Ala Arg Arg Val
145                 150                 155                 160

Thr Leu Met Arg Lys Asp Phe Glu Leu Ala Arg Arg Leu Gly Gly Lys
                165                 170                 175

Gly Arg Pro Leu
            180
```

<210> SEQ ID NO 77
<211> LENGTH: 4001
<212> TYPE: DNA
<213> ORGANISM: Brassica napus

<400> SEQUENCE: 77

```
tgtccgggag gatccaccgg cggtggtcgt tactccattt taacttgatg tcttgaaagc      60
agaggacatg gtatggtggc ggcagaatct attttagtt gttaattttt ctttcctct       120 gattctttt atttttttcg aatgaactaa ctttgggttt attcagaaga attatcatct       180
aaaaactgat tcaataaaca aaataattta catatttcac aatgagccat tagtaaacaa      240
gtcgaaagtg aaaccaaatg ggaagagaac aattttaata aaaatatgtt ctaatttcct      300 acttttatg aattgaactc ccgaagagaa tggccgaaga acggagtaaa agctcaatga       360
ttgtaaaagc tatgtattct cttgctttga ggaaaaagct ttttgtttgc actcataggc      420
ctgatatgtt gtgatggctc tttacatatt gggtcttttg tggtctatta aacggttact      480
gaagaattag tttatcgcat ttaaaaaaaa atatttgaaa accacatatc taaaatctca      540
```

```
atatattatt tattgataga tgaaaagaaa aatagtttat aaaataatat taattggtaa      600
atggaagtca aaattttaca tttaatacat gactagttcg attctccggc tgaaacccat      660
ttaccactga gccaagacca cttgattata tatatcaagc tcttgttttt tgcattaaca      720
aaagttgcat ccaaaatttc aaaacaacaa ctaaattaat gtctttctat tttcaaagtt      780
ttatctccaa acctattaat agtttaattt ttttttttaa aattaggaaa ccggttaaaa      840
tatattttaa atacaaaaaa cttaaacaat gaatcattta tttatttatt cttcaaaatt      900
taaatatccg aacccggccc aaaatatccg aacccgaaca taaatatcc gaacccgact       960 cgaagtgtag aaaatatccg aacgggtttt tacctttat actgaaatac cctatacgaa      1020
cccgaatgtg tatccgaacg cccctacaa tatatgatca tcatttgtat cttgattgaa      1080
caaaaaaaaa gttaaactat tgatcacaaa attttcaatg tgagactttt accattttta      1140
gtcatttata gtcgttttta aaaattcaaa atataactta taagaaaaaa tctaattttt      1200
tttattatat gcttaatgtg attgtttaat ttcttttaat aatataaaat taaacaaaaa      1260
atgagaggtt aaaaaaattg ttatcaaata tgtattattc ataatcatta attgtcatat      1320
atatgttaat tatattaggt aatttcgtag tttttattta agaaaagaaa aaaatattat      1380
tttgtacact actaattaat ttgatagtta gtttaataaa aaatatatta tattattata      1440
tggaccaact tattttttcta aaaaaaaacc actgttttaa aaaccaaacc aactataaac      1500
cggagatata ccggattgag tggctaaaac actctttgta tatatgtgct gagcaaaccc      1560
tctgagtgag atggcgtgtt aagaagtagg aggaccattc atgcctctta tgagttgtag      1620
tctgtgtgta caaaaaagaa gcgttggtgt gaaagaaagc agaaggattt gaaaatcaaa      1680
aaaattgaag gagaagcggg aaaacaaata atctctccct ccgcttttt ttctccaaat       1740 aatcaatctc tcatttcatt tgttaaccca agttttgat aattatttca aagggtttta      1800
tttatctttt attcctccgg cggcagtaag tagtaatcaa tggcgagaac caaacatttc      1860
gcttccaggg cacgagatcg caatcgaact agttagtact ctctctctct ctgccttttt      1920
tttgatattt attttctagg ttaaacccta atttggcatc tgaaatttgt agatgcgact      1980
gcttcatctt cggcggcggc ggcggaaggt ccgagtgcgg tacgtcatct attttctttt      2040
cccgttttag gttttttacgc aaatctcgtt actgtttttt tgacgaatcg attgaaatgt      2100
gtagaccccg acgagaagag aaggcagcca aggagaagct caacagagtg agtctttcta      2160
tttcattttc tgagatccat gaatcctttt catctctcgt gtgttgtgac atgaatcaat      2220
tgcagcagca actcctacta cgactccacc agccggtaga aaagtaagtt acatttccat      2280
ttcacaccat tcatttgctt ctttatcaac aaactgctct ctcatctgtt ttttttgttt      2340
tgttttggtt ttgtgaagaa aggagggact aagcgaacta acaagctat gcctaaaagt       2400 tagtgacaga ttttaaaatc tctattttgg atcatcattc tctcaggaca tgtctatttg      2460
catttgttct tattatgtct gtctgtctgt ctttgtcccc cttgtaggtt ccaacaagaa      2520
gaagacattc cgttacaagc ctggaaccgt tgccctcaga gagattcgcc atttccagaa      2580
gaccaccaaa cttcttatcc ctgccgctag tttcatccga gaagttagta atgaactttg      2640
ttattcatac attcccgctt acttgttttc aatgactctg caattactga tatagaattt      2700
ggagcaacca ttatggggtg atttctctaa ctacaaatta ctaatactat cccaggtgag      2760
aagtgtcacc cagatctttg ccctcccga tgttacccgt tggactgctg aagctcttat       2820
ggctattcaa gaggtacgtg tactccttcc ctcttttgtt tcctattttc cacttgatgt      2880
ctaatttaaa ctgatcgttt ttttttata tttctttgg tgtggggcgg ggcaggcggc        2940
```

```
tgaagattt  ttaattggct  tgttctctga  tgctatgttt  tgcgctatcc  atgcaaggcg      3000
tgttactcta  agtaagtagt  actccccaaa  ataaggaaac  ccatttata  tacaacattg      3060 cctcatccat  gtctgcttct  cttcatatca  gtgagaaaag  attttgagct  tgcacgccgt      3120
cttggaggaa  aaggcagacc  attgtgatcg  tttcgcaggt  tgtataactt  tgttcactcc      3180
ttatgtcttg  tcatttgtga  tctgactgac  actttctttt  gaaacataac  tgcttgattc      3240
aatatctagg  ctgtaaaact  tatccctcct  tgtttactat  cttatatgct  ttttccttgg      3300
aattgatagt  ttccattgag  atttcacttg  cacgaaacat  atctgctttc  tcaatatctc      3360
tcagtcttag  aaagggctat  tgactaaaag  aaaagaaaat  ttagaggaag  atttgtaaag      3420
acatgtgttt  agagagggct  taattaaaaa  cacacgcttc  tgctagcctt  gctatttgat      3480
tcccaatttc  aacttttttc  gaggcatatt  ataaagtttt  taaatgtact  tggcacttca      3540
acttttataa  tttatataac  gattttattc  taatagagca  tttgtgattt  catagtgttg      3600
tcatgaaact  caagtaattc  acaccgtccg  atgttgctat  tgtctaataa  aatgttgaaa      3660
aaattgtcaa  acagaacaa   aaaacaacat  agttgtctct  atggtataaa  actatcacta      3720
agttgtctct  atagtataat  attttcgca   atcccaaaac  taattttct   ttaatcaaat      3780 taaacataaa  ctaaaaccat  ttttaaaaag  tttaatggaa  aaagataaaa  aaataaggta      3840
atctcgtaat  gttttaaaaa  ggaaaaaaaa  tgtaaaaaca  atttaaaaaa  aagaacacac      3900
gacacagatc  aaaaatatca  tgtaatctaa  ttgcatttgg  tttctaaaat  cttccaaaac      3960
tattctttta  aaattctcta  aggtaaaact  tgattccaat  a                          4001

<210> SEQ ID NO 78
<211> LENGTH: 540
<212> TYPE: DNA
<213> ORGANISM: Brassica napus

<400> SEQUENCE: 78
atggcgagaa  ccaaacattt  cgcttccagg  gcacgagatc  gcaatcgaac  taatgcgact       60
gcttcatctt  cggcggcggc  ggcggaaggt  ccgagtgcga  ccccgacgag  aagagaaggc      120
agccaaggag  aagctcaaca  gacaactcct  actacgactc  caccagccgg  tagaaaaaaa      180
ggagggacta  agcgaactaa  acaagctatg  cctaaaagtt  ccaacaagaa  gaagacattc      240
cgttacaagc  ctggaaccgt  tgccctcaga  gagattcgcc  atttccagaa  gaccaccaaa      300
cttcttatcc  ctgccgctag  tttcatccga  gaagtgagaa  gtgtcaccca  gatctttgcc      360
cctcccgatg  ttacccgttg  gactgctgaa  gctcttatgg  ctattcaaga  ggcggctgaa      420
gattttttaa  ttggcttgtt  ctctgatgct  atgttttgcg  ctatccatgc  aaggcgtgtt      480
actctaatga  gaaaagattt  tgagcttgca  cgccgtcttg  gaggaaaagg  cagaccattg      540

<210> SEQ ID NO 79
<211> LENGTH: 180
<212> TYPE: PRT
<213> ORGANISM: Brassica napus

<400> SEQUENCE: 79

Met Ala Arg Thr Lys His Phe Ala Ser Arg Ala Arg Asp Arg Asn Arg
1               5                   10                  15

Thr Asn Ala Thr Ala Ser Ser Ser Ala Ala Ala Ala Glu Gly Pro Ser
            20                  25                  30

Ala Thr Pro Thr Arg Arg Glu Gly Ser Gln Gly Glu Ala Gln Gln Thr
        35                  40                  45
```

```
Thr Pro Thr Thr Thr Pro Pro Ala Gly Arg Lys Lys Gly Gly Thr Lys
    50                  55                  60

Arg Thr Lys Gln Ala Met Pro Lys Ser Ser Asn Lys Lys Lys Thr Phe
 65              70                  75                  80

Arg Tyr Lys Pro Gly Thr Val Ala Leu Arg Glu Ile Arg His Phe Gln
                 85                  90                  95

Lys Thr Thr Lys Leu Leu Ile Pro Ala Ala Ser Phe Ile Arg Glu Val
            100                 105                 110

Arg Ser Val Thr Gln Ile Phe Ala Pro Pro Asp Val Thr Arg Trp Thr
        115                 120                 125

Ala Glu Ala Leu Met Ala Ile Gln Glu Ala Ala Glu Asp Phe Leu Ile
    130                 135                 140

Gly Leu Phe Ser Asp Ala Met Leu Cys Val Ile His Ala Arg Arg Val
145                 150                 155                 160

Thr Leu Met Arg Lys Asp Phe Glu Leu Ala Arg Arg Leu Gly Gly Lys
                165                 170                 175

Gly Arg Pro Leu
            180

<210> SEQ ID NO 80
<211> LENGTH: 5834
<212> TYPE: DNA
<213> ORGANISM: Zea mays

<400> SEQUENCE: 80
ttatgtagag gcaattgcag tagtgcctct gttttagagt gtaactacag atttgtccct      60
atttttttag agtttgcgtg tttgtccctg ttttttcaaa tcaaactatt gtataccct     120 actccattag ttatacttaa caatgttaag tcttgataaa aagacaaggg ataattggat     180
tagtgaccct gttttagagt gtaattatag ctttgcccga tgttttagac ttcacatgtt     240
tttatgacaa ttcaaattgt ttccataaca tcttaaatta ttttgacaac atttagaatt     300
gttttgcaat aatttaaatt attttccaaa taaaaatatt ttgacaatta ttttatcaac     360
aaattaaatt attttttttta caaaataatt tgtcaaggta ctttttttaaa attttgaaaa     420 taatcaaatt attgtaaata taatttgaat tgttgcgaaa ataatttgga ttgtcataaa     480
aacacgtaag tctaaaaatt aggcgtaaaa ctacaattat actctaaaaa ggtggtaatg     540
gcgtagttgt tccttgtcta ttttatcaag acatagcacc gtgcagtaca actaatggag     600
tagtgacata caacaatttt gttttaaata tagggggtaa atacgcaaag tctaaaaaac     660
agaggtaaat ctacaattac atgttaaaat agaggcatcg atacaattgt accttttata     720
tagcagcatg cgccctgttg ggatacaatt gtacctttca catgtcttct agatggttcc     780 caacccttttg gccaagatcg tacagataat attgcgagga gcccaaatca acggtgtcca     840
tatgttatgt tgatgtggat ggtttaccta ggcgcaaaag tgcgctggtt tcgtccgtac     900
aaatatactt taagtatggt tttgatttt ttctattttt cattttttaa ataaaacgag     960
acaatcaaat ctgatataaa aatcaaatga attataaata gagacggaaa gagtatatat    1020
atttgttttg ctattattta aagtattaaa agatagtgga cgaatgaacg tcctctatgt    1080
ttaaaagaac gttttagagg acgttgtgtt gttgaaggaa atatgaaaaa aaaatcttct    1140
gcatatttag aagggaggag cgtttacaca ttactttcgg gacttcaacc caaatatgtc    1200
aaggtttgtg agtggctcag tgcggaaaaa aaatcctata tataccagat gtaaacacta    1260
tcttttacag cctatcacat tcacatttag aggttcacaa agatagatca aaatttataa    1320
```

```
aataatcatt taatattttt tttattttat ttatatggat aagcagctgg tgtatgtgag    1380
gagctgtaaa agatattttt tacatccgag atgtaaagat ttttttttaac tcaatgctgg   1440
ttaccggctg ggaggacgat gataaagaaa gcatctctca ctgcattccg ggcccactac    1500
tcaaacgttc ggcacgccag gttggcaggt agccgttaca tcgataggca ctcggccact    1560
cgcacgcaga caccacacca gtgtgctcag tgctcactgc tcaccataat aacgctgcac    1620
ctcttttcat ttcaccatct cctgccccct taaaaaaaag actcaccgtc gacacgccct    1680
cccgtcccga gagttctgaa tcgaaaccgt cggccacgag agcagtgcga ggcgcccacc    1740
gcgatggctc gaaccaagca ccaggccgtg aggaagacgg cggagaagcc caagaagaag    1800
ctccagttcg agcgctcagg taacccgggt cccgcgctcc cccccgcttc gcaagcagac    1860
gctgtcgctt ctctccgacc ctggtgctaa gcacgttcct tgttccgtct tttgcaggtg    1920
gtgcgagtac ctcggcgacg ccggtgagcg cgtgcgtgcg gggatcagtt ccctccttt    1980
gcctttttt gttgggctgc tcttacttgc ttgcaagctg tttgatggaa tgcaggaaag    2040
ggctgctggg accgggggaa gagcggcgtc tggaggtgac tcaggtgagg acctatttgt    2100
cgttgctgga tgctgggttt cgcttgcaat ctaattttgt tgcaagatga gggcgaatgt    2160
gccagttcca tgtgggtgtc atggtctcgg agttactacc ttaattgctc accatagtat    2220
gttttcttaa aaaaaacagt taagaagacg aaaccacgcc accgctggcg gccagggact    2280
gtagcgctgc gggagatcag gaagtaccag aagtccactg aaccgctcat cccctttgcg    2340
cctttcgtcc gtgtggtggg tgcaggcgtg tttgtcctct gcatagtatg gggttgttcc    2400
gcattctgtc taatggaaag ttattcttct gagaaaaaaa atgcaggtga gggagttaac    2460
caatttcgta acaaacggga aagtagagcg ctataccaca gaagccctcc ttgcgctgca    2520
agaggtcagt tatgaaaaat gtcttatctc tctgttaaga tcctcttcat atacatagtt    2580
gctattgcta tcgtgaagtc ttttttttct gttaattggt ctggtactac ttactagtca    2640
ggatttcata ttgcggtttt tcctagtggt gtgtagttaa aaagtagttt aattgctttt    2700
agttaaaagg ggtgttcagg gctaaagatc aactatgaga aaacagaaat tttcccaatt    2760
cgatacccga cagcattatg gcctgcgcta atggaggtgt ttccgggcaa atactctagc    2820
ctacctggga agtaccttgg gttgcccctt catttcagga aagtaaaaag gaatgatctt    2880
caacctctaa tcgaaaaaat caacaacagg ctggccttgc tggaaaggca agatgttgtc    2940
caaggctggt atagaaactc ttgtaaaatc gatgctatcc gcacaaccaa tctaccatct    3000
aatggttttt ccacctcaaa aatggctgct gcaaacaatt gacaaaatac gaagaaactt    3060
cctgtggaga gggagcaatc cagaagtttg cagcgggggt cactgcctcg tcaactggcc    3120
cgtaacttgc ctcccaaaga acaagggagg tcttggaatt ctggaccttg atcgttttgc    3180
gaggggggcta agactaagat ggctgtggct acgatggaag agcaaagata gggcgtggac    3240
tgccttgaag cttccttgtg acaaaactga tgaagatctc ttcaatgctt ccacaactgt    3300
cacggtaggc aatggaaaga tagctgaatt ctggaattct agttggatcc aaggccaagc    3360
ccctaagaac attgcgccaa cactgttcaa gaaggaaaag aggaagaaca tcacggtcgc    3420
caaagcgctc actaacaaca attggattcg tttatgctca ccatacacgg gtgaggggga    3480
gtttagagag gtcgtctctc tttggcaggc cataggtaac atgcaagagc ttaacggttt    3540
ggaagacaac atctccttgga gatggacggc agatgggcag tacagtgcta gcagtgcata    3600
caaaatccag ttcgcatcca atttcactaa aatgaacctc tgccctattt ggaaggctaa    3660
```

```
agtggaaccg aaatgccgat tttttgcttg gacactactt cataagagaa ttctgactgc    3720
cgataacctt cataaaagag gttgcaactc agcctcagaa acaattcccc acttatgcaa    3780
ggattgcccc tttagtagag aggtgtggaa caaagttttg tctcgggcca actttccttt    3840
actgactggg tctcccagtg acacttcttt gtatgattgg tggacggaca tgtgcagcct    3900
ttgcagcaga caggcaagaa gaggtttcga cggtctgcta tttcactttt ggtggaactt    3960
atggctggaa agaaataaca gaatctttca aaggcagcgt agaagtgtag atcaagttgc    4020
tctggcagtc aaggattatg ctagtagctg aagtctagtt ggtttggact agtggttttg    4080
ttgcttttct ttttaatttc tttttagttc tttttatgtt gttttcgttt ccttaagttg    4140
cttggagtct gtattatcct ctttcttcta atatagatcg gagcgacaaa ccttttgccc    4200
cttcctttca aaaaaagtt aaagggaat ttaactgctt tcctagtggt gtagttaaaa     4260
tggatttcat attgcggcct ttcctagctt gcttgctatt gattggacta tagtgatcca    4320
aatgctgata actttgtcgc ttgtgtaggc atggttagag agcttagagt ttgcatttat    4380
tcaatacctt gagactgcat ttcatataca taaattattc atgattattt cttttctcta    4440
tttgttctgg ttaattaaga gttttaggtt tccatatttt tgtacgtgca tcatttaaat    4500
tcttgtattg tttttcgttc ttgtctacag gcagcagaat tccacttgat agaactgttt    4560
gaaatggcga atctgtgtgc catccatgcc aagcgtgtca caatcagtaa gttatcactg    4620
agtgaactcc tttttctctg tagcattact cctaatgaat atgtgtgatg catttttggtt   4680
gcacgattct ttagtgattc tgcttcagat ggatatgata aatctagatg ttattttgaa    4740
gtggcgaatt gcttacgagc ggaaatagta atgttcaaat agcgcaaagt gcaactgttg    4800
acttttagta ggccatttat atggtttgat taccaacaaa tacgtcaatc atatgatttg    4860
attatcaaca aaggaatcag ctatatggtt tgattatcaa caaggaatc agctaggttt    4920
gcttatcaac attcaacaaa ggcatcaagt aatactccat ccgtttcaat ttataattcg    4980
tttgactttt tttatctaag tttgatcggc tcgacttatt aaaaaaaatc ataattattg    5040
ttaattttg ttgtgatatt gtttagtata atatacttta aatgtgactt tgagttttc     5100
attttttcgc aaaaaaaaat gaataggacg agccggtcaa acgtgacaca aaaaagtcaa    5160
acgaattata atttgggaca cacggagtag taaataatgt aacaacttag agagtgggac    5220
aaaaaaatct ctagtggtgc taaatttagt tcagctttgt ataaacacaa gcattgattg    5280
agaaatctga caactcaagg atctgtagga aatgtgttac cctaaatgtt ttccttactg    5340
atgcagtgca aaaggacata caacttgcaa ggcgtatcgg aggaaggcgt tgggcatgat    5400
atataatatc cattctgatt gcatcattct tgtgaatttg tttgtaggag ctagacatta    5460
gtgttgttga atgctgcatg gttcctaatc cttttcgcag tctaacatct gtggagttag    5520
tatgttacat ggcaacagct gaacatctgt ggactatatg gcaacagccg aagattgtgt    5580
ctgtgggata actggttgtt ttggttgctc ttcagtagtt tgtttgcttc aggtaaccat    5640
gctgcgaact atgatgtttt cattctcggt ttgcttcagc taaccgagat cgattcagtc    5700
tgcagtatgg actatggagt aaactgcatg ctgaaacccg aaccactgct gaaactgcat    5760
gctgaaaccc gaaccactgc tacggcagtt gccaggatag caggagggcc tttatgcaca    5820
gtggaattga gtag                                                     5834
```

<210> SEQ ID NO 81
<211> LENGTH: 471
<212> TYPE: DNA
<213> ORGANISM: Zea mays

<400> SEQUENCE: 81

```
atggctcgaa ccaagcacca ggccgtgagg aagacggcgg agaagcccaa gaagaagctc      60
cagttcgagc gctcaggtgg tgcgagtacc tcggcgacgc cggaaagggc tgctgggacc     120
gggggaagag cggcgtctgg aggtgactca gttaagaaga cgaaaccacg ccaccgctgg     180
cggccaggga ctgtagcgct gcgggagatc aggaagtacc agaagtccac tgaaccgctc     240 atccccttg cgcctttcgt ccgtgtggtg agggagttaa ccaatttcgt aacaaacggg      300
aaagtagagc gctataccac agaagccctc cttgcgctgc aagaggcagc agaattccac     360 ttgataaac tgtttgaaat ggcgaatctg tgtgccatcc atgccaagcg tgtcacaatc      420
atgcaaaagg acatacaact tgcaaggcgt atcggaggaa ggcgttgggc a              471
```

<210> SEQ ID NO 82
<211> LENGTH: 157
<212> TYPE: PRT
<213> ORGANISM: Zea mays

<400> SEQUENCE: 82

```
Met Ala Arg Thr Lys His Gln Ala Val Arg Lys Thr Ala Glu Lys Pro
1               5                   10                  15

Lys Lys Lys Leu Gln Phe Glu Arg Ser Gly Gly Ala Ser Thr Ser Ala
            20                  25                  30

Thr Pro Glu Arg Ala Ala Gly Thr Gly Gly Arg Ala Ala Ser Gly Gly
        35                  40                  45

Asp Ser Val Lys Lys Thr Lys Pro Arg His Arg Trp Arg Pro Gly Thr
    50                  55                  60

Val Ala Leu Arg Glu Ile Arg Lys Tyr Gln Lys Ser Thr Glu Pro Leu
65                  70                  75                  80

Ile Pro Phe Ala Pro Phe Val Arg Val Arg Glu Leu Thr Asn Phe
                85                  90                  95

Val Thr Asn Gly Lys Val Glu Arg Tyr Thr Thr Glu Ala Leu Leu Ala
            100                 105                 110

Leu Gln Glu Ala Ala Glu Phe His Leu Ile Glu Leu Phe Glu Met Ala
        115                 120                 125

Asn Leu Cys Ala Ile His Ala Lys Arg Val Thr Ile Met Gln Lys Asp
    130                 135                 140

Ile Gln Leu Ala Arg Arg Ile Gly Gly Arg Arg Trp Ala
145                 150                 155
```

<210> SEQ ID NO 83
<211> LENGTH: 5834
<212> TYPE: DNA
<213> ORGANISM: Zea mays

<400> SEQUENCE: 83

```
ttatgtagag gcaattgcag tagtgcctct gttttagagt gtaactacag atttgtccct      60
atttttttag agtttgcgtg tttgtccctg ttttttcaaa tcaaactatt gtataccct     120 actccattag ttatacttaa caatgttaag tcttgataaa aagacaaggg ataattggat     180
tagtgaccct gttttagagt gtaattatag ctttgcccga tgttttagac ttcacatgtt     240
tttatgacaa ttcaaattgt ttccataaca tcttaaatta ttttgacaac atttagaatt     300
gttttgcaat aatttaaatt atttccaaaa taaaaatatt ttgacaatta ttttatcaac     360
aaattaaatt attttttta caaaataatt tgtcaaggta ctttttaaa attttgaaaa       420
```

```
taatcaaatt attgtaaata taatttgaat tgttgcgaaa ataatttgga ttgtcataaa    480
aacacgtaag tctaaaaatt aggcgtaaaa ctacaattat actctaaaaa ggtggtaatg    540
gcgtagttgt tccttgtcta ttttatcaag acatagcacc gtgcagtaca actaatggag    600
tagtgacata caacaatttt gttttaaata ataggggtaa atacgcaaag tctaaaaaac    660
agaggtaaat ctacaattac atgttaaaat agaggcatcg atacaattgt accttttata    720
tagcagcatg cgccctgttg ggatacaatt gtacctttca catgtcttct agatggttcc    780 caacccttg gccaagatcg tacagataat attgcgagga gcccaaatca acggtgtcca    840
tatgttatgt tgatgtggat ggtttaccta ggcgcaaaag tgcgctggtt tcgtccgtac    900
aaatatactt taagtatggt tttgattttt ttctattttt catttttaa ataaaacgag     960 acaatcaaat ctgatataaa aatcaaatga attataaata gagacggaaa gagtatatat   1020
atttgttttg ctattattta agtattaaa agatagtgga cgaatgaacg tcctctatgt    1080 ttaaagaac gttttagagg acgttgtgtt gttgaaggaa atatgaaaaa aaaatcttct    1140
gcatatttag aagggaggag cgtttacaca ttactttcgg gacttcaacc caaatatgtc   1200
aaggtttgtg agtggctcag tgcggaaaaa aaatcctata tataccagat gtaaacacta   1260
tcttttacag cctatcacat tcacatttag aggttcacaa agatagatca aaatttataa   1320
aataatcatt taatatttt tttatttttat ttatatggat aagcagctgg tgtatgtgag   1380
gagctgtaaa agatatttt tacatccgag atgtaaagat ttttttaac tcaatgctgg    1440 ttaccggctg ggaggacgat gataaagaaa gcatctctca ctgcattccg ggcccactac   1500
tcaaacgttc ggcacgccag gttggcaggt agccgttaca tcgataggca ctcggccact   1560
cgcacgcaga caccacacca gtgtgctcag tgctcactgc tcaccataat aacgctgcac   1620
ctcttttcat ttcaccatct cctgccccct taaaaaaaag actcaccgtc gacacgccct   1680
cccgtcccga gagttctgaa tcgaaaccgt cggccacgag agcagtgcga ggcgcccacc   1740
gcgatggctc gaaccaagca ccaggccgtg aggaagacgg cggagaagcc caagaagaag   1800
ctccagttcg agcgctcagg taacccgggt cccgcgctcc ccccgcttc gcaagcagac    1860 gctgtcgctt ctctccgacc ctggtgctaa gcacgttcct tgttccgtct tttgcaggtg   1920
gtgcgagtac ctcggcgacg ccggtgagcg cgtgcgtgcg gggatcagtt ccctcctttt   1980
gccttttttt gttgggctgc tcttacttgc ttgcaagctg tttgatggaa tgcaggaaag   2040
ggctgctggg accgggggaa gagcggcgtc tggaggtgac tcaggtgagg acctatttgt   2100
cgttgctgga tgctgggttt cgcttgcaat ctaattttgt tgcaagatga gggcgaatgt   2160
gccagttcca tgtgggtgtc atggtctcgg agttactacc ttaattgctc accatagtat   2220
gttttcttaa aaaaaacagt taagaagacg aaaccacgcc accgctggcg ccagggact    2280 gtagcgctgc gggagatcag gaagtaccag aagtccactg aaccgctcat cccctttgcg   2340
cctttcgtcc gtgtggtggg tgcaggcgtg tttgtcctct gcatagtatg gggttgttcc   2400
gcattctgtc taatggaaag ttattcttct gagaaaaaaa atgcaggtga gggagttaac   2460
caatttcgta acaaacggga aagtagagcg ctataccgca gaagccctcc ttgcgctgta   2520
agaggtcagt tatgaaaaat gtcttatctc tctgttaaga tcctcttcat atacatagtt   2580
gctattgcta tcgtgaagtc ttttttttct gttaattggt ctggtactac ttactagtca   2640
ggatttcata ttgcggtttt tcctagtggt gtgtagttaa aaagtagttt aattgctttt   2700
agttaaaagg ggtgttcagg gctaaagatc aactatgaga aaacagaaat tttcccaatt   2760
cgatacccga cagcattatg gcctgcgcta atggaggtgt ttccgggcaa atactctagc   2820
```

```
ctacctggga agtaccttgg gttgcccctt catttcagga aagtaaaaag gaatgatctt    2880
caacctctaa tcgaaaaaat caacaacagg ctggccttgc tggaaaggca agatgttgtc    2940
caaggctggt atagaaactc ttgtaaaatc gatgctatcc gcacaaccaa tctaccatct    3000
aatggttttt ccacctcaaa aatggctgct gcaaacaatt gacaaaatac gaagaaactt    3060
cctgtggaga gggagcaatc cagaagtttg cagcgggggt cactgcctcg tcaactggcc    3120
cgtaacttgc ctcccaaaga acaagggagg tcttggaatt ctggaccttg atcgttttgc    3180 gaggggcta agactaagat ggctgtggct acgatggaag agcaaagata gggcgtggac    3240
tgccttgaag cttccttgtg acaaaactga tgaagatctc ttcaatgctt ccacaactgt    3300
cacggtaggc aatggaaaga tagctgaatt ctggaattct agttggatcc aaggccaagc    3360
ccctaagaac attgcgccaa cactgttcaa gaaggaaaag aggaagaaca tcacggtcgc    3420
caaagcgctc actaacaaca attggattcg tttatgctca ccatacacgg gtgaggggga    3480
gtttagagag gtcgtctctc tttggcaggc cataggtaac atgcaagagc ttaacggttt    3540
ggaagacaac atctcttgga gatggacggc agatgggcag tacagtgcta gcagtgcata    3600
caaaatccag ttcgcatcca atttcactaa aatgaacctc tgccctattt ggaaggctaa    3660
agtggaaccg aaatgccgat tttttgcttg gacactactt cataagagaa ttctgactgc    3720
cgataacctt cataaaagag gttgcaactc agcctcagaa acaattcccc acttatgcaa    3780
ggattgcccc tttagtagag aggtgtggaa caaagttttg tctcgggcca actttccttt    3840
actgactggg tctcccagtg cacttctttt gtatgattgg tggacggaca tgtgcagcct    3900
ttgcagcaga caggcaagaa gaggtttcga cggtctgcta tttcacttt ggtggaactt    3960 atggctggaa agaaataaca gaatctttca aaggcagcgt agaagtgtag atcaagttgc    4020
tctggcagtc aaggattatg ctagtagctg aagtctagtt ggtttggact agtggttttg    4080
ttgcttttct tttttaatttc ttttttagttc ttttttatgtt gttttcgttt ccttaagttg    4140
cttggagtct gtattatcct cttcttcta atatagatcg gagcgacaaa ccttttgccc    4200
cttcctttca aaaaaagtt aaagggaat ttaactgctt tcctagtggt gtagttaaaa    4260
tggatttcat attgcggcct ttcctagctt gcttgctatt gattggacta tagtgatcca    4320
aatgctgata actttgtcgc ttgtgtaggc atggttagag agcttagagt ttgcatttat    4380 tcaataccctt gagactgcat ttcatataca taaattattc atgattattt cttttctcta    4440
tttgttctgg ttaattaaga gttttaggtt tccatatttt tgtacgtgca tcatttaaat    4500
tcttgtattg ttttttcgttc ttgtctacag gcagcagaat tccacttgat agaactgttt    4560
gaaatggcga atctgtgtgc catccatgcc aagcgtgtca caatcagtaa gttatcactg    4620
agtgaactcc tttttctctg tagcattact cctaatgaat atgtgtgatg cattttggtt    4680
gcacgattct ttagtgattc tgcttcagat ggatatgata aatctagatg ttatttttgaa    4740 gtggcgaatt gcttacgagc ggaaatagta atgttcaaat agcgcaaagt gcaactgttg    4800
acttttagta ggccatttat atggtttgat taccaacaaa tacgtcaatc atatgatttg    4860
attatcaaca aaggaatcag ctatatggtt tgattatcaa caaggaatc agctaggttt    4920 gcttatcaac attcaacaaa ggcatcaagt aatactccat ccgtttcaat ttataattcg    4980
tttgactttt tttatctaag tttgatcggc tcgacttatt aaaaaaaatc ataattattg    5040 ttaattttg ttgtgatatt gtttagtata atatactttta aatgtgactt tgagttttc    5100 attttttcgc aaaaaaaat gaataggacg agccggtcaa acgtgacaca aaaaagtcaa    5160
```

| | |
|---|---|
| acgaattata atttgggaca cacggagtag taaataatgt aacaacttag agagtgggac | 5220 |
| aaaaaaatct ctagtggtgc taaatttagt tcagctttgt ataaacacaa gcattgattg | 5280 |
| agaaatctga caactcaagg atctgtagga aatgtgttac cctaaatgtt ttccttactg | 5340 |
| atgcagtgca aaaggacata caacttgcaa ggcgtatcgg aggaaggcgt tgggcatgat | 5400 |
| atataatatc cattctgatt gcatcattct tgtgaatttg tttgtaggag ctagacatta | 5460 |
| gtgttgttga atgctgcatg gttcctaatc cttttcgcag tctaacatct gtggagttag | 5520 |
| tatgttacat ggcaacagct gaacatctgt ggactatatg caacagccg aagattgtgt | 5580 |
| ctgtgggata actggttgtt ttggttgctc ttcagtagtt tgtttgcttc aggtaaccat | 5640 |
| gctgcgaact atgatgtttt cattctcggt ttgcttcagc taaccgagat cgattcagtc | 5700 |
| tgcagtatgg actatggagt aaactgcatg ctgaaacccg aaccactgct gaaactgcat | 5760 |
| gctgaaaccc gaaccactgc tacggcagtt gccaggatag caggagggcc tttatgcaca | 5820 |
| gtggaattga gtag | 5834 |

<210> SEQ ID NO 84
<211> LENGTH: 471
<212> TYPE: DNA
<213> ORGANISM: Zea mays

<400> SEQUENCE: 84

| | |
|---|---|
| atggctcgaa ccaagcacca ggccgtgagg aagacggcgg agaagcccaa gaagaagctc | 60 |
| cagttcgagc gctcaggtgg tgcgagtacc tcggcgacgc cggaaagggc tgctgggacc | 120 |
| ggggaagag cggcgtctgg aggtgactca gttaagaaga cgaaaccacg ccaccgctgg | 180 |
| cggccaggga ctgtagcgct gcgggagatc aggaagtacc agaagtccac tgaaccgctc | 240 |
| atccccttg cgcctttcgt ccgtgtggtg agggagttaa ccaatttcgt aacaaacggg | 300 |
| aaagtagagc gctataccgc agaagccctc cttgcgctgt aagaggcagc agaattccac | 360 |
| ttgatagaac tgtttgaaat ggcgaatctg tgtgccatcc atgccaagcg tgtcacaatc | 420 |
| atgcaaaagg acatacaact tgcaaggcgt atcggaggaa ggcgttgggc a | 471 |

<210> SEQ ID NO 85
<211> LENGTH: 113
<212> TYPE: PRT
<213> ORGANISM: Zea mays

<400> SEQUENCE: 85

```
Met Ala Arg Thr Lys His Gln Ala Val Arg Lys Thr Ala Glu Lys Pro
1               5                   10                  15
Lys Lys Lys Leu Gln Phe Glu Arg Ser Gly Gly Ala Ser Thr Ser Ala
            20                  25                  30
Thr Pro Glu Arg Ala Ala Gly Thr Gly Gly Arg Ala Ala Ser Gly Gly
        35                  40                  45
Asp Ser Val Lys Lys Thr Lys Pro Arg His Arg Trp Arg Pro Gly Thr
    50                  55                  60
Val Ala Leu Arg Glu Ile Arg Lys Tyr Gln Lys Ser Thr Glu Pro Leu
65                  70                  75                  80
Ile Pro Phe Ala Pro Phe Val Arg Val Arg Glu Leu Thr Asn Phe
                85                  90                  95
Val Thr Asn Gly Lys Val Glu Arg Tyr Thr Ala Glu Ala Leu Leu Ala
                100                 105                 110
Leu
```

<210> SEQ ID NO 86
<211> LENGTH: 3060
<212> TYPE: DNA
<213> ORGANISM: Sorghum bicolor

<400> SEQUENCE: 86

| | | | | | |
|---|---|---|---|---|---|
| catctctcac | tgccatccgg | gtccactact | cccaacgttc | ggcacgccag | gtatagccgt | 60 |
| taccccggta | ggccccactg | gtacacggac | aaaggttagc | ggtcaccgcg | aatcgtgaat | 120 |
| acttgtgact | acggggtgct | aattataaaa | acgccgcaca | tcctttcgtt | tcgccatttc | 180 |
| accccccttc | ccttcccgta | gagaggaaaa | aaacccaccg | tcgacccgcc | cggccgcccg | 240 |
| agagttctga | atcgaaaccg | tcggccgcga | ccgcgagagc | agcgcggggc | gcccaccgtg | 300 |
| atggctcgaa | ccaagcacca | ggccgtgagg | aagctgccgc | agaagcccaa | gaagaagctc | 360 |
| cagttcgagc | gcgcaggtaa | gcccgcgtcc | ccgcgctgaa | ccccctccg | cctcgcgagc | 420 |
| agacgctgcc | gctgctctcc | gtcgcccctg | gtgctaagcg | cgttccttttt | ttttccttct | 480 |
| tttgcaggtg | gggcgagtac | gtcggcgacc | ccggtgagtg | cgtgcgtgcg | tgcgggaatt | 540 |
| ggttttagcc | ctccttttgc | ggtttcgcct | tttgttgggc | tggtctcact | tgcttgcaat | 600 |
| ctgtttgatg | gaatgcagga | gaggaggaat | gctgggaccg | ggggaggagc | cgcggctcgc | 660 |
| ggtgaggatc | tctttgtcgt | tgctgggttt | gggaatttcc | ggcgcgaaat | tatgtggatt | 720 |
| tctaggttta | tctgccgtct | ttcttcttgt | cttctctttt | ggctctgggg | tgagaagtta | 780 |
| gggtggttgg | gcggacatgg | tgcgttattt | cgccgtatcg | tttggtttgg | tgctttctca | 840 |
| tccttttaat | tccaacatgc | cttgtaaaaa | ttgcacaaga | tttgttttttt | catgcatgtc | 900 |
| tcagtgttgc | taatttgctt | ttccggttcg | gttggtagaa | ttcaatttct | tggcgcaata | 960 |
| tgcatcttct | tttgttgcaa | catgagggcg | aatgtgccag | ttccatatgg | gcgtcgcggt | 1020 |
| tttgaagtta | ctaccttgct | tgctcttcgt | attataggcg | tcattcacaa | tagtatgttt | 1080 |
| tcttggagat | gcagttgcac | ggggcgtgt | ggagaagaag | catcgctggc | gggcagggac | 1140 |
| tgtagcgctg | cgggagatca | ggaagtacca | gaagtccact | gagccgctca | tccccttttgc | 1200 |
| gcccttcgta | cgtgtggtgg | gtgcatcttg | taccaattgt | tgtccactcc | atagaatggg | 1260 |
| tttgttctgc | agtctgtctg | atggaaagtt | attcttctga | gaaaaaatgc | aggtcaaaga | 1320 |
| gttaactgta | ttcataacag | actggaggat | agggcgctac | acccctgaag | ccctccttgc | 1380 |
| gctgcaagag | gtcagttatg | aaacatgtct | tgtgtatcag | ttaagatcat | cttctataga | 1440 |
| cataattgtt | atcatgaagt | cttttttctgt | taatcggtct | ggtactactt | aataatcagg | 1500 |
| atttcagatt | gctgcctttc | ctagtggtgt | agtcaaaagg | gaatttaagt | gctgttaggt | 1560 |
| actgtttgtt | ttggtgtttt | gaaccctgcc | gcgatcggtt | gttgttattc | catgtttgtt | 1620 |
| tctgtggcag | cggacgttca | cggtgagatg | ggatacgggc | gtgtgaaaca | tagttacggt | 1680 |
| ccatcttcat | ggcttatcca | tttacgctgc | tcgtccgctc | acttgttatg | tgcggcaacc | 1740 |
| aaacttttgt | tactagtgta | actggtagcg | ttgcaaatct | ttccatttgc | gttaccactc | 1800 |
| cctatgggag | ccaaacagca | ccttagtgta | gattccattt | gtattacttg | agctagcttc | 1860 |
| cttgctattg | gtgcctcgat | tgtactgtta | tgatcgaagt | gctgaaaact | ttgtcgcctg | 1920 |
| catagcatga | ttagagaact | tgagtttaca | tttattcaat | accttaagac | tgcatttcgt | 1980 |
| atagataaat | tatttttcct | aattgttctg | gttaactgtt | ttaggtttcc | atattttgt | 2040 |
| atgtgtatca | tttaaattat | tgtgttgttt | ttcctccctg | tctacaggca | gcagaattcc | 2100 |
| acttgataga | actgtttgaa | gtggcgaatc | tgtgtgccat | ccatgccaag | cgcgtaacag | 2160 |

```
tcagtaagtt atcactgaat gaactccttt tcctctgtac tattacgcct aatggagatg    2220
tgtgatgcat ttttggttac acgattcttt agtgattctg cttcagttgg atatgataaa    2280
tctagatgtt atttaaagtg gcaaattgct tacgagtgga aatagtaatg ttcaaatagt    2340
gaaaagtgca attaaacttt taataggcca ttatatggtt tgattgtcaa caaatgcatc    2400
aagaaatagt aaatattata acagttatgg cttagagagt ggacaaaaaa tcggtaatgg    2460
tgagctttgt ataaacacta aaactggctg agaaatctga taactcaagg atctatagga    2520
aatgtattat cctaaatgtt ttccttcctg ctgcagtgca aaaggacata caacttgcaa    2580
ggcgtatcgg aggaaggcgt tggtcgtgat atccattctg attctgatta ccttgttcgg    2640
gtggaatttg tttagaggag ttagacatta gtcttgttga atgctgtgca tggttcctaa    2700
tctgtttcac agttagtggg ctcttctggg atgatctgtt aacacctgtg gagtatgtta    2760
tgtaggaaac acctgaactg aacaacccaa agttgttttg gttgctcttc aaccatttgt    2820
ttgcttcaga gatcgattct aaactgcatg ctaattagtc tatggttgaa caaaaattat    2880
caaatataaa tgaaagtgat atagtagcaa aatccaaaaa aaaaaggatc caaacaaggc    2940
ctaaaatcat ggttctttct ccttttgaac tgggtgcaag tatggacagg cacagaagaa    3000
aaccgcctag caaaccgttt gttttttttt cttcgttgta ccacacgaca ctgttcgttc    3060
```

<210> SEQ ID NO 87
<211> LENGTH: 471
<212> TYPE: DNA
<213> ORGANISM: Sorghum bicolor

<400> SEQUENCE: 87

```
atggctcgaa ccaagcacca ggccgtgagg aagctgccgc agaagcccaa gaagaagctc      60
cagttcgagc gcgcaggtgg ggcgagtacg tcggcgaccc cggagaggag gaatgctggg     120
accgggggag gagccgcggc tcgcgttgca cgggggcgtg tggagaagaa gcatcgctgg     180
cgggcaggga ctgtagcgct gcgggagatc aggaagtacc agaagtccac tgagccgctc     240
atcccctttg cgcccttcgt acgtgtggtc aaagagttaa ctgtattcat aacagactgg     300
aggatagggc gctacacccc tgaagccctc cttgcgctgc aagaggcagc agaattccac     360
ttgatagaac tgtttgaagt ggcgaatctg tgtgccatcc atgccaagcg cgtaacagtc     420
atgcaaaagg acatacaact tgcaaggcgt atcggaggaa ggcgttggtc g             471
```

<210> SEQ ID NO 88
<211> LENGTH: 157
<212> TYPE: PRT
<213> ORGANISM: Sorghum bicolor

<400> SEQUENCE: 88

```
Met Ala Arg Thr Lys His Gln Ala Val Arg Lys Leu Pro Gln Lys Pro
1               5                   10                  15

Lys Lys Lys Leu Gln Phe Glu Arg Ala Gly Gly Ala Ser Thr Ser Ala
            20                  25                  30

Thr Pro Glu Arg Arg Asn Ala Gly Thr Gly Gly Ala Ala Ala Arg
        35                  40                  45

Val Ala Arg Gly Arg Val Glu Lys Lys His Arg Trp Arg Ala Gly Thr
    50                  55                  60

Val Ala Leu Arg Glu Ile Arg Lys Tyr Gln Lys Ser Thr Glu Pro Leu
65                  70                  75                  80

Ile Pro Phe Ala Pro Phe Val Arg Val Val Lys Glu Leu Thr Val Phe
```

|  |  | 85 |  |  | 90 |  |  | 95 |  |
|---|---|---|---|---|---|---|---|---|---|

Ile Thr Asp Trp Arg Ile Gly Arg Tyr Thr Pro Glu Ala Leu Leu Ala
                      100                      105                    110

Leu Gln Glu Ala Ala Glu Phe His Leu Ile Glu Leu Phe Glu Val Ala
        115                      120                    125

Asn Leu Cys Ala Ile His Ala Lys Arg Val Thr Val Met Gln Lys Asp
    130                      135                    140

Ile Gln Leu Ala Arg Arg Ile Gly Gly Arg Arg Trp Ser
145                  150                    155

<210> SEQ ID NO 89
<211> LENGTH: 8400
<212> TYPE: DNA
<213> ORGANISM: Beta vulgaris

<400> SEQUENCE: 89

| ctactctttc | tctctctctc | tctctccatt | tctgtttgaa | atcatgagag | ttaaacacac | 60 |
|---|---|---|---|---|---|---|
| tgctgccagg | aaatcaacca | ccaacggtcc | tcgttcaagt | tagtttcctc | tctcttcttc | 120 |
| ttttttgttc | gcattctctc | aatctatatt | tcaaatttga | aaaaaattgt | gatgctcata | 180 |
| aaccctaaaa | ttttcttgta | cagaggctca | gaaatctccg | cgcagtttgc | aatcaccaca | 240 |
| atcggttctc | tctttgtact | tttgatttgt | ttttccttca | tttgttcgat | gaatggctct | 300 |
| taattgtctt | ttatttactt | gaaaattgca | gccttcctagt | agttcaaagc | gcaaatcact | 360 |
| cagaaacact | gatgcaactc | ctcaaagtaa | cttttctctt | aatattaggt | ttaattttac | 420 |
| tgctgtttgc | caaattctgt | tgaaattgta | aaatatttt | tttcttaaat | ttgacggttt | 480 |
| cagagaagaa | ggcttaccgc | cgtaagccgg | gcactgtggc | actctgggaa | atacgcaaat | 540 |
| tcagaagtc | attcaagccc | ttgattcctg | ctgcgccttt | cattcgaaca | gtatgtattt | 600 |
| tttttgtttg | tacttaataa | atgaattttg | gactggtgtt | tgtgtggctg | catagaaata | 660 |
| tatttccata | caactgaaat | tgtcctagga | ggtatcgatg | aatgtttgct | acaaaataaa | 720 |
| taaatataag | tgattatatc | ttgttaaaaa | gccattataa | ttgcaactta | tatgtatgtt | 780 |
| gtaatgaggt | caactagcta | ttttgtgcaa | agtcacccac | actttaacat | aattttgtgc | 840 |
| tctcgtaacc | ttaaaaaaat | ataagtaaag | ggttgatttg | gtctaattag | agctgatgaa | 900 |
| acccaattag | attgaaacat | aaggtgaaat | caggtggtga | tcagcttcaa | ttagatctaa | 960 |
| taagtgcagt | ttagtttagc | ttcggtgaaa | tgaacacacc | cttaaagata | gaaaatcgac | 1020 |
| actatatatg | gtccttttta | gatatgatag | ttcgatattc | tgttttgggg | tgtgttgaat | 1080 |
| gattaaatgg | agtggtgaat | agctgatggg | aactagagaa | gatgctcagt | agacagttat | 1140 |
| tgtggagact | atattactga | ttaccctgt | ttctgagtgg | ttaggacaat | gtgacaattg | 1200 |
| attttgggta | ttatttgtag | atgttttct | ttttgttaaa | agtgccaaga | taggtgtgca | 1260 |
| gttgctgatt | ctcagtttgc | taagaattag | ctgtgtctgt | atttcgtacc | tcagttgatt | 1320 |
| ctaagtgaac | atttctttga | attgatgctt | tgttcttgca | tcatgcaact | tggtgaagct | 1380 |
| ttcttgtagt | tgctccagtg | gcaatctagt | ctggtatgtt | tagaactctt | gtgatggtat | 1440 |
| gagttcatca | agatattggt | gatccaatta | gcctaaccaa | tgttttttac | ccctattgt | 1500 |
| cactgactta | tactcccctta | tctataaaaa | taattgtgac | attgatccat | ctcctcacaa | 1560 |
| tcattaatat | tatatgtact | gaccatcttt | acactctcaa | cactgaatct | aagtagggga | 1620 |
| attttgggaa | attcaatgat | gaactagtac | acccttcttc | ccaataatat | tgttgacctt | 1680 |
| tttattttga | tttgtcccat | attgtcctct | ttggtaattt | aatgtatatt | cacccaattt | 1740 |

```
tcttttcaat acccactata ccaacatata attggttaat tcatttttat taattatatt    1800
tcctaagagc ttgttgtgta aacgtggatg aatttgtagg catggatgaa gtattgttat    1860
aatgaggtga caacattact taatttcgaa ctgagggaca gagggatatg atgataaaac    1920 aactttttgct tgcttcttaa actcagaaga tagggtttac accaagtggc atgtaaaagt    1980
cactagatga ttatctatta caagggcttg tacaatctga agtacgatag gatttgaagt    2040
taacaacatt catcgaaagc tcataacttg tccttatatc aatataagtt gctggcatgt    2100
gaaattgcgt tgcaagcatc catgagctag ctcaactatt aactattaaa ctttatattt    2160
ttgcttgatc tagtatgagt cctactattt agtttctcca tctaccttaa tatgtcgcat    2220
acaccaacta atcattatcg ctagaatcaa taaacaaagc tttctttcct taggtgtatt    2280
agtacctagc tcctgtaata ccaagagcac ccaaattggg aagaaaaagt agaattggct    2340
catatctcta atcctacatt gatcattgaa aaggacctta aggttctcat actgaaacat    2400
catctttttg agcaggatat ctacgtagac gacaagaaag actactttgg ttgcccgtgc    2460
atttgagtgc atcagacaac ttctttacca ctgtctaacg gcttgctttg gccatattgt    2520
ggtcttctat gccaaaatta atgatatttc ttggcaccgc gctaatgata ttactgaatg    2580
cggatatcgt acgattagaa tttattcaaa gtaggtagca attactagtt ttgagcattg    2640
agtttcaata attagtaaat taagtgctaa acttgtacat tttggctaca tgtatttgaa    2700
ttagaattgg tacgaggaaa tatagcaaca ttacgggcaa tgttcactca agtagaagcc    2760
attacatcaa atagtactag ttgaagtatt agttctcata atactaatca ttgtcattaa    2820
tggaatattg gaacgtaaat gcctttaagg tgctgtagtt ttagtagaaa ttctactatt    2880
ctagtatgat aatgcaattt attgaaactg tttgtaagat agcttggatc ccacatcagt    2940
cttgatgcta ataaaatgga tgtccataat cttctaatct ttaatttgtg tctcttacca    3000
aacgagaaaa aataggagaa atccaatttg catgacctca ataaggaaat gttgttaatg    3060
tgtgatgctt gtttctcatt tatagtctag agagagttat catgtccaag attgcagtct    3120
tggtactgag aaagtttgat tgttggttgg ctgcttcttg agcctctttt ttttagagta    3180
agacacttcc tagatataat tttctttatt tttttgtaaa ttccatatat actactacat    3240
taacaggttt aagtttatat taggtgagag agattactca ccagtttgct ccttatgttg    3300
gtcgttggca agctgaagct cagatggccc ttcaagaggt gcagaccaac tcttttagcc    3360
tttttttttc tggcatgtca agtgtggcta ttagattttc tgtgtgattc tcactcccat    3420
atatctatat atgtacatat taaagcacat tgatacctat cttgtcagat gtggtctttt    3480
caattctttt ctaagttgag attcttctct tggtcgtaga tatgctcctg ccgaaatata    3540
ctgctgtctt gttatccatc atgacttggt tatgcttgta tctgggcatt atcttggcat    3600
gcttaaaaac aagtattgaa cgagcctcct attgataaat tttactatta atattggatg    3660
gcttctcaaa ttctaatggc agtgagatac tgttaagttg ggagaaatag attaagaaac    3720
agaaagatgt ttaccatgag agcaattgaa atagaaaata gagtaacttt ttgcaaagat    3780
tttggtcctt tagattgttg aatactacct gataatgaag catttctaa atttatgtgc    3840 tttctatcta tcagatactg gaatacaatc aaattcctat cacgtactga gcattgtgat    3900
cagattcttg cttgcttcct atcacatact ggaatccttt tgattgttga atacaaagat    3960
aatgaagcat tctctaactt tatgtgctgt aactacttat aatgattctt gcttgcctcc    4020
tatcacgtac tcaaatcctt tgtttgattt gtctcttata agaggaactt cctgtctttc    4080
```

```
tttgtcatga cttagtattt atagaggtgc caacttatgg ccttgacaac tgaagctttt   4140
atgcaaactc cggattttgt tgatggaagt acaagtaaca ctttagcatg tggattcagg   4200
tctaacggtt aagactttt aatgaatgtt ttaactgtag tagtttattg atataaaaaa    4260
agtggtctct caaactttt atgagatcat atcgaagtaa tcaaatttat gattcaggtg    4320
cttctgctat tattcttggt taagcatgtg ctattttga cagtctgtca attgtaggct    4380
gcagagaatt ttattgtccg tttgtttgaa gatggtatgc tttgtgcaat tcatgccaaa   4440
cgagttacac tcagtgagta tctgatttcc ttcggtggtg ctgctattat gcattatata   4500
cactttgcct caatatcgtt ataaggag tccttgtttt catatttgtt tgatgcatat     4560
gttatatcct gtttagtggc tgctgcagtt gtgaacttac ggcctgtttg attagtggtc   4620
ataaatgatg gtaatactaa tataatttag tataaatttg taaaaaaaat gctaatatca   4680
atatttatgg taatgaaatt ttatcataaa acatgagttc tcttttataa gttttcatta   4740
ctatccaata ccaccttccc aagtggtaat gaacggtaat gaaattttag gaagaaaatg   4800
gatatttggg gattagatag cattaccatg ggtaatgaca tgagattttc tttacaactt   4860
tatactacga tgcattatca ttaccaccat ttatgaccca taaccaaaaa aaccataatg   4920
tgttaggttc attttcatt tttctaataa tttgcttcat gaattttttc tggagatatc    4980
ttatctagat atttcttgcc aacatgtttc acctgataat tgatcgattt aatagttcag   5040 aacttttccaa aaactatgct gctcggtgtt ggctgtcatc catcagttta agaaaactat   5100
tgacatgatt taagcctcgt cctgtactac taggaagggt aaactattgt tgcttccaaa   5160
aatgtctttt aagggcgtgt tcagcaacaa tagttgtagt agtagctttt agctgttagt   5220
tgtgctcgta gctgttagtg gttagtgtgt aactgttagc tgttcaagta gcggtataag   5280
atattgatgt tcggtaaaag aagctgtcaa atagctgtt tacaaagaat taataaaaaa    5340
ctcaaacaaa gctttaatat ataatttatg caccactaaa gctaccccaa aagctacaaa   5400
ttgtagcttt ttacaaacac tactaaaaca ctacttgtaa cactaaaagc tacttatact   5460 actatttgc caaacattat tatttttct taattagtgt tttgacctag tcaagacact     5520
aaaagctact tgaaaagctt ttgccgaaca cgcccttagt agacaagagg ggggaggggg   5580
tcatcaagaa aatatgatta tactctcaac aaaaaaaaaa tgtaacttaa aaaaaataaa   5640
aataaataat tgactacttc aattaagaaa agaatagaat aaaaacatta cagtggatgt   5700
ctcatccaca tccctaattt aatggcacaa tagaataatt gttttaaatt ttagaaatta   5760
caacacaaga tgtaaattac tcttatcttc ctcttcgtaa tcttttttact cttcctttac   5820 ctcttccttt acctctacat aaaatagaga attagagatt gattaagata attataagat   5880
tttagaaaca ttggttaaga aattcttcaa caaacataat caagtaactc cattatttta   5940
gtttagtgac ttgctattta tcaccctaat ttcaccatct accgccctcc ttggacaata   6000
ttgccccttc cactttcttc actcttcctt cctcacgcat cttatcatct ccttccacta   6060
tcacctttaa aaagtgtgt caggcacaac aaaaacgctt ttatcaaccc acgcgaggcg    6120
aagtacgtca ggcgcaacaa ggcgcgcacc taattctgtc ttttgccaag gctgatggtg   6180
cacttagttt taaaaagcgc agcaaagatg tgcctaggcg caaggcggtg aaaaaattgc   6240
atccgtcagc agcggagtag aggctcacaa caataggtgc gaagaggcgt gcacgtacaa   6300
aagaagcaaa aataagaaac tcaaatatga gacccagtgt ttaacatgta aattcgatac   6360
ccagtgttta acatgtaaat tcgattaaaa gcccttaatt aattgcatga aattaattca   6420
ttttaaccta tactaaaagc cctaatatta gaaaatccta gtttgcaggt tgaggaattt   6480
```

```
ggaaaattga tgattgttgg atttgaaaaa attgttgccg gcgatgaatg tgaggtggtt      6540
tatggcacta gagaggttgg cgttcgttgc cgatgaagct ttccaaggtc attctctcct      6600
tgtcttcttc ctatgcctag ctctcttccc tctccttaat cttctcttct tttctattct      6660
ctctctttat cactacatta tgtttatttc tcgttcttcc cctatgtctt tcacttggac      6720
acttcggggg tatcttcatc ttttatctgc aatttgaagt ttgagaagct tccagagtcg      6780
agtgttaaac ttttgcttct ttttttttaa tcttttgccc ttttttctta gtggcccttg      6840
actagtgatg cacatgtgac caattactaa atgagctttt attttgtctc tcttcttttt      6900
caagcaattt tttttaagta aatcatctaa aacaaagtac tatccatttt agttgtgtaa      6960
atggtgctat tttaaaaccg cacaaaaatt aaaaacataa aaataaaggt gtgcttcgca      7020
tacaagatgt atgcgccttc gtcttgcccc ttttgagact aagactacca taagaactta      7080
gtcacttgag aatggaatgg gtgcaagatg gacgacgata attctaaaga cctctagaag      7140
gatagtgtat agtaactaat acgaaccgaa atataagttt aactaaaatt ttaaagtcta      7200
tatttccata tggtatatgc tggaatacac gaaatgtcca gaatttgtag tggaccacga      7260
tccacacgtc ttttcaggat tctaggtgta ttccaacgaa aaatataaga aaaccatatt      7320
ctactatctg gttgttgtca tcctttcctt gccggcgtga cttctcatcc ttttatttt      7380 gtccggtgct ggtgacacac tttcctatga tagtgtggtg caaagtaagg tgatgatatg      7440
gtgttttgta gaggtgtggt gattttttgtg gtggtgggtg gaagagggggt ggttgcatat      7500 agaaaggggt aagagtcaat gagggggtgga aggggacaag gggtatattg gtaaatgcat      7560
gtaacattag ggtggtgttg agtaattttt gggaagttaa tataaactac ccccttttgg      7620
tacaagagag aatacccgaa ctactgctct gatattttttg ttcacgttat ttgatgtaat      7680
tacgcaatta attgttttc tataagcttc cgcacacaat tgtgcatata aggctagtct      7740
aatatgagac accaacataa ctgactttct tttgcaacga aggtaccttg tcagatttag      7800
aacatagcat caggatttta tttgttgtat ctgtcatcct tgtttattgc tttaattatg      7860
ctttgtatga tgcattttac cacttcgtat gaaaaaaagt gaaatttcat ttagtggtca      7920
tttacatatt acgagttgtg gacatgtttg aacatttgat tttggaaatt ttaagcctca      7980
tattatggag atttattgga cacaaatata gccataattc tccatcaact tgtttctaga      8040
agtgttgctc ttcctgatgt acttgaattc taattaggtt ttatcagaca ttatattata      8100
atgatatgat ttacaatttg ttgtagtgaa aaaggatttg gagctcgcgc gaaggattgg      8160
gggcagagag aggggatggt aactaaacaa cacagatgac tcatttattt aagggccaac      8220
aattgaattc gctgttgatt tcatctgtat atactgctct aggcttctat tccaatgtaa      8280
tttataaatc caaggttagt agcatgttaa gctttgtatt cagtataatg agacttatat      8340
tttgcagttg agatttttagt tgtttgatgt gacttgtaaa ttgtaacttg taagtgacgt      8400
```

<210> SEQ ID NO 90
<211> LENGTH: 462
<212> TYPE: DNA
<213> ORGANISM: Beta vulgaris

<400> SEQUENCE: 90

```
atgagagtta aacacactgc tgccaggaaa tcaaccacca atggtcctcg ttcaaaggct       60
cagaaatctc cgcgcagttt gcaatcacca caatcgcctt ctagtagttc aaagcgcaaa      120
tcacgcagaa acactgatgc aactcctcaa aagaagaagg cttaccgccg taagccgggc      180
```

```
actgtggcac tctgggaaat acgcaaattt cagaagtcat tcaagcccett gattcctgct    240 gcgcctttca ttcgaacagt gagagagatt actcaccagt ttgctcctta tgttggtcgt    300
tggcaagctg aagctcagat ggcccttcaa gaggctgcag agaattttat tgtccgtttg    360
tttgaagatg gtatgctttg tgcaattcat gccaaacgag ttacactcat gaaaaaggat    420
ttggagctcg cgcgaaggat tgggggcaga gagagggat gg                       462

<210> SEQ ID NO 91
<211> LENGTH: 154
<212> TYPE: PRT
<213> ORGANISM: Beta vulgaris

<400> SEQUENCE: 91

Met Arg Val Lys His Thr Ala Ala Arg Lys Ser Thr Thr Asn Gly Pro
1               5                   10                  15

Arg Ser Lys Ala Gln Lys Ser Pro Arg Ser Leu Gln Ser Pro Gln Ser
            20                  25                  30

Pro Ser Ser Ser Lys Arg Lys Ser Arg Arg Asn Thr Asp Ala Thr
        35                  40                  45

Pro Gln Lys Lys Lys Ala Tyr Arg Arg Lys Pro Gly Thr Val Ala Leu
    50                  55                  60

Trp Glu Ile Arg Lys Phe Gln Lys Ser Phe Lys Pro Leu Ile Pro Ala
65                  70                  75                  80

Ala Pro Phe Ile Arg Thr Val Arg Glu Ile Thr His Gln Phe Ala Pro
                85                  90                  95

Tyr Val Gly Arg Trp Gln Ala Glu Ala Gln Met Ala Leu Gln Glu Ala
            100                 105                 110

Ala Glu Asn Phe Ile Val Arg Leu Phe Glu Asp Gly Met Leu Cys Ala
        115                 120                 125

Ile His Ala Lys Arg Val Thr Leu Met Lys Lys Asp Leu Glu Leu Ala
    130                 135                 140

Arg Arg Ile Gly Gly Arg Glu Arg Gly Trp
145                 150

<210> SEQ ID NO 92
<211> LENGTH: 8400
<212> TYPE: DNA
<213> ORGANISM: Beta vulgaris

<400> SEQUENCE: 92
ctactctttc tctctctctc tctctccatt tctgtttgaa atcatgagag ttaaacacac     60
tgctgccagg aaatcaacca ccaacggtcc tcgttcaagt tagtttcctc tctcttcttc    120
ttttttgttc gcattctctc aatctatatt tcaaatttga aaaaaattgt gatgctcata    180
aaccctaaaa ttttcttgta cagaggctca gaaatctccg cgcagtttgc aatcaccaca    240
atcggttctc tctttgtact tttgatttgt ttttccttca tttgttcgat gaatggctct    300
taattgtctt ttatttactt gaaaattgca gccttctagt agttcaaagc gcaaatcact    360
cagaaacact gatgcaactc ctcaaagtaa cttttcttt aatattaggt ttaattttac    420
tgctgtttgc caaattctgt tgaaattgta aatattttt tttcttaaat ttgacggttt     480
cagagaagaa ggcttaccgc cgtaagccgg gcactgtggc actctgggaa atacgcaaat    540
ttcagaagtc attcaagccc ttgattcctg ctgcgccttt cattcgaaca gtatgtattt    600
tttttgtttg tacttaataa atgaattttg gactggtgtt tgtgtggctg catagaaata    660
tatttccata caactgaaat tgtcctagga ggtatcgatg aatgtttgct acaaaataaa    720
```

-continued

```
taaatataag tgattatatc ttgttaaaaa gccattataa ttgcaactta tatgtatgtt      780
gtaatgaggt caactagcta ttttgtgcaa agtcacccac actttaacat aattttgtgc      840
tctcgtaacc ttaaaaaaat ataagtaaag ggttgatttg gtctaattag agctgatgaa      900
acccaattag attgaaacat aaggtgaaat caggtggtga tcagcttcaa ttagatctaa      960
taagtgcagt ttagtttagc ttcggtgaaa tgaacacacc cttaaagata gaaaatcgac     1020
actatatatg gtccttttta gatatgatag ttcgatattc tgttttgggg tgtgttgaat     1080
gattaaatgg agtggtgaat agctgatggg aactagagaa gatgctcagt agacagttat     1140
tgtggagact atattactga ttacccctgt ttctgagtgg ttaggacaat gtgacaattg     1200
attttgggta ttatttgtag atgttttttct ttttgttaaa agtgccaaga taggtgtgca    1260
gttgctgatt ctcagtttgc taagaattag ctgtgtctgt atttcgtacc tcagttgatt    1320
ctaagtgaac atttctttga attgatgctt tgttcttgca tcatgcaact tggtgaagct    1380
ttcttgtagt tgctccagtg gcaatctagt ctggtatgtt tagaactctt gtgatggtat    1440
gagttcatca agatattggt gatccaatta gcctaaccaa tgttttttac ccctattgt     1500 cactgactta tactccctta tctataaaaa taattgtgac attgatccat ctcctcacaa    1560
tcattaatat tatatgtact gaccatcttt acactctcaa cactgaatct aagtagggga    1620
attttgggaa attcaatgat gaactagtac acccttcttc ccaataatat tgttgacctt    1680
tttattttga tttgtcccat attgtcctct ttggtaattt aatgtatatt cacccaattt    1740
tcttttcaat acccactata ccaacatata attggttaat tcattttat taattatatt     1800 tcctaagagc ttgttgtgta aacgtggatg aatttgtagg catggatgaa gtattgttat    1860
aatgaggtga caacattact taatttcgaa ctgagggaca gagggatatg atgataaaac    1920
aacttttgct tgcttcttaa actcagaaga tagggtttac accaagtggc atgtaaaagt    1980
cactagatga ttatctatta caagggcttg tacaatctga agtacgatag gatttgaagt    2040
taacaacatt catcgaaagc tcataacttg tccttatatc aatataagtt gctggcatgt    2100
gaaattgcgt tgcaagcatc catgagctag ctcaactatt aactattaaa ctttatattt    2160
ttgcttgatc tagtatgagt cctactattt agtttctcca tctaccttaa tatgtcgcat    2220
acaccaacta atcattatcg ctagaatcaa taaacaaagc tttctttcct taggtgtatt    2280
agtacctagc tcctgtaata ccaagagcac ccaaattggg aagaaaaagt agaattggct    2340
catatctcta atcctacatt gatcattgaa aaggacctta aggttctcat actgaaacat    2400 catcttttg agcaggatat ctacgtagac gacaagaaag actactttgg ttgcccgtgc     2460
atttgagtgc atcagacaac ttctttacca ctgtctaacg gcttgctttg gccatattgt    2520
ggtcttctat gccaaaatta atgatatttc ttggcaccgc gctaatgata ttactgaatg    2580
cggatatcgt acgattagaa tttattcaaa gtaggtagca attactagtt ttgagcattg    2640
agtttcaata attagtaaat taagtgctaa acttgtacat tttggctaca tgtatttgaa    2700
ttagaattgg tacgaggaaa tatagcaaca ttacgggcaa tgttcactca agtagaagcc    2760
attacatcaa aatagtactag ttgaagtatt agttctcata atactaatca ttgtcattaa    2820
tggaatattg gaacgtaaat gcctttaagg tgctgtagtt ttagtagaaa ttctactatt    2880
ctagtatgat aatgcaattt attgaaactg tttgtaagat agcttggatc ccacatcagt    2940
cttgatgcta aataaatgga tgtccataat cttctaatct ttaatttgtg tctcttacca    3000
aacgagaaaa aataggagaa atccaatttg catgacctca ataaggaaat gttgttaatg    3060
```

-continued

```
tgtgatgctt gtttctcatt tatagtctag agagagttat catgtccaag attgcagtct    3120
tggtactgag aaagtttgat tgttggttgg ctgcttcttg agcctctttt ttttagagta    3180
agacacttcc tagatataat tttctttatt tttttgtaaa ttccatatat actactacat    3240
taacaggttt aagtttatat taggtgagag agattactca ccagtttgct ccttatgttg    3300
gtcgttggca agctgaagct ctgatggccc ctcaagaggt gcagaccaac tcttttagcc    3360
tttttttttc tggcatgtca agtgtggcta ttagattttc tgtgtgattc tcactcccat    3420
atatctatat atgtacatat taaagcacat tgatacctat cttgtcagat gtggtctttt    3480
caattctttt ctaagttgag attcttctct tggtcgtaga tatgctcctg ccgaaatata    3540
ctgctgtctt gttatccatc atgacttggt tatgcttgta tctgggcatt atcttggcat    3600
gcttaaaaac aagtattgaa cgagcctcct attgataaat tttactatta atattggatg    3660
gcttctcaaa ttctaatggc agtgagatac tgttaagttg ggagaaatag attaagaaac    3720
agaaagatgt ttaccatgag agcaattgaa atagaaaata gagtaacttt ttgcaaagat    3780
tttggtcctt tagattgttg aatactacct gataatgaag catttttctaa atttatgtgc    3840
tttctatcta tcagatactg gaatacaatc aaattcctat cacgtactga gcattgtgat    3900
cagattcttg cttgcttcct atcacatact ggaatccttt tgattgttga atacaaagat    3960
aatgaagcat tctctaactt tatgtgctgt aactacttat aatgattctt gcttgcctcc    4020
tatcacgtac tcaaatcctt tgtttgattt gtctcttata agaggaactt cctgtctttc    4080
tttgtcatga cttagtattt atagaggtgc caacttatgg ccttgacaac tgaagctttt    4140
atgcaaactc cggattttgt tgatggaagt acaagtaaca ctttagcatg tggattcagg    4200
tctaacggtt aagacttttt aatgaatgtt ttaactgtag tagtttattg atataaaaaa    4260
agtggtctct caaactttt atgagatcat atcgaagtaa tcaaatttat gattcaggtg    4320
cttctgctat tattcttggt taagcatgtg ctatttttga cagtctgtca attgtaggct    4380
gcagagaatt ttattgtccg tttgtttgaa gatggtatgc tttgtgcaat tcatgccaaa    4440
cgagttacac tcagtgagta tctgatttcc ttcggtggtg ctgctattat gcattatata    4500
cactttgcct caatatcgtt atataaggag tccttgtttt catatttgtt tgatgcatat    4560
gttatatcct gtttagtggc tgctgcagtt gtgaacttac ggcctgtttg attagtggtc    4620
ataaatgatg gtaatactaa tataatttag tataaatttg taaaaaaaat gctaatatca    4680
atatttatgg taatgaaatt ttatcataaa acatgagttc tcttttataa gttttcatta    4740
ctatccaata ccaccttccc aagtggtaat gaacggtaat gaaattttag gaagaaaatg    4800
gatatttggg gattagatag cattaccatg ggtaatgaca tgagattttc tttacaactt    4860
tatactacga tgcattatca ttaccaccat ttatgaccca taaccaaaaa aaccataatg    4920
tgttaggttc atttttcatt tttctaataa tttgcttcat gaattttttc tggagatatc    4980
ttatctagat atttcttgcc aacatgtttc acctgataat tgatcgattt aatagttcag    5040
aactttccaa aaactatgct gctcggtgtt ggctgtcatc catcagttta agaaaactat    5100
tgacatgatt taagcctcgt cctgtactac taggaagggt aaactattgt tgcttccaaa    5160
aatgtctttt aagggcgtgt tcagcaacaa tagttgtagt agtagctttt agctgttagt    5220
tgtgctcgta gctgttagtg gttagtgtgt aactgttagc tgttcaagta gcggtataag    5280
atattgatgt tcggtaaaag aagctgtcaa aatagctgtt tacaaagaat taataaaaaa    5340
ctcaaacaaa gctttaatat ataatttatg caccactaaa gctaccccaa aagctacaaa    5400
ttgtagcttt ttacaaacac tactaaaaca ctacttgtaa cactaaaagc tacttatact    5460
```

-continued

```
actattttgc caaacattat tattttttct taattagtgt tttgacctag tcaagacact    5520
aaaagctact tgaaaagctt ttgccgaaca cgcccttagt agacaagagg ggggaggggg    5580
tcatcaagaa aatatgatta tactctcaac aaaaaaaaaa tgtaacttaa aaaaaataaa    5640
aataaataat tgactacttc aattaagaaa agaatagaat aaaaacatta cagtggatgt    5700
ctcatccaca tccctaattt aatggcacaa tagaataatt gttttaaatt ttagaaatta    5760
caacacaaga tgtaaattac tcttatcttc ctcttcgtaa tcttttttact cttcctttac    5820 ctcttccttt acctctacat aaaatagaga attagagatt gattaagata attataagat    5880
tttagaaaca ttggttaaga aattcttcaa caaacataat caagtaactc cattattta    5940 gtttagtgac ttgctatttta tcaccctaat ttcaccatct accgccctcc ttggacaata    6000
ttgccccttc cactttcttc actcttcctt cctcacgcat cttatcatct ccttccacta    6060
tcacctttaa aaagtgtgt caggcacaac aaaaacgctt ttatcaaccc acgcgaggcg    6120
aagtacgtca ggcgcaacaa ggcgcgcacc taattctgtc ttttgccaag gctgatggtg    6180
cacttagttt taaaaagcgc agcaaagatg tgcctaggcg caaggcggtg aaaaaattgc    6240
atccgtcagc agcggagtag aggctcacaa caataggtgc gaagaggcgt gcacgtacaa    6300
aagaagcaaa aataagaaac tcaaatatga gacccagtgt ttaacatgta aattcgatac    6360
ccagtgttta acatgtaaat tcgattaaaa gcccttaatt aattgcatga aattaattca    6420
ttttaaccta tactaaaagc cctaatatta gaaaatccta gtttgcaggt tgaggaattt    6480
ggaaaattga tgattgttgg atttgaaaaa attgttgccg gcgatgaatg tgaggtggtt    6540
tatggcacta gagaggttgg cgttcgttgc cgatgaagct ttccaaggtc attctctcct    6600
tgtcttcttc ctatgcctag ctctcttccc tctccttaat cttctcttct tttctattct    6660
ctctctttat cactacatta tgtttatttc tcgttcttcc cctatgtctt tcacttggac    6720
acttcggggg tatcttcatc ttttatctgc aatttgaagt ttgagaagct tccagagtcg    6780
agtgttaaac ttttgcttct ttttttttaa tcttttgccc ttttttctta gtggcccttg    6840
actagtgatg cacatgtgac caattactaa atgagctttt attttgtctc tcttcttttt    6900
caagcaattt ttttttaagta aatcatctaa acaaagtac tatccatttt agttgtgtaa    6960
atggtgctat tttaaaaccg cacaaaaatt aaaaacataa aaataaaggt gtgcttcgca    7020
tacaagatgt atgcgccttc gtcttgcccc ttttgagact aagactacca taagaactta    7080
gtcacttgag aatggaatgg gtgcaagatg gacgacgata attctaaaga cctctagaag    7140
gatagtgtat agtaactaat acgaaccgaa atataagttt aactaaaatt ttaaagtcta    7200
tatttccata tggtatatgc tggaatacac gaaatgtcca gaatttgtag tggaccacga    7260
tccacacgtc ttttcaggat tctaggtgta ttccaacgaa aaatataaga aaaccatatt    7320
ctactatctg gttgttgtca tccttttcctt gccggcgtga cttctcatcc ttttattttt    7380
gtccggtgct ggtgacacac tttcctatga tagtgtggtg caaagtaagg tgatgatatg    7440
gtgttttgta gaggtgtggt gattttttgtg gtggtgggtg gaagaggggt ggttgcatat    7500 agaaagggt aagagtcaat gaggggtgga aggggacaag gggtatattg gtaaatgcat    7560
gtaacattag ggtggtgttg agtaattttt gggaagttaa tataaactac ccccttttgg    7620
tacaagagag aatacccgaa ctactgctct gatattttg ttcacgttat ttgatgtaat    7680
tacgcaatta atttgttttc tataagcttc cgcacacaat tgtgcatata aggctagtct    7740
aatatgagac accaacataa ctgactttct tttgcaacga aggtaccttg tcagatttag    7800
```

| | |
|---|---:|
| aacatagcat caggatttta tttgttgtat ctgtcatcct tgtttattgc tttaattatg | 7860 |
| ctttgtatga tgcattttac cacttcgtat gaaaaaagt gaaatttcat ttagtggtca | 7920 |
| tttacatatt acgagttgtg gacatgtttg aacatttgat tttggaaatt ttaagcctca | 7980 |
| tattatggag atttattgga cacaaatata gccataattc tccatcaact tgtttctaga | 8040 |
| agtgttgctc ttcctgatgt acttgaattc taattaggtt ttatcagaca ttatattata | 8100 |
| atgatatgat ttacaatttg ttgtagtgaa aaaggatttg gagctcgcgc gaaggattgg | 8160 |
| gggcagagag aggggatggt aactaaacaa cacagatgac tcatttattt aagggccaac | 8220 |
| aattgaattc gctgttgatt tcatctgtat atactgctct aggcttctat tccaatgtaa | 8280 |
| tttataaatc caaggttagt agcatgttaa gctttgtatt cagtataatg agacttatat | 8340 |
| tttgcagttg agattttagt tgtttgatgt gacttgtaaa ttgtaacttg taagtgacgt | 8400 |

<210> SEQ ID NO 93
<211> LENGTH: 462
<212> TYPE: DNA
<213> ORGANISM: Beta vulgaris

<400> SEQUENCE: 93

| | |
|---|---:|
| atgagagtta aacacactgc tgccaggaaa tcaaccacca atggtcctcg ttcaaaggct | 60 |
| cagaaatctc cgcgcagttt gcaatcacca caatcgcctt ctagtagttc aaagcgcaaa | 120 |
| tcacgcagaa acactgatgc aactcctcaa agaagaagg cttaccgccg taagccgggc | 180 |
| actgtggcac tctgggaaat acgcaaattt cagaagtcat tcaagcccttt gattcctgct | 240 |
| gcgcctttca ttcgaacagt gagagagatt actcaccagt ttgctcctta tgttggtcgt | 300 |
| tggcaagctg aagctctgat ggcccctcaa gaggctgcag agaattttat tgtccgtttg | 360 |
| tttgaagatg gtatgctttg tgcaattcat gccaaacgag ttacactcat gaaaaaggat | 420 |
| ttggagctcg cgcgaaggat tgggggcaga gagagggat gg | 462 |

<210> SEQ ID NO 94
<211> LENGTH: 154
<212> TYPE: PRT
<213> ORGANISM: Beta vulgaris

<400> SEQUENCE: 94

Met Arg Val Lys His Thr Ala Ala Arg Lys Ser Thr Thr Asn Gly Pro
1               5                   10                  15

Arg Ser Lys Ala Gln Lys Ser Pro Arg Ser Leu Gln Ser Pro Gln Ser
            20                  25                  30

Pro Ser Ser Ser Lys Arg Lys Ser Arg Arg Asn Thr Asp Ala Thr
        35                  40                  45

Pro Gln Lys Lys Ala Tyr Arg Arg Lys Pro Gly Thr Val Ala Leu
    50                  55                  60

Trp Glu Ile Arg Lys Phe Gln Lys Ser Phe Lys Pro Leu Ile Pro Ala
65                  70                  75                  80

Ala Pro Phe Ile Arg Thr Val Arg Glu Ile Thr His Gln Phe Ala Pro
                85                  90                  95

Tyr Val Gly Arg Trp Gln Ala Glu Ala Leu Met Ala Pro Gln Glu Ala
            100                 105                 110

Ala Glu Asn Phe Ile Val Arg Leu Phe Glu Asp Gly Met Leu Cys Ala
        115                 120                 125

Ile His Ala Lys Arg Val Thr Leu Met Lys Lys Asp Leu Glu Leu Ala
    130                 135                 140

Arg Arg Ile Gly Gly Arg Glu Arg Gly Trp
145                 150

<210> SEQ ID NO 95
<211> LENGTH: 8400
<212> TYPE: DNA
<213> ORGANISM: Beta vulgaris

<400> SEQUENCE: 95

| | | | | | |
|---|---|---|---|---|---|
| ctactctttc | tctctctctc | tctctccatt | tctgtttgaa | atcatgagag | ttaaacacac | 60 |
| tgctgccagg | aaatcaacca | ccaacggtcc | tcgttcaagt | tagtttcctc | tctcttcttc | 120 |
| ttttttgttc | gcattctctc | aatctatatt | tcaaatttga | aaaaaattgt | gatgctcata | 180 |
| aaccctaaaa | ttttcttgta | cagaggctca | gaaatctccg | cgcagtttgc | aatcaccaca | 240 |
| atcggttctc | tctttgtact | tttgatttgt | ttttccttca | tttgttcgat | gaatggctct | 300 |
| taattgtctt | ttatttactt | gaaaattgca | gccttctagt | agttcaaagc | gcaaatcact | 360 |
| cagaaacact | gatgcaactc | ctcaaagtaa | ctttttcttt | aatattaggt | ttaattttac | 420 |
| tgctgtttgc | caaattctgt | tgaaattgta | aaatatttt | tttcttaaat | ttgacggttt | 480 |
| cagagaagaa | ggcttaccgc | cgtaagccgg | gcactgtggc | actctgggaa | atacgcaaat | 540 |
| ttcagaagtc | attcaagccc | ttgattcctg | ctgcgccttt | cattcgaaca | gtatgtattt | 600 |
| tttttgtttg | tacttaataa | atgaattttg | gactggtgtt | tgtgtggctg | catagaaata | 660 |
| tatttccata | caactgaaat | tgtcctagga | ggtatcgatg | aatgtttgct | acaaaataaa | 720 |
| taaatataag | tgattatatc | ttgttaaaaa | gccattataa | ttgcaactta | tatgtatgtt | 780 |
| gtaatgaggt | caactagcta | ttttgtgcaa | agtcacccac | actttaacat | aattttgtgc | 840 |
| tctcgtaacc | ttaaaaaaat | ataagtaaag | ggttgatttg | gtctaattag | agctgatgaa | 900 |
| acccaattag | attgaaacat | aaggtgaaat | caggtggtga | tcagcttcaa | ttagatctaa | 960 |
| taagtgcagt | ttagtttagc | ttcggtgaaa | tgaacacacc | cttaaagata | gaaaatcgac | 1020 |
| actatatatg | gtccttttta | gatatgatag | ttcgatattc | tgttttgggg | tgtgttgaat | 1080 |
| gattaaatgg | agtggtgaat | agctgatggg | aactagagaa | gatgctcagt | agacagttat | 1140 |
| tgtggagact | atattactga | ttaccctgt | ttctgagtgg | ttaggacaat | gtgacaattg | 1200 |
| attttgggta | ttatttgtag | atgttttct | ttttgttaaa | agtgccaaga | taggtgtgca | 1260 |
| gttgctgatt | ctcagtttgc | taagaattag | ctgtgtctgt | atttcgtacc | tcagttgatt | 1320 |
| ctaagtgaac | atttctttga | attgatgctt | tgttcttgca | tcatgcaact | tggtgaagct | 1380 |
| ttcttgtagt | tgctccagtg | gcaatctagt | ctggtatgtt | tagaactctt | gtgatggtat | 1440 |
| gagttcatca | agatattggt | gatccaatta | gcctaaccaa | tgttttttac | ccctattgt | 1500 |
| cactgactta | tactccctta | tctataaaaa | taattgtgac | attgatccat | ctcctcacaa | 1560 |
| tcattaatat | tatatgtact | gaccatcttt | acactctcaa | cactgaatct | aagtagggga | 1620 |
| attttgggaa | attcaatgat | gaactagtac | acccttcttc | ccaataatat | tgttgacctt | 1680 |
| tttattttga | tttgtcccat | attgtcctct | ttggtaattt | aatgtatatt | cacccaattt | 1740 |
| tcttttcaat | acccactata | ccaacatata | attggttaat | tcatttttat | taattatatt | 1800 |
| tcctaagagc | ttgttgtgta | aacgtggatg | aatttgtagg | catggatgaa | gtattgttat | 1860 |
| aatgaggtga | caacattact | taatttcgaa | ctgagggaca | gagggatatg | atgataaaac | 1920 |
| aacttttgct | tgcttcttaa | actcagaaga | tagggtttac | accaagtggc | atgtaaaagt | 1980 |
| cactagatga | ttatctatta | caagggcttg | tacaatctga | agtacgatag | gatttgaagt | 2040 |

-continued

```
taacaacatt catcgaaagc tcataacttg tccttatatc aatataagtt gctggcatgt   2100
gaaattgcgt tgcaagcatc catgagctag ctcaactatt aactattaaa ctttatattt   2160
ttgcttgatc tagtatgagt cctactattt agtttctcca tctaccttaa tatgtcgcat   2220
acaccaacta atcattatcg ctagaatcaa taaacaaagc tttctttcct taggtgtatt   2280
agtacctagc tcctgtaata ccaagagcac ccaaattggg aagaaaaagt agaattggct   2340
catatctcta atcctacatt gatcattgaa aaggacctta aggttctcat actgaaacat   2400 catcttttg agcaggatat ctacgtagac gacaagaaag actactttgg ttgcccgtgc   2460
atttgagtgc atcagacaac ttctttacca ctgtctaacg gcttgctttg gccatattgt   2520
ggtcttctat gccaaaatta atgatatttc ttggcaccgc gctaatgata ttactgaatg   2580
cggatatcgt acgattagaa tttattcaaa gtaggtagca attactagtt ttgagcattg   2640
agtttcaata attagtaaat taagtgctaa acttgtacat tttggctaca tgtatttgaa   2700
ttagaattgg tacgaggaaa tatagcaaca ttacgggcaa tgttcactca agtagaagcc   2760
attacatcaa atagtactag ttgaagtatt agttctcata atactaatca ttgtcattaa   2820
tggaatattg aacgtaaat gcctttaagg tgctgtagtt ttagtagaaa ttctactatt   2880
ctagtatgat aatgcaattt attgaaactg tttgtaagat agcttggatc ccacatcagt   2940
cttgatgcta aataaatgga tgtccataat cttctaatct taatttgtg tctcttacca   3000 aacgagaaaa aataggagaa atccaatttg catgacctca ataaggaaat gttgttaatg   3060
tgtgatgctt gtttctcatt tatagtctag agagagttat catgtccaag attgcagtct   3120
tggtactgag aaagtttgat tgttggttgg ctgcttcttg agcctctttt ttttagagta   3180
agacacttcc tagatataat tttctttatt tttttgtaaa ttccatatat actactacat   3240
taacaggttt aagtttatat taggtgagag agattactca ccagtttgct ccttatgttg   3300
gtcgttggca agctgaagct ctgatggccc ttctagaggt gcagaccaac tcttttagcc   3360 ttttttttc tggcatgtca agtgtggcta ttagattttc tgtgtgattc tcactcccat   3420
atatctatat atgtacatat taaagcacat tgatacctat cttgtcagat gtggtctttt   3480
caattctttt ctaagttgag attcttctct tggtcgtaga tatgctcctg ccgaaatata   3540
ctgctgtctt gttatccatc atgacttggt tatgcttgta tctgggcatt atcttggcat   3600
gcttaaaaac aagtattgaa cgagcctcct attgataaat tttactatta atattggatg   3660
gcttctcaaa ttctaatggc agtgagatac tgttaagttg ggagaaatag attaagaaac   3720
agaaagatgt ttaccatgag agcaattgaa atagaaaata gagtaacttt ttgcaaagat   3780
tttggtcctt tagattgttg aatactacct gataatgaag cattttctaa atttatgtgc   3840
tttctatcta tcagatactg gaatacaatc aaattcctat cacgtactga gcattgtgat   3900
cagattcttg cttgcttcct atcacatact ggaatccttt tgattgttga atacaaagat   3960
aatgaagcat tctctaactt tatgtgctgt aactacttat aatgattctt gcttgcctcc   4020
tatcacgtac tcaaatcctt tgtttgattt gtctcttata agaggaactt cctgtctttc   4080
tttgtcatga cttagtattt atagaggtgc caacttatgg ccttgacaac tgaagctttt   4140
atgcaaactc cggattttgt tgatggaagt acaagtaaca ctttagcatg tggattcagg   4200
tctaacggtt aagacttttt aatgaatgtt ttaactgtag tagtttattg atataaaaaa   4260
agtggtctct caaacttttt atgagatcat atcgaagtaa tcaaatttat gattcaggtg   4320
cttctgctat tattcttggt taagcatgtg ctatttttga cagtctgtca attgtaggct   4380
gcagagaatt ttattgtccg tttgtttgaa gatggtatgc tttgtgcaat tcatgccaaa   4440
```

```
cgagttacac tcagtgagta tctgatttcc ttcggtggtg ctgctattat gcattatata    4500
cactttgcct caatatcgtt atataaggag tccttgtttt catatttgtt tgatgcatat    4560
gttatatcct gtttagtggc tgctgcagtt gtgaacttac ggcctgtttg attagtggtc    4620
ataaatgatg gtaatactaa tataatttag tataaatttg taaaaaaaat gctaatatca    4680
atatttatgg taatgaaatt ttatcataaa acatgagttc tcttttataa gttttcatta    4740
ctatccaata ccaccttccc aagtggtaat gaacggtaat gaaattttag gaagaaaatg    4800
gatatttggg gattagatag cattaccatg ggtaatgaca tgagattttc tttacaactt    4860
tatactacga tgcattatca ttaccaccat ttatgaccca taaccaaaaa aaccataatg    4920
tgttaggttc atttttcatt tttctaataa tttgcttcat gaatttttc tggagatatc    4980 ttatctagat atttcttgcc aacatgtttc acctgataat tgatcgattt aatagttcag    5040
aactttccaa aaactatgct gctcggtgtt ggctgtcatc catcagttta agaaaactat    5100
tgacatgatt taagcctcgt cctgtactac taggaagggt aaactattgt tgcttccaaa    5160
aatgtctttt aagggcgtgt tcagcaacaa tagttgtagt agtagctttt agctgttagt    5220
tgtgctcgta gctgttagtg gttagtgtgt aactgttagc tgttcaagta gcggtataag    5280
atattgatgt tcggtaaaag aagctgtcaa aatagctgtt tacaaagaat taataaaaaa    5340
ctcaaacaaa gctttaatat ataatttatg caccactaaa gctaccccaa aagctacaaa    5400
ttgtagcttt ttacaaacac tactaaaaca ctacttgtaa cactaaaagc tacttatact    5460
actattttgc caaacattat tattttttct taattagtgt tttgacctag tcaagacact    5520
aaaagctact tgaaaagctt ttgccgaaca cgcccttagt agacaagagg ggggagggg    5580 tcatcaagaa aatatgatta tactctcaac aaaaaaaaaa tgtaacttaa aaaaaataaa    5640
aataaataat tgactacttc aattaagaaa agaatagaat aaaaacatta cagtggatgt    5700
ctcatccaca tccctaattt aatggcacaa tagaataatt gttttaaatt ttagaaatta    5760
caacacaaga tgtaaattac tcttatcttc ctcttcgtaa tctttttact cttcctttac    5820
ctcttccttt acctctacat aaaatagaga attagagatt gattaagata attataagat    5880
tttagaaaca ttggttaaga aattcttcaa caaacataat caagtaactc cattatttta    5940
gtttagtgac ttgctattta tcaccctaat ttcaccatct accgccctcc ttggacaata    6000
ttgccccttc cactttcttc actcttcctt cctcacgcat cttatcatct ccttccacta    6060
tcacctttaa aaagtgtgt caggcacaac aaaaacgctt ttatcaaccc acgcgaggcg    6120
aagtacgtca ggcgcaacaa ggcgcgcacc taattctgtc ttttgccaag gctgatggtg    6180
cacttagttt taaaagcgc agcaaagatg tgcctaggcg caaggcggtg aaaaaattgc    6240
atccgtcagc agcggagtag aggctcacaa caataggtgc gaagaggcgt gcacgtacaa    6300
aagaagcaaa aataagaaac tcaaatatga gacccagtgt ttaacatgta aattcgatac    6360
ccagtgttta acatgtaaat tcgattaaaa gcccttaatt aattgcatga aattaattca    6420
ttttaaccta tactaaaagc cctaatatta gaaaatccta gtttgcaggt tgaggaattt    6480
ggaaaattga tgattgttgg atttgaaaaa attgttgccg gcgatgaatg tgaggtggtt    6540
tatggcacta gagaggttgg cgttcgttgc cgatgaagct ttccaaggtc attctctcct    6600
tgtcttcttc ctatgcctag ctctcttccc tctccttaat cttctcttct tttctattct    6660
ctctctttat cactacatta tgtttatttc tcgttcttcc cctatgtctt tcacttggac    6720
acttcggggg tatcttcatc ttttatctgc aatttgaagt ttgagaagct tccagagtcg    6780
```

| | |
|---|---:|
| agtgttaaac ttttgcttct ttttttttaa tcttttgccc ttttttctta gtggcccttg | 6840 |
| actagtgatg cacatgtgac caattactaa atgagctttt attttgtctc tcttcttttt | 6900 |
| caagcaattt tttttaagta aatcatctaa acaaagtac tatccatttt agttgtgtaa | 6960 |
| atggtgctat tttaaaaccg cacaaaaatt aaaaacataa aaataaaggt gtgcttcgca | 7020 |
| tacaagatgt atgcgccttc gtcttgcccc ttttgagact aagactacca taagaactta | 7080 |
| gtcacttgag aatggaatgg gtgcaagatg gacgacgata attctaaaga cctctagaag | 7140 |
| gatagtgtat agtaactaat acgaaccgaa atataagttt aactaaaatt ttaaagtcta | 7200 |
| tatttccata tggtatatgc tggaatacac gaaatgtcca gaatttgtag tggaccacga | 7260 |
| tccacacgtc ttttcaggat tctaggtgta ttccaacgaa aaatataaga aaaccatatt | 7320 |
| ctactatctg gttgttgtca tccttttcctt gccggcgtga cttctcatcc ttttattttt | 7380 |
| gtccggtgct ggtgacacac tttcctatga tagtgtggtg caaagtaagg tgatgatatg | 7440 |
| gtgttttgta gaggtgtggt gattttttgtg gtggtgggtg gaagaggggt ggttgcatat | 7500 |
| agaaaggggt aagagtcaat gaggggtgga agggacaag gggtatattg gtaaatgcat | 7560 |
| gtaacattag ggtggtgttg agtaattttt gggaagttaa tataaactac cccttttgg | 7620 |
| tacaagagag aatacccgaa ctactgctct gatattttg ttcacgttat ttgatgtaat | 7680 |
| tacgcaatta atttgttttc tataagcttc cgcacacaat tgtgcatata aggctagtct | 7740 |
| aatatgagac accaacataa ctgactttct tttgcaacga aggtaccttg tcagatttag | 7800 |
| aacatagcat caggatttta tttgttgtat ctgtcatcct tgtttattgc tttaattatg | 7860 |
| ctttgtatga tgcatttac cacttcgtat gaaaaaagt gaaatttcat ttagtggtca | 7920 |
| tttacatatt acgagttgtg gacatgtttg aacatttgat tttggaaatt ttaagcctca | 7980 |
| tattatggag atttattgga cacaaatata gccataattc tccatcaact tgtttctaga | 8040 |
| agtgttgctc ttcctgatgt acttgaattc taattaggtt ttatcagaca ttatattata | 8100 |
| atgatatgat ttacaatttg ttgtagtgaa aaaggatttg gagctcgcgc gaaggattgg | 8160 |
| gggcagagag aggggatggt aactaaacaa cacagatgac tcatttattt aagggccaac | 8220 |
| aattgaattc gctgttgatt tcatctgtat atactgctct aggcttctat tccaatgtaa | 8280 |
| tttataaatc caaggttagt agcatgttaa gctttgtatt cagtataatg agacttatat | 8340 |
| tttgcagttg agattttagt tgtttgatgt gacttgtaaa ttgtaacttg taagtgacgt | 8400 |

<210> SEQ ID NO 96
<211> LENGTH: 462
<212> TYPE: DNA
<213> ORGANISM: Beta vulgaris

<400> SEQUENCE: 96

| | |
|---|---:|
| atgagagtta aacacactgc tgccaggaaa tcaaccacca atggtcctcg ttcaaaggct | 60 |
| cagaaatctc cgcgcagttt gcaatcacca caatcgcctt ctagtagttc aaagcgcaaa | 120 |
| tcacgcagaa acactgatgc aactcctcaa aagaagaagg cttaccgccg taagccgggc | 180 |
| actgtggcac tctgggaaat acgcaaattt cagaagtcat tcaagcccct gattcctgct | 240 |
| gcgcctttca ttcgaacagt gagagagatt actcaccagt ttgctcctta tgttggtcgt | 300 |
| tggcaagctg aagctctgat ggcccttcta gaggctgcag agaattttat tgtccgtttg | 360 |
| tttgaagatg gtatgctttg tgcaattcat gccaaacgag ttacactcat gaaaaaggat | 420 |
| ttggagctcg cgcgaaggat tgggggcaga gagagggat gg | 462 |

```
<210> SEQ ID NO 97
<211> LENGTH: 154
<212> TYPE: PRT
<213> ORGANISM: Beta vulgaris

<400> SEQUENCE: 97

Met Arg Val Lys His Thr Ala Ala Arg Lys Ser Thr Thr Asn Gly Pro
1               5                   10                  15

Arg Ser Lys Ala Gln Lys Ser Pro Arg Ser Leu Gln Ser Pro Gln Ser
                20                  25                  30

Pro Ser Ser Ser Lys Arg Lys Ser Arg Arg Asn Thr Asp Ala Thr
            35                  40                  45

Pro Gln Lys Lys Lys Ala Tyr Arg Arg Lys Pro Gly Thr Val Ala Leu
        50                  55                  60

Trp Glu Ile Arg Lys Phe Gln Lys Ser Phe Lys Pro Leu Ile Pro Ala
65                  70                  75                  80

Ala Pro Phe Ile Arg Thr Val Arg Glu Ile Thr His Gln Phe Ala Pro
                85                  90                  95

Tyr Val Gly Arg Trp Gln Ala Glu Ala Leu Met Ala Leu Leu Glu Ala
                100                 105                 110

Ala Glu Asn Phe Ile Val Arg Leu Phe Glu Asp Gly Met Leu Cys Ala
            115                 120                 125

Ile His Ala Lys Arg Val Thr Leu Met Lys Lys Asp Leu Glu Leu Ala
        130                 135                 140

Arg Arg Ile Gly Gly Arg Glu Arg Gly Trp
145                 150
```